US007994222B2

(12) United States Patent
Ossovskaya et al.

(10) Patent No.: US 7,994,222 B2
(45) Date of Patent: Aug. 9, 2011

(54) MONITORING OF THE INHIBITION OF FATTY ACID SYNTHESIS BY IODO-NITROBENZAMIDE COMPOUNDS

(75) Inventors: Valeria S. Ossovskaya, San Francisco, CA (US); Barry M. Sherman, Hillsborough, CA (US)

(73) Assignee: BiPar Sciences, Inc., South San Francisco, CA (US)

( * ) Notice: Subject to any disclaimer, the term of this patent is extended or adjusted under 35 U.S.C. 154(b) by 735 days.

(21) Appl. No.: 11/850,624

(22) Filed: Sep. 5, 2007

(65) Prior Publication Data

US 2008/0103208 A1 May 1, 2008

Related U.S. Application Data

(60) Provisional application No. 60/842,479, filed on Sep. 5, 2006.

(51) Int. Cl.
*A61K 31/165* (2006.01)
*A61P 3/04* (2006.01)

(52) U.S. Cl. ........................................ 514/617; 514/613

(58) Field of Classification Search ........................ None
See application file for complete search history.

(56) References Cited

U.S. PATENT DOCUMENTS

| | | | |
|---|---|---|---|
| 2,006,735 A | 7/1935 | Fischer et al. |
| 2,937,204 A | 5/1950 | Harris et al. |
| 2,669,583 A | 2/1954 | Clinton et al. |
| 3,161,564 A | 12/1964 | Morehouse |
| 3,228,833 A | 1/1966 | Crounse et al. |
| 4,604,463 A | 8/1986 | Miyasaka et al. |
| 4,923,885 A | 5/1990 | Hupe et al. |
| 5,032,617 A | 7/1991 | Lee et al. |
| 5,041,653 A | 8/1991 | Lee et al. |
| 5,162,532 A | 11/1992 | Comins et al. |
| 5,177,075 A | 1/1993 | Sato et al. |
| 5,191,082 A | 3/1993 | Comins et al. |
| 5,200,524 A | 4/1993 | Comins et al. |
| 5,215,738 A | 6/1993 | Lee et al. |
| 5,223,608 A | 6/1993 | Chou et al. |
| 5,232,735 A | 8/1993 | Kurtz et al. |
| 5,243,050 A | 9/1993 | Comins et al. |
| 5,247,089 A | 9/1993 | Comins et al. |
| 5,262,564 A | 11/1993 | Kun et al. |
| 5,283,352 A | 2/1994 | Bäckström et al. |
| 5,321,140 A | 6/1994 | Comins et al. |
| 5,420,319 A | 5/1995 | Okamoto et al. |
| 5,434,254 A | 7/1995 | Chou et al. |
| 5,464,871 A | 11/1995 | Kun et al. |
| 5,473,074 A | 12/1995 | Kun et al. |
| 5,482,833 A | 1/1996 | Pero et al. |
| 5,482,975 A | 1/1996 | Kun et al. |
| 5,484,951 A | 1/1996 | Kun et al. |
| 5,516,941 A | 5/1996 | Kun et al. |
| 5,519,053 A | 5/1996 | Kun et al. |
| 5,583,155 A | 12/1996 | Kun et al. |
| 5,631,038 A | 5/1997 | Kurtz et al. |
| 5,631,231 A | 5/1997 | Kurtz et al. |
| 5,631,232 A | 5/1997 | Kurtz et al. |
| 5,631,240 A | 5/1997 | Kurtz et al. |
| 5,631,252 A | 5/1997 | Kurtz et al. |
| 5,631,272 A | 5/1997 | Kurtz et al. |
| 5,631,292 A | 5/1997 | Kurtz et al. |
| 5,631,294 A | 5/1997 | Kurtz et al. |
| 5,631,295 A | 5/1997 | Kurtz et al. |
| 5,631,299 A | 5/1997 | Kurtz et al. |
| 5,633,282 A | 5/1997 | Collins et al. |
| 5,637,618 A | 6/1997 | Kurtz et al. |
| 5,639,788 A | 6/1997 | Kurtz et al. |
| 5,641,795 A | 6/1997 | Kurtz et al. |
| 5,641,799 A | 6/1997 | Kurtz et al. |
| 5,641,811 A | 6/1997 | Kurtz et al. |
| 5,641,812 A | 6/1997 | Kurtz et al. |
| 5,643,894 A | 7/1997 | Kurtz et al. |
| 5,643,941 A | 7/1997 | Kurtz et al. |
| 5,643,945 A | 7/1997 | Kurtz et al. |

(Continued)

FOREIGN PATENT DOCUMENTS

| | | |
|---|---|---|
| CN | 1768732 A | 5/2006 |
| CN | 1768733 A | 5/2006 |
| CN | 101190211 A | 6/2008 |
| DE | 10 2005 023 834 A1 | 5/2006 |
| EP | 841924 | 5/1998 |
| EP | 1 082 416 B1 | 3/2001 |
| EP | 1127052 | 8/2001 |
| EP | 1 348 432 A1 | 10/2003 |
| EP | 1 500 643 A1 | 1/2005 |
| FR | 2 456 731 A | 12/1980 |

(Continued)

OTHER PUBLICATIONS

Santomauro et al. "Overnight Lowering of Free Fatty Acids With Acipimox Improves Insulin Resistance and Glucose Tolerance in Obese Diabetic and Nondiabetic Subjects" Diabetes vol. 48, Sep. 1999 pp. 1836-1841.*

(Continued)

*Primary Examiner* — Herbert J. Lilling
(74) *Attorney, Agent, or Firm* — Morrison & Foerster LLP

(57) ABSTRACT

The present invention relates to a method of treating a fatty acid synthesis related disease comprising administering to a patient in need thereof an effective amount of a PARP inhibitor or metabolite thereof to inhibit fatty acid synthesis, wherein the fatty acid synthesis related disease is obesity, diabetes, or cardiovascular disease. The present invention also relates to a method of treating a cancer in a subject comprising: (i) identifying a level of fatty acid in a sample from the subject, and (ii) administering an effective amount of a PARP inhibitor or metabolite thereof to inhibit fatty acid synthesis in the subject, wherein the administration is based on the level of fatty acid, thereby treating the cancer in the subject. The present invention further relates to a method of treating Her-2 related cancers by administering to a patient in need thereof an effective amount of a PARP inhibitor or metabolite thereof to inhibit fatty acid synthesis.

12 Claims, 11 Drawing Sheets

U.S. PATENT DOCUMENTS

| | | |
|---|---|---|
| 5,643,955 A | 7/1997 | Kurtz et al. |
| 5,643,956 A | 7/1997 | Kurtz et al. |
| 5,646,122 A | 7/1997 | Kurtz et al. |
| 5,650,403 A | 7/1997 | Kurtz et al. |
| 5,652,260 A | 7/1997 | Kun et al. |
| 5,652,367 A | 7/1997 | Kun et al. |
| 5,654,311 A | 8/1997 | Kurtz et al. |
| 5,665,755 A | 9/1997 | Kurtz et al. |
| 5,670,518 A | 9/1997 | Kun et al. |
| 5,700,792 A | 12/1997 | Kurtz et al. |
| 5,703,053 A | 12/1997 | Kurtz et al. |
| 5,719,151 A | 2/1998 | Shall et al. |
| 5,734,056 A | 3/1998 | Burk et al. |
| 5,736,576 A | 4/1998 | Kun et al. |
| 5,753,674 A | 5/1998 | Kun et al. |
| 5,756,510 A | 5/1998 | Griffin et al. |
| 5,770,599 A | 6/1998 | Gibson |
| 5,783,599 A | 7/1998 | Kun et al. |
| 5,837,729 A | 11/1998 | Bourinbaiar |
| 5,866,608 A | 2/1999 | Kurtz et al. |
| 5,874,444 A | 2/1999 | West |
| 5,877,185 A | 3/1999 | Kun et al. |
| 5,908,861 A | 6/1999 | Kun |
| 5,922,775 A | 7/1999 | Kun et al. |
| 5,959,133 A | 9/1999 | Ohnishi |
| 5,981,575 A * | 11/1999 | Kuhajda et al. ............... 514/473 |
| 6,004,978 A | 12/1999 | Kun et al. |
| 6,008,250 A | 12/1999 | Kurtz et al. |
| 6,015,792 A | 1/2000 | Kurtz et al. |
| 6,015,827 A | 1/2000 | Griffin et al. |
| 6,017,958 A | 1/2000 | Kun et al. |
| 6,100,283 A | 8/2000 | Griffin et al. |
| 6,121,278 A | 9/2000 | Jackson et al. |
| 6,156,739 A | 12/2000 | Griffin et al. |
| 6,169,104 B1 | 1/2001 | Tuse et al. |
| 6,201,020 B1 | 3/2001 | Zhang et al. |
| 6,235,748 B1 | 5/2001 | Li et al. |
| 6,277,990 B1 | 8/2001 | Jagtap et al. |
| 6,303,629 B1 | 10/2001 | Kun |
| 6,310,082 B1 | 10/2001 | Griffin et al. |
| 6,316,455 B1 | 11/2001 | Griffin et al. |
| 6,316,495 B1 | 11/2001 | Kun et al. |
| 6,326,517 B1 | 12/2001 | Kume et al. |
| 6,380,193 B1 | 4/2002 | Li et al. |
| 6,387,902 B1 | 5/2002 | Zhang et al. |
| 6,395,749 B1 | 5/2002 | Li et al. |
| 6,407,079 B1 | 6/2002 | Müller et al. |
| 6,423,696 B1 | 7/2002 | Collins et al. |
| 6,426,415 B1 | 7/2002 | Jackson et al. |
| 6,476,048 B1 | 11/2002 | Szabo et al. |
| 6,495,541 B1 | 12/2002 | Webber et al. |
| 6,514,983 B1 | 2/2003 | Li et al. |
| 6,531,491 B1 | 3/2003 | Kania et al. |
| 6,548,494 B1 | 4/2003 | Webber et al. |
| 6,653,316 B1 | 11/2003 | South et al. |
| 6,664,269 B2 | 12/2003 | Martin et al. |
| 6,677,333 B1 | 1/2004 | Seko et al. |
| 6,723,733 B2 | 4/2004 | Li et al. |
| 6,903,098 B1 | 6/2005 | Lubisch et al. |
| 6,924,284 B2 | 8/2005 | Beaton et al. |
| 6,989,388 B2 | 1/2006 | Pellicciari et al. |
| 7,179,484 B2 | 2/2007 | Singh |
| RE39,608 E | 5/2007 | Lubisch et |
| 2002/0028815 A1 | 3/2002 | Ator et al. |
| 2002/0142334 A1 | 10/2002 | Brown et al. |
| 2002/0156050 A1 | 10/2002 | Li et al. |
| 2002/0164633 A1 | 11/2002 | Szabo et al. |
| 2004/0034078 A1 | 2/2004 | Skalitzky et al. |
| 2004/0077667 A1 | 4/2004 | Matsuoka et al. |
| 2004/0198693 A1 | 10/2004 | DeNinno et al. |
| 2004/0248879 A1 | 12/2004 | Canan-Koch et al. |
| 2004/0249841 A1 | 12/2004 | Cameron et al. |
| 2005/0004038 A1 | 1/2005 | Lyon et al. |
| 2005/0020595 A1 | 1/2005 | Kalish et al. |
| 2005/0026933 A1 | 2/2005 | Greenberger et al. |
| 2005/0054631 A1 | 3/2005 | Jiang et al. |
| 2005/0059824 A1 | 3/2005 | Vaidyanathan et al. |
| 2005/0080096 A1 | 4/2005 | Ishida et al. |
| 2005/0113283 A1 | 5/2005 | Solow-Cordero et al. |
| 2005/0142621 A1 | 6/2005 | Thompson et al. |
| 2005/0171036 A1 | 8/2005 | Arakawa et al. |
| 2005/0171101 A1 | 8/2005 | Yamamoto et al. |
| 2005/0182040 A1 | 8/2005 | Imazaki et al. |
| 2005/0227919 A1 | 10/2005 | Ashworth et al. |
| 2005/0287120 A1 | 12/2005 | Fisher et al. |
| 2006/0063767 A1 | 3/2006 | Javaid et al. |
| 2006/0074073 A1 | 4/2006 | Steinfeldt et al. |
| 2006/0084650 A1 | 4/2006 | Dong et al. |
| 2006/0094676 A1 | 5/2006 | Lahav et al. |
| 2006/0100198 A1 | 5/2006 | Liu et al. |
| 2006/0204981 A1 | 9/2006 | Li et al. |
| 2006/0229289 A1 | 10/2006 | Zhu et al. |
| 2006/0229351 A1 | 10/2006 | Zhu et al. |
| 2007/0015814 A1 | 1/2007 | Kun et al. |
| 2007/0015837 A1 | 1/2007 | Kun et al. |
| 2007/0265324 A1 | 11/2007 | Wernet et al. |
| 2007/0281948 A1 | 12/2007 | Peukert et al. |
| 2007/0292883 A1 | 12/2007 | Ossovskaya et al. |
| 2008/0025990 A1 | 1/2008 | Ludwig |
| 2008/0039633 A1 | 2/2008 | Jung et al. |
| 2008/0076737 A1 | 3/2008 | Ossovskaya et al. |
| 2008/0076778 A1 | 3/2008 | Ossovskaya et al. |
| 2008/0103104 A1 | 5/2008 | Moore et al. |
| 2008/0167345 A1 | 7/2008 | Jones et al. |
| 2008/0171786 A1 | 7/2008 | Bruggemeier et al. |
| 2008/0176946 A1 | 7/2008 | Ossovskaya et al. |
| 2008/0262062 A1 | 10/2008 | Ossovskaya et al. |
| 2008/0293795 A1 | 11/2008 | Donawho et al. |
| 2008/0319054 A1 | 12/2008 | Kun et al. |
| 2009/0076122 A1 | 3/2009 | Kun et al. |
| 2009/0123419 A1 | 5/2009 | Sherman et al. |
| 2009/0131529 A1 | 5/2009 | Sherman et al. |
| 2009/0149397 A1 | 6/2009 | Ossovskaya et al. |
| 2009/0149417 A1 | 6/2009 | Ossovskaya et al. |
| 2009/0275608 A1 | 11/2009 | Ossovskaya et al. |
| 2009/0291924 A1 | 11/2009 | Ossovskaya et al. |
| 2010/0003192 A1 | 1/2010 | Sherman et al. |
| 2010/0009930 A1 | 1/2010 | Sherman et al. |
| 2010/0160442 A1 | 6/2010 | Ossovskaya et al. |

FOREIGN PATENT DOCUMENTS

| | | |
|---|---|---|
| GB | 1 463 575 | 2/1977 |
| GB | 2 447 796 B | 9/2008 |
| JP | 2000/191612 A | 7/2000 |
| JP | 2005/336083 A | 12/2005 |
| WO | WO-91/18591 A1 | 12/1991 |
| WO | WO-92/06687 A1 | 4/1992 |
| WO | WO-94/05664 A1 | 3/1994 |
| WO | WO-94/10202 A1 | 5/1994 |
| WO | WO-94/26730 A2 | 11/1994 |
| WO | WO-94/26730 A3 | 11/1994 |
| WO | WO 94/27584 | 12/1994 |
| WO | WO-96/22791 A1 | 8/1996 |
| WO | WO-96/40210 A1 | 12/1996 |
| WO | WO-97/34593 A1 | 9/1997 |
| WO | WO-98/45253 A1 | 10/1998 |
| WO | WO-98/51307 A1 | 11/1998 |
| WO | WO-99/11624 A1 | 3/1999 |
| WO | WO 99/11628 A1 | 3/1999 |
| WO | WO-01/04086 A1 | 1/2001 |
| WO | WO-02/49992 A2 | 6/2002 |
| WO | WO-02/49992 A3 | 6/2002 |
| WO | WO-03/007955 A2 | 1/2003 |
| WO | WO-03/007955 A3 | 1/2003 |
| WO | WO-03/062392 A2 | 7/2003 |
| WO | WO-03/062392 A3 | 7/2003 |
| WO | WO 2005/012305 A2 | 2/2005 |
| WO | WO 2005/012305 A3 | 4/2005 |
| WO | WO-2005/054201 A1 | 6/2005 |
| WO | WO-2005/054209 A1 | 6/2005 |
| WO | WO-2005/054210 A1 | 6/2005 |
| WO | WO-2005/058843 A1 | 6/2005 |
| WO | WO-2005/058843 C1 | 6/2005 |
| WO | WO-2005/097750 A1 | 10/2005 |
| WO | WO-2006/003146 A1 | 1/2006 |
| WO | WO-2006/003147 A1 | 1/2006 |
| WO | WO-2006/003148 A1 | 1/2006 |

| WO | WO-2006/003150 A1 | 1/2006 |
| WO | WO-2006/020681 A2 | 2/2006 |
| WO | WO-2006/020681 A3 | 2/2006 |
| WO | WO-2006/033006 A2 | 3/2006 |
| WO | WO-2006/033006 A3 | 3/2006 |
| WO | WO-2006/046735 A1 | 5/2006 |
| WO | WO-2006/067472 A1 | 6/2006 |
| WO | WO-2007/011962 A2 | 1/2007 |
| WO | WO-2007/011962 A3 | 1/2007 |
| WO | WO-2007/107305 A2 | 9/2007 |
| WO | WO-2007/107305 A3 | 9/2007 |
| WO | WO-2008/030883 A2 | 3/2008 |
| WO | WO-2008/030883 A3 | 3/2008 |
| WO | WO-2008/030891 A2 | 3/2008 |
| WO | WO-2008/030891 A3 | 3/2008 |
| WO | WO-2008/089272 A1 | 7/2008 |
| WO | WO-2008/107478 A1 | 9/2008 |
| WO | WO-2008/147418 A1 | 12/2008 |
| WO | WO-2009/064444 A2 | 5/2009 |
| WO | WO-2009/064738 A2 | 5/2009 |
| WO | WO-2009/073869 A1 | 6/2009 |
| WO | WO-2009/100159 A2 | 8/2009 |
| WO | WO-2009/100159 A3 | 8/2009 |
| WO | WO-2010/091140 A1 | 8/2010 |

OTHER PUBLICATIONS

Andersen, et al. The effect of glucose on the potency of two distinct glycogen phosphorylase inhibitors. Biochem. J. 2002; 367:443-450.

Boros, et al. Metabolic profiling of cell growth and death in cancer: applications in drug discovery. Drug Discov. Today. 2002; 7:364-372.

Comin-Andutx, et al. The effect of thiamine supplementation on tumour proliferation. A metabolic control analysis study, Eur J. Biochem. 2001; 268:4177-4182.

Kuhijda, et al. Synthesis and antitumor activity of an inhibitor of fatty acid synthase, Proc Natl. Acad Sci. 2000; 97(7):3450-3454.

Kuhijda, et al. Fatty acid synthesis: a potential selective target for antineoplastic therapy. Proc. Natl. Acad. Sci. 1994; 91:6379-6383.

Lee, et al. Fatty acid cycling in human hepatoma cells and the effects of troglitazone, J. Biol. Chem. 1998; 273; 20929-20934.

Lee, et al. Mass isotopomer study of glutamine oxidation and synthesis in primary culture of astrocytes. Developmental Neuroscience. 1996; 18:469-477.

Lee, et al. Mass isotopomer study of the nonoxidative pathways of the pentose cycle with [1,2-13C2]glucose. Am J. Physiol. 1998; 274:E843-E851.

Leimer, et al. Complete mass spectra of N-trifluoroacetyl-n-butyl esters of amino acids. Journal of Chromatography. 1977; 141: 121-144.

Loftus, et al, Reduced food intake and body weight in mice treated with fatty acid synthase inhibitors. Science. 2000; 288:2379-2381.

Menedez, et al. Does endogenous fatty acid metabolism allow cancer cells to sense hypoxia and mediate hypoxic vasodilatation? Characterization of a novel molecular connection between fatty acid synthase (FAS) and hypoxia-inducible factor-1alpha (HIF-1alpha)-related expression of vascular endothelial growth factor (VEGF) in cancer cells overexpressing her-2/neu oncogene. J. Cell. Biochem. 2005; 94(5): 857-863.

Menedez, et al. Targeting fatty acid synthase: potential for therapeutic intervention in her-2/neu-overexpressing breast cancer. Drug new Perspect. 2005; 18(6):375-385.

Pizer, et al. Inhibition of fatty acid synthesis induces programmed cell death in human breast cancer cells. Cancer Res. 1996; 56:2745-2747.

Rice, et al. Induction of Endonuclease-Mediated Apoptosis in Tumor Cells by C-Nitroso—Substituted Ligands of Poly(ADP-Ribose) Polymerase. Proceedings of the National Academy of Sciences. 1992; 89:7703-7707.

Sabate, et al. A model of the pentose phosphate pathway in rat liver cells. Mol Cell. Biochem. 1995; 142:9-17.

Moore, et al, U.S. Appl. No. 60/842,474, entitled "Treatment of Cancer" filed Sep. 5, 2006.

Ossovskaya, et al. U.S. Appl. No. 60/804,563, entitled "Method of Treating Diseases with PARP Inhibitors" filed Jun. 12, 2006.

Aachmann, F. L. et al. (2003). "Structural Background of Cyclodextrin-Protein Interactions," Prot. Eng. 16(12):905-912.

Arnold, N. et al. (May 1996). "Overrepresentation of 3q and 8q Material and Loss of 18q Material are Recurrent Findings in Advanced Human Ovarian Cancer," Genes Chromosomes Cancer 16(1):46-54.

Arnone, C. et al. (Apr. 18, 1997). Nucleophilic Substitution Reactions of 1-Halogeno-4-COR-2- Nitrobenzenes and 1-Halogen-6-COR-2 Nitrobenzenes with Sodium Benzenethiolate and Piperidine. Can an Inverted Built-In Solvation' be Responsible for the Peculiar Activation by an o-Carboxamido Group in $S_nAr$ Reactions With an Anionic Nucleophile? J. Org. Chem. 62(10):3093-3097.

Astrazeneca International. (2004). "Gefitinib (IRESSA™) Lung Cancer ISEL Trial shows no overall survival advantage in a highly refractory population," Press release, Dec. 17, 2004, located at http://www.astrazeneca.com/pressrelease/4245.aspx, last visited Oct. 2, 2009, 3 pages.

Audebert, M. et al. (Dec. 31, 2004)."Involvement of Poly(ADP-Ribose) Polymerase-1 and XRCC1/DNA Ligase III in an Alternative Route for DNA Double-Strand Breaks Rejoining," J. Biol. Chem. 279(53):55117-55126 (Epub Oct. 21, 2004).

Ayhan, A. et al. (2006). "Topotecan as a Second-Line Therapy in Patients With Ovarian and Primary Peritoneal Cancer: Initial Response and Long-Term Follow-Up," Eur. J. Gynecol Oncol. 27(6):603-606.

Bale, A. E. et al. (1997). "The Nevoid Basal Cell Carcinoma Syndrome: Genetics and Mechanism of Carcinogenesis," Cancer Invest. 15(2):180-186.

Ball, H. G. et al. (Aug. 1996). "A Phase II Trial of Paclitaxel in Patients With Advanced or Recurrent Adenocarcinoma of the Endometrium: A Gynecologic Oncology Group Study," Gynecol. Oncol. 62(2):278-281.

Banasik, M. et al. (Jan. 25, 1992). "Specific Inhibitors of Poly(ADP-Ribose) Synthetase and Mono(ADP-Ribosyl)Transferase," J. Biol. Chem. 267(3):1569-1575.

Bangham, A. D. et al. (1965). "Diffusion of Univalent Tons Across the Lamellae of Swollen Phosholipids," J. Mol. Biol. 13:238-252.

Banker, G. S. et al. eds. (1996). Modern Pharmaceutics, Marcel Dekker, New York, 3$^{rd}$ edition, pp. 596-597 and Table of Content (with last page of the book).

Bauer, P. I. et al. (2002). "Anti-Cancer Action of 4-Iodo-3-Introbenzamide in Combination With Buthionine Sulfoximine: Inactivation of Poly(ADP-Ribose) Polymerase and Tumor Glycolysis and the Appearance of a Poly(ADP-Ribose) Polymerase Protease," Biochem. Pharmacol. 63(3):455-462.

Bauer, P. I. et al. (2005). "The Influence of ATP on Poly(ADP-Ribose) Metabolism," Int'l J. Mol. Med. 16:321-324.

Bello, M. J. et al. (Jan. 15, 1990). "Chromosome Aberrations in Metastatic Ovarian Cancer: Relationship With Abnormalities in Primary Tumors," Int. J. Cancer 45(1):50-54.

Ben-Hur, E. et al. (1984). "Inhibitors of Poly (ADP-Ribose) Synthesis Enhance Radiation Response by Differentially Affecting Repair of Potentially Lethal Versus Sublethal Damage," Br. J. Cancer 49(Supl. 6):39-42.

Bentle, M. S. et al. (2006). "New Tricks for Old Drugs: the Anticarcinogenic Potential of DNA Repair Inhibitors," J. Mol. Histol. 37(5-7):203-218.

Berchuck, A. et al. (Jan. 1991). "Overexpression of HER-2/Neu in Endometrial Cancer is Associated With Advanced Stage Disease," Am. J. Obstet. Gynecol. 164(1 Pt. 1):15-21.

Berger, N. A. (Jan. 1985). "Poly(ADP-Ribose) in the Cellular Response to DNA Damage," Radiation Research 101:4-15.

Berkow, R. ed. (Aug. 1987). "Chapter 105. Oncology—Treatment and Prognosis," in The Merck Manual of Diagnosis and Therapy, 15th ed. Merck & Co., Inc., pp. 1218-1225 and Table of Contents.

Bhattacharjee, A. et al. (Nov. 20, 2001). "Classification of Human Lung Carcinomas by mRNA Expression Profiling Reveals Distinct Adenocarcinoma Subclasses," Proc. Nat'l. Acad. Sci. USA 98(24):13790-13795. (Epub. Nov. 13, 2001).

Bigler, L. R. et al. (Sep.-Oct. 2004). "Evaluation of Tamoxifen in Persistent or Recurrent Nonsquamous Cell Carcinoma of the Cervix: a Gynecologic Oncology Group Study," Int. J. Gynecol. Cancer. 14(5):871-874.

Bonadonna, G. et al. (Jan. 1998). "Primary Chemotherapy in Operable Breast Cancer: Eight-Year Experience at the Milan Cancer Institute," *J. Clin. Oncol.* 16(1):93-100.

Borczuk, A. C. et al. (Nov. 2003). "Non-Small-Cell Lung Cancer Molecular Signatures Recapitulate Lung Development Pathways," *Am. J. Pathol.* 163(5):1949-1960.

Bouchard, V. et al. (Jun. 2003). "PARP-1, a Determinant of Cell Survival in Response to DNA Damage," *Exp. Hematol.* 31(6):446-454.

Bowman, K. J. et al. (Jan. 5, 2001). "Differential Effects of the Poly(ADP-Ribose) Polymerase (PARP) Inhibitor NU1025 on Topoisomerase I and II Inhibitor Cytotoxicity in L1210 Cells in Vitro," *Br. J. Cancer* 84(1):106-112.

Bryant, H. E. et al. (Apr. 14, 2005). "Specific Killing of BRCA2-Deficient Tumours with Inhibitors of Poly(ADP-Ribose) Polymerase," *Nature* 434(7035):913-917, and *Erratum in Nature* (May 17, 2007) 447(7142):346.

Buki, K. G. et al. (Sep. 1991). "Destabilization of $Zn^{2+}$ Coordination in ADP-Ribose Transferase (Polymerizing) by 6-Nitroso-1,2-Benzopyrone Coincidental With Inactivation of the Polymerase but not the DNA Binding Function," *FEBS Lett.* 290(1/2):181-185.

Buki, K.G. et al. (1992). "Inactivation of the Polymerase but not the DNA Binding Function of ADPRT by Destabilization of one of its $Zn^{2+}$ Coordination Centers by 6-Nitroso-1,2-Benzopryone," in *ADP-Ribosylation Reactions*, Poirier, G. G. et al., eds., Springer-Verlag, New York, NY, pp. 329-333.

CANCER.ORG (2005). "What is Ovarian Cancer?" available online as of Feb. 5, 2005 as evidenced by the attached Internet Archive Report located at http://www.cancer.org/docroot/CRI/content/CRI_2_4_1X_What_is_ovarian_cancer_33.asp, 6 pages total.

Chang, J.-W. et al. (May 2000). "Correlation of Genetic Instability With Mismatch Repair Protein Expression and *P53* Mutations in Non-Small Cell Lung Cancer," *Clin. Cancer Res.* 6(5):1639-1646.

Chang, P. et al. (Dec. 2, 2004). "Poly(ADP-ribose) is Required for Spindle Assembly and Structure," *Nature* 432(7017):645-649.

Chen, Q.-R. et al. (Feb. 2007). "Diagnosis of the Small Round Blue Cell Tumors Using Multiplex Polymerase Chain Reaction," *J. Mol. Diagnostics* 9(1):80-88.

Chen, X. (1998). "Potential for Selective Modulation of Glutathione in Cancer Chemotherapy," *Chem. Biol. Interact.* 111-112:263-275.

Chevallier, B. et al. (Jun. 1993). "Inflammatory Breast Cancer. Pilot Study of Intensive Chemotherapy (FEC-HD) Results in a High Histologic Response Rate," *Am. J. Clin. Oncol.* 16(3):223-228.

Chin, K. et al. (Dec. 2006). "Genomic and Transcriptional Aberrations Linked to Breast Cancer Pathophysiologies," *Cancer Cell* 10(6)529-541.

Christie, M. et al. (Jun. 2006). "Molecular Pathology of Epithelial Ovarian," *J. Br. Menopause Soc.* 12(2):57-63.

Chu, S. et al. (Aug. 24, 2007). "Poly(ADP-Ribose) Polymerase-1 Regulates Vimentin Expression in Lung Cancer Cells," *Am. J. Physiol.: Lung, Cell. Mol. Physiol.* 293:L1127-L1134.

Chuang, A. J. et al. (1994). "Comparison of the Cytotoxic and Antiretroviral Effects of 3-Nitrosobenzamide and 4-Iodo-3-Nitrobenzamide," *Proc. West. Pharmacol. Soc.* 37:117-119.

Chustecka, Z. (Jan. 22, 2007). "Adding Bevacizumab Not Beneficial in Pancreatic Cancer," *Gastrointestinal Cancers Symposium*, presented Jan. 20, 2007, 2 pages.

Clarke, M. J. (Oct. 8, 2008). Early Breast Cancer Trialists' Collaborative Group. "Tamoxifen for Early Breast Cancer," from the *Cochrane Database of Systematic Reviews* Oct. 8, 2008, (4):CD000486. This abstract was available at http://www.cochrane.org/reviews/en/ab000486.html, but is now withdrawn from the Cochrane Database System Review. This abstract was an updated version of Cochrane Database System Review (2001)(1):CD000486, abstract available in PubMed at http://www.ncbi.nlm.nih.gov/pubmed/18843611?ordinalpos=5&itool=EntrezSystem2.PEntrez.Pubmed.Pubmed_ResultsPanel.Pubmed_DefaultReportPanel.Pubmed_RVDocSum, last visited Oct. 2, 2009, 2 pages.

Classen, S. et al. (Sep. 16, 2003). "Structure of the Topoisomerase II ATPase Region and its Mechanism of Inhibition by the Chemotherapeutic Agent ICRF-187," *Proc. Nat'l. Acad. Sci. USA* 100(19):10629-10634, including Erratum published on Nov. 25, 2003, *Proc. Nat'l. Acad. Sci. USA* 100(24):14510-14511.

Cleator, S. et al. (Mar. 2007). "Triple-Negative Breast Cancer: Therapeutic Options," *Lancet Oncol.* 8:235-244.

Clinical Trials. US Government (2008). Evaluation of Paclitaxel (Taxol, NSC #673089), Carboplatin (Paraplatin, NSC #241240), and BSI-201 (NSC #746045, IND #71,677) in the Treatment of Advanced, Persistent, or Recurrent Uterine Carcinosarcoma, Verified by BiPar Sciences, Jul. 2009, first received: May 28, 2008, last updated: Jul. 23, 2009, located at http://clinicaltrials.gov/ct2/show/NCT00687687, last visited on Sep. 18, 2009, 4 pages.

Comen, E. A. et al. (May 20, 2008). "Prevalence of *BRCA1* and *BRCA2* Mutations in Jewish Women with Triple Negative Breast Cancer," 44th Annual Meeting of the American Society of Clinical Oncology, May 30-Jun. 3, 2008, Chicago, IL, a supplement to the *J. Clin. Oncol.* 26(15S):749s, Abstract 22002, which can be located at http://www.jco.ascopubs.org/cgi/mgca..., last visited on Jun. 14, 2009, eight pages total.

Cosi, C. et al. (1994). "Poly(ADP-Ribose) Polymerase: Early Involvement in Glutamate-Induced Neurotoxicity in Cultured Cerebellar Granule Cells," *J. Neurosci. Res.* 39:38-46.

Cosi, C. et al. (2002). "New Inhibitors of Poly(ADP-Ribose) Polymerase and Their Therapeutic Targets," *Exp. Opin. Therapeut. Pat.* 12(7):1047-1071.

Costantino, G. et al. (2001). "Modeling of Poly(ADP-Ribose)Polymerase (PARP) Inhibitors. Docking of Ligands and Quantitative Structure-Activity Relationship Analysis," *J. Med. Chem.* 44(23): 3786-3794 (ePUB Oct. 13, 2008).

Crowson, M. C. et al. (Dec. 1986). "A Phase II Study to Evaluate Tamoxifen in Pancreatic Adenocarcinoma," *Eur. J. Surg. Oncol.* 12(4):335-336.

Curtin, J. P. et al. (Nov. 2001). "Paclitaxel in the Treatment of Carcinosarcoma of the Uterus: A Gynecologic Oncology Group Study," *Gynecol. Oncology* 83(2):268-270.

D'Adda Di Fagagna, F. et al. (Sep. 1999). "Functions of Poly(ADP-Ribose) Polymerase in Controlling Telomere Length and Chromosomal Stability," *Nature Genetics* 23(1):76-80.

D'Amours, D. et al. (Sep. 1, 1999). "Poly (ADP-Ribosyl)ation Reactions in the Regulation of Nuclear Functions," *Biochem J.* 342(Part 2):249-268.

Deger, R. B. et al. (Jul. 15, 1997). "Karyotic Analysis of 32 Malignant Epithelial Ovarian Tumors," *Cancer Genet. Cytogenet.* 96(2):166-173.

Delaney, C. A. et al. (Jul. 2000). "Potentiation of Temozolomide and Topotecan Growth Inhibition and Cytotoxicity by Novel Poly(Adenosine Diphosphoribose) Polymerase Inhibitors in a Panel of Human Tumor Cell Lines," *Clin. Cancer Res.* 6(7):2860-2867.

Delattre, O. et al. (Sep. 10, 1992). "Gene Fusion With an *ETS* DNA-Binding Domain Caused by Chromosome Translocation in Human Tumours," *Nature* 359(6391):162-165.

Delattre, O. et al. (Aug. 4, 1994). "The Ewing Family of Tumors—A Subgroup of Small-Round-Cell Tumors Defined by Specific Chimeric Transcripts," *N. Engl. J. Med.* 331(5):294-299.

De Murcia, G. et al. (Apr. 1994). "Poly(ADP-Ribose) Polymerase: a Molecular Nick-Sensor," *Trends in Biochemical Sciences* 19:172-176.

Dent, R. et al. (Aug. 1, 2007). "Triple-Negative Breast Cancer: Clinical Features and Patterns of Recurrence," *Clin. Cancer Res.* 13(15 Pt 1):4429-4434.

Desmarais, Y. et al. (Jun. 24, 1991). "Enzymological Properties of Poly(ADP-Ribose)Polymerase: Characterization of Automodification Sites and NADase Activity," *Biochim. Biophys. Acta.* 1078(2):179-186.

De Soto, J. A. et al. (Jul. 15, 2006). "PARP-1 Inhibitors: Are They the Long-Sought Genetically Specific Drugs for BRCA1/2-Associated Breast Cancers?" *Int. J. Med. Sci.* 3(4):1 17-123.

De Soto, J. et al. (2006). "The Inhibition and Treatment of Breast Cancer with Poly (ADP-Ribose) Polymerase (PARP-1) Inhibitors," *Int. J. Biol. Sci.* 2(4):179-185.

Diebold, J. et al. (Apr. 2000). "20q13 and Cyclin D1 in Ovarian Carcinomas. Analysis by Fluorescence in Situ Hybridization," *J. Pathol.* 190(5):564-571.

Donawho, C. K. et al. (May 1, 2007). "ABT-888, an Orally Active Poly(ADP-Ribose) Polymerase Inhibitor that Potentiates DNA-Damaging Agents in Preclinical Tumor Models," *Clin. Cancer Res.* 13(19):2728-2737.

Donawho, C. K. et al. (2008). "The PARP Inhibitor, ABT-888 Overcomes Resistance in Temozolomide-Refractory Prostate and Breast Xenograft Tumors Implanted in Metastatic Sites In Vivo," Meeting Poster No. 555 (one page), and Palma, J. et al. (Oct. 24, 2008). "The PARP Inhibitor, ABT-888 Overcomes Resistance in Temozolomide-Refractory Prostate and Breast Xenograft Tumors Implanted in Metastatic Sites In Vivo," $20^{th}$ *EORTC-NCI-AACR, Symposium on Molecular Targets and Cancer Therapeutics, European Journal of Cancer* Supplements 6(12):175, poster No. 555.

Donegan, W. L. et al., eds., (1988). *Cancer of the Breast*, $3^{rd}$ Edition, W. B. Saunders: Philadelphia, PA, in Chapter 17 entitled Endocrine Therapy of Breast Cancer, by C. G. Cardinal, pp. 504-506.

Dongiovanni, D. et al. (2008). "Gefitinib (ZD 1839): Therapy in Selected Patients With Non-Small Cell Lung Cancer (NSCLC)?" *Lung Cancer* Feb. 1, 2008 [EPUB ahead of print] located at http://www.ncbi.nlm.nih.gov/pubmed/18243402, last visited Oct. 2, 2009, 2 pages.

Dracopoli, N. C. et al. (Aug. 1, 1987). "Loss of Heterozygosity at Autosomal and X-Linked Loci During Tumor Progression in a Patient With Melanoma," *Cancer Res.* 47(15):3995-4000.

Drew, Y. et al. (Sep. 2008). "The Potential of PARP Inhibitors in Genetic Breast and Ovarian Cancers," *Ann. N.Y. Acad. Sci.* 1138:136-145.

Duell, E. J. et al. (Aug. 15, 2002). "A Population-Based Study of the *Arg399Gln* Polymorphism in X-Ray Repair Cross-Complementing Group 1 (*XRCC1*) and Risk of Pancreatic Adenocarcinoma," *Cancer Res.* 62:4630-4636.

Durkacz, B. W. et al. (Feb. 7, 1980). "(ADP-Ribose)$_n$ Participates in DNA Excision Repair," *Nature* 283:593-596.

Edwards, S. L. et al. (Feb. 28, 2008). "Resistance to Therapy Caused by Intragenic Deletion in *BRCA2*," *Nature* 451(7182):1111-1115, with one additional page "Methods".

El-Khaminsy, S. F. et al. (Oct. 2003). "A Requirement for PARP-1 for the Assembly or Stability of XRCC1 Nuclear Foci at Sites of Oxidative DNA Damage," *Nucleic Acid Res.* 31(19):5526-5533.

Ellis, M. K. et al. (Apr. 15, 1992). "Reactions of Nitrosonitrobenzenes with Biological Thiols: Identification and Reactivity of Glutathion-S-yl Conjugates," *Chem. Biol. Interactions* 82(2):151-163.

Erowid. (Jan. 2001). "Introduction to the Federal Controlled Substance Analogue Act," located at http://www.erowid.org/psychoactives/law/analog/analog_info 1.shtml., last visited Oct. 13, 2006, total of 4 pages.

Eyer, P. et al. (1980). "Biotransformation of Nitrosobenzene in the Red Cell and the Role of Glutathione," *Xenobiotica* 10(7/8):517-526.

Farmer, H. et al. (Apr. 14, 2005). "Targeting the DNA Repair Defect in *BRCA* Mutant Cells as a Therapeutic Strategy," *Nature* 434(7035):917-921.

Fedier, A. et al. (May 2003). "The Effect of Loss of BRCA1 on the Sensitivity to Anticancer Agents in p53-Deficient Cells," *Int. J. Oncol.* 22(5):1169-1173, Abstract only located in PubMed.

Fierce Biotech. (2006). "Avastin encounters rare failure for pancreatic cancer," Fierce Biotech Web site, Jun. 26, 2006, located at http://www.fiercebiotech.com/story/avastin-encounters-rare-failure-for-pancreatic-cancer/2006-06-27, last visited Oct. 2, 2008, 1 page.

Filmus, J. et al. (Jan. 1987). "Epidermal Growth Factor Receptor Gene-Amplified MDA-468 Breast Cancer Cell Line and its Nonamplified Variants," *Mol. Cell. Biol.* 7(1):251-257.

Fisher, B. et al. (Apr. 6, 1994). "Endometrial Cancer in Tamoxifen-Treated Breast Cancer Patients: Findings From the National Surgical Adjuvant Breast and Bowel Project (NSABP) B-14," *J. Nat'l. Cancer Inst.* 86(7):527-537.

Fisher, B. et al. (Jul. 1997). "Effect of Preoperative Chemotherapy on Local-Regional Disease in Women With Operable Breast Cancer: Findings From the National Surgical Adjuvant Breast and Bowel Project B-18," *J. Clin. Oncol.* 15(7):2483-2493.

Fisher, B. et al. (Aug. 1998). "Effect of Preoperative Chemotherapy on the Outcome of Women With Operable Breast Cancer," *J. Clin. Oncol.* 16(8):2672-2685.

Flemming, G. F. (Jun. 1, 2004). "Phase III Trial of Doxorubicin plus Cisplatin With or Without Paclitaxel Plus Filgrastim in Advanced Endometrial Carcinoma: A Gynecologic Oncology Group Study," *J. Clin. Oncol.* 22(11):2159-2166.

Flemming, G. F. et al. (Aug. 2004). "Phase III Randomized Trial of Doxorubicin + Cisplatin Versus Doxorubicin + 24-h Paclitaxel + Filgrastim in Endometrial Carcinoma, A Gynecologic Oncology Group Study," *Ann. Oncol.* 15(8):1173-1178.

Fletcher, J. A. et al. (Mar. 1991). "Ovarian Granulosa-Stromal Cell Tumors Are Characterized by Trisomy 12," *Am. J. Pathol.* 138(3):515-520.

Fojo, A. T. et al. (Nov. 1985). "Amplification of DNA Sequences in Human Multidrug—Resistant KB Carcinoma Cells," *Proc. Nat'l. Acad. Sci. USA* 82(22):7661-7665.

Fong, P. C. et al. (2006). "Phase I Pharmacokinetic (PK) and Pharmacodynamic (PD) Evaluation of a Small Molecule Inhibitor of Poly ADP-Ribose Polymerase (PARP), KU-0059436 (Ku) in Patients (p) With Advanced Tumours," *Supplement to Journal of Clinical Oncology, 2006 ASCO Annual Meeting Proceedings*, Part I. vol. 24, No. 18S, Part I of II, (Jun. 20, 2006), p. 126s, abstract No. 3022.

Gäken, J. O. et al. (Jun. 1996). "Efficient Retroviral Infection of Mammalian Cells is Blocked by Inhibition of Poly(ADP-Ribose) Polymerase Activity," *Journal of Virology* 70(6):3992-4000.

Gallion, H. H. et al. (Sep. 1990). "Chromosome Abnormalities in Human Epithelial Ovarian Malignancies," *Gynecol. Oncol.* 38(3):473-477.

Garber, M. E. et al. (Nov. 20, 2001). "Diversity of Gene Expression in Adenocarcinoma of the Lung," *Proc. Nat'l. Acad. Sci. USA* 98(24):13784-13789. (EPUB Nov. 13, 2001) and Erratum in *Proc. Nat'l. Acad. Sci. USA* (Jan. 22, 2002). 99(2):1098.

Garber, J. E. et al. (Dec. 14-17, 2006). "Neo-Adjuvant Cisplatin (CDDP) in 'Triple-Negative' Breast Cancer (BC)," *Breast Cancer Research and Treatment, Special Issue, $29^{th}$ San Antonio Breast Cancer Symposium 2006*; vol. 100, Poster Session III, p. S149, Abstract No. 3074.

Goldstein, J. (Feb. 13, 2008). "Latest Avastin Breast Cancer Study Unlikely to Sway FDA," *The Wall Street Journal* located at http://blogs.wsj.com/health/2008/02/13/latest-avastin-breast-cancer-study-unlikely-to-sway-fda/, last visited on Feb. 15, 2008, 3 pages total.

Gradwohl, G. et al. (Apr. 1990). "The Second Zinc-Finger Domain of Poly(ADP-Ribose) Polymerase Determines Specificity for Single-Stranded Breaks in DNA," *Proc. Nat'l. Acad. Sci. USA* 87:2990-2994.

Greenfacts.org. Definition of Solid Cancer, located at http://222.greenfacts.org/glossary/pqrs/solid-cancer.htm, last visited Jul. 18, 2009, one page total.

Griffin, R. J. et al. (Sep. 1995). "Novel Potent Inhibitors of the DNA Repair Enzyme Poly(ADP-Ribose)Polymerase (PARP)," *Anticancer Drug Design* 10(6):507-514.

Griffin, R. J. et al. (Jan. 10, 1996). "Novel Benzimidazole and Quinazolinone Inhibitors of the DNA Repair Enzyme Poly(ADP-Ribose)Polymerase," *Pharmaceutical Sciences* 2(1):43-47.

Griffin, R. J. et al. (1998). Resistance-Modifying Agents. 5. Synthesis and Biological Properties of Quinazolinone Inhibitors of the DNA Repair Enzyme Poly(ADP-Ribose) Polymerase (PARP). *J. Med. Chem.* 41(26):5247-5256.

Gudmundsdottir, K. et al. (Sep. 25, 2006). "The Roles of BRCA1 and BRCA2 and Associated Proteins in the Maintenance of Genomic Stability," *Oncogene* 25(43):5864-5874.

Gurpide, E. (Mar. 20, 1991). "Endometrial Cancer: Biochemical and Clinical Correlates," *J. Nat'l. Cancer Inst.* 83(6):405-416.

Hakam, A. et al. (Feb. 1987). "Catalytic Activities of Synthetic Octadeoxyribonucleotides as Coenzymes of Poly(ADP-Ribose) Polymerase and the Identification of a New Enzyme Inhibitory Site," *FEBS Lett.* 212(1):73-78.

Harris, N. L. et al. (Dec. 1999). "World Health Organization Classification of Neoplastic Diseases of the Hematopoietic and Lymphoid Tissues: Report of the Clinical Advisory Committee Meeting-Airlie House, Virginia, Nov. 1997," *J. Clin. Oncol.* 17(12)3835-3849.

Hassa, P. O. et al. (Dec. 7, 2001). "The Enzymatic and DNA Binding Activity of PARP-1 Are Not Required for NF-kB Coactivator Function," *J. Biol. Chem.* 276(49):45588-45597.

Hassa, P. O. et al. (Sep. 2006). "Nuclear ADP-Ribosylation Reactions in Mammalian Cells: Where Are We Today and Where Are We Going?" *Microbiol. Mol. Biol. Rev.* 70(3):789-829.

Hegi, M. E. et al. (Mar. 10, 2005). "MGMT Gene Silencing and Benefit From Temozolomide in Glioblastoma," *N. Engl. J. Med.* 352(10):997-1003.

Heighway, J. et al. (Oct. 31, 2002). "Expression Profiling of Primary Non-Small Cell Lung Cancer for Target Identification," *Oncogene* 21(50):7749-7763.

Helleday, T. et al. (Mar. 2008). "DNA Repair Pathways as Targets for Cancer Therapy," *Nat. Rev. Cancer*. 8(3):193-204.

Hellström, I. et al. (Mar. 15, 2001). "Overexpression of HER-2 in Ovarian Carcinomas," *Cancer Res.* 61(6):2420-2423.

Henderson, L. E. et al. (Aug. 25, 1981). "Primary Structure of the Low Molecular Weight Nucleic Acid-binding Proteins of Murine Leukemia Viruses," *J. Biol. Chem.* 256(16):8400-8403.

Herceg, Z. et al. (Jun. 2, 2001). "Functions of Poly(ADP-Ribose) Polymerase (PARP) in DNA Repair, Genomic Integrity and Cell Death," *Mutat. Res.* 477(1-2):97-110.

Herzog, T. J. (2002). "Update on the Role of Topotecan in the Treatment of Recurrent Ovarian Cancer," *Oncologist* 7(suppl. 5):3-10.

Hickman, J. A. (Sep. 1975). "Protection Against the Effects of the Antitumour Agent CB 1954 by Certain Imidazoles and Related Compounds," *Biochem. Pharmacol.* 24(17):1947-1952.

Higashi, T. et al. (1983). "Retrospects and Prospects," *Glutathione: Storage, Transport and Turnover in Mammals*, eds., Sakamoto, Y. et al. Japan Sci. Soc. Press, Tokyo,/VNU Science Press, Utrecht, pp. 3-9.

Hod, Y. (Dec. 1992). "A Simplified Ribonuclease Protection Assay," *Biotechniques* 13(6):852-853.

Höglund, M. et al. (Jun. 15, 2003). "Ovarian Carcinoma Develops Through Multiple Modes of Chromosomal Evolution," *Cancer Res.* 63(12):3378-3385.

Homesley, H. D. et al. (Feb. 10, 2007). "Phase III Trial of Ifosfamide With or Without Paclitaxel in Advanced Uterine Carcinosarcoma: A Gynecologic Oncology Group Study," *J. Clin. Oncol.* 25(5):526-531.

Honkoop, A. H. et al. (1998). "Prognostic Role of Clinical, Pathological and Biological Characteristics in Patients with Locally Advanced Breast Cancer," *Br. J. Cancer* 77(4):621-626.

Hubert, A. et al. (Aug.-Sep. 2004). "PARP-1, PARP-2 and ATM in the DNA Damage Response: Functional Synergy in Mouse Development," *DNA Repair (Amst)* 3(8-9):1103-1108.

Hwang, S. J. et al. (Aug. 2003). "Lung Cancer Risk in Germline p53 Mutation Carriers: Association Between an Inherited Cancer Predisposition, Cigarette Smoking, and Cancer Risk," *Hum. Genet.* 113(3):238-243 (Epub. Jun. 11, 2003).

Irvin, J. W. Jr. et al. (Dec. 2008). "What is Triple-Negative Breast Cancer?" *Eur. J. Cancer* 44(18):2799-2805.

Ishii, D. et al. (Aug. 2007). "Efficacy of Temozolomide is Correlated with 1p Loss and Methylation of the Deoxyribonucleic Acid Repair Gene MGMT in Malignant Gliomas," *Neurol. Med. Chir. (Tokyo)* 47(8):341-350.

Iwabuchi, H. et al. (Dec. 15, 1995). "Genetic Analysis of Benign, Low-Grade, and High-Grade Ovarian Tumors," *Cancer Res.* 55(24):6172-6180.

Jaboin, J. et al. (Nov. 1, 2002). "MS 27-275, an Inhibitor of Histone Deacetylase, Has Marked In Vitro and In Vivo Antitumor Activity Against Pediatric Solid Tumors," *Cancer Res.* 62:6108-6115.

Jacob, D. A. et al. (2007). "Combination Therapy of Poly (ADP-Ribose) Polymerase Inhibitor 3-Aminobenzamide and Gemcitabine Shows Strong Antitumor Activity in Pancreatic Cancer Cells," *J. Gastroenterol. Hepatol.* 22:738-748.

Jagtap, P. et al. (2002). "Novel Phenanthridinone Inhibitors of Poly (Adenosine 5'-Diphosphate-Ribose) Synthetase: Potent Cytoprotective and Antishock Agents," *Crit. Care Med.* 30(5):1071-1082.

Jagtap, P. et al. (May 2005). "Poly(ADP-Ribose) Polymerase and the Therapeutic Effects of its Inhibitors," *Nature Rev. Drug Disc.* 4:421-440.

Jemal, A. et al. (Jan./Feb. 2003). "Cancer Statistics 2003," *CA Cancer J. Clin.* 53(1):5-26.

Jenkins, R. B. et al. (Nov. 1993). "Cytogenetic Studies of Epithelial Ovarian Carcinoma," *Cancer Genet. Cytogenet.* 71(1):76-86.

Jeon, I. S. et al. (Mar. 16, 1995). "A Varian Ewing's Sarcoma Translocation (7;22) Fuses the *EWS* Gene to the ETS Gene *ETV1*," *Oncogene* 10(6):1229-1234.

Jones, C. et al. (Oct. 2008). "PARP Inhibitors and Cancer Therapy— Early Results and Potential Applications," *Br. J. Radiol.* 81 Spec No. 1:S2-S5.

Kandel, M. J. et al. (2006). "Prevalence of BRCA1 Mutations in Triple Negative Breast Cancer (BC)," *2006 ASCO Annual Meeting, Supplemental to the Journal of Clinical Oncology*, Jun. 20, 2006, Part I, vol. 24, No. 18S, abstract No. 508.

Karczewski, J. M. et al. (1999). "Prevention of Oxidant-Induced Cell Death in Caco-2 Colon Carcinoma Cells after Inhibition of Poly(ADP-Ribose) Polymerase and $Ca^{2+}$ Chelation: Involvement of a Common Mechanism," *Biochem. Pharmacol.* 57:19-26.

Kerley-Hamilton, J. S. et al. (Sep. 8, 2005). "A p53-Dominant Transcriptional Response to Cisplatin in Testicular Gene Cell Tumor-Derived Human Embyronal Carcinoma," *Oncogene* 24(40):6090-6110.

Khalid, M. N. et al. (Apr. 2006). "Long Circulating Poly(Ethylene Glycol)-Decorated Lipid Nanocapsules Deliver Docetaxel to Solid Tumors," *Pharm. Res.* 23(4):752-758.

Kiechle, M. et al. (Feb. 1, 2001). "Comparative Genomic Hybridization Detects Genetic Imbalances in Primary Ovarian Carcinomas as Correlated With Grade of Differentiation," *Cancer* 91(3):534-540.

Kiechle-Schwarz, M. et al. (Nov. 1994). "Recurrent Cytogenetic Aberrations and Loss of Constitutional Heterozygosity in Ovarian Carcinomas," *Gynecol. Oncol.* 55(2):198-205.

Kim, M. Y. et al. (Dec. 17, 2004). "$NAD^+$-Dependent Modulation of Chromatin Structure and Transcription by Nucleosome Binding Properties of PARP-1," *Cell* 119(6):803-814.

Kindler, H. L. (2007). "A Double-Blind, Placebo-Controlled, Randomized Phase III Trial of Gemcitabine (G) Plus Bevacizumab (B) Versus Gemcitabine plus Placebo (P) in Patients (pts) with Advanced Pancreatic Cancer (PC): A Preliminary Analysis of Cancer and Leukemia Group B (CALGB) 80303," *Gastrointestintal Cancers Symposium: Mutidisciplinary Approaches to the Prevention, Diagnosis, and Therapy of GI Cancers*, Jan. 19-21, 2007, Orlando, Florida, p. 319, abstract 108.

Kirsten, E. et al. (2000). "Cancer Cell Selectivity of 5-lodo-6-Aminobenzopyrone (INH2BP) and Methyl 3-5-Diiodo-4(4'-Methoxyphenol) Benzoate (DIME)," *Int'l J. Mol. Med.* 5(3):279-281.

Kiyohara, C. et al. (Sep. 2002). "Genetic Polymorphisms and Lung Cancer Susceptibility: A Review," *Lung Cancer* 37(3):241-256.

Ko, A. H. (Feb. 17, 2003). "Cancer of the Pancreas," published by *Cancer Supportive Care Programs*, article located at http://www.cancersupportivecare.com/pancreas/html, last visited on Sep. 23, 2009, 5 pages total.

Kosower, E. M. (1976). "Chemical Properties of Glutathione," Chapter 1 in *Glutathione Metabolism and Function*, Arias, M. et al., eds., Raven Press: New York, NY, Kroc Foundation Series, vol. 6, pp. 1-15.

Kuerer, H. M. et al. (Jul./Aug. 1998). "Pathologic Tumor Response in the Breast Following Neoadjuvant Chemotherapy Predicts Axillary Lymph Node Status," *Cancer J. Sci. Am.* 4(4):230-236.

Kuerer, H. M. et al. (Feb. 1999). "Clinical Course of Breast Cancer Patients With Complete Pathologic Primary Tumour and Axillary Lymph Node Response to Doxorubicin-Based Neoadjuvant Chemotherapy," *J. Clin. Oncol.* 17(2):460-469.

Kume, K. et al. (2005). "Mutations in the Serine Protease Inhibitor Kazal Type 1 (*SPINK1*) Gene in Japanese Patients with Pancreatitis," *Pancreatology* 5:354-360.

Kun, E. et al. (1983). "Biochemical Basis of the Regulatory Role of Polyadenosine Diiphosphoribose," *Advances in Enzyme Regulation* 21:177-199.

Kun, E. et al. (Mar.-Jun. 2001). "Cell Biological Functions of PARP-1: An Overview," *Ital. J. Biochem.* 50(1-2):15-18.

Kun, E. et al. (2003). "Synergistic Anticancer Action of Reversibly and Irreversibly Acting Ligands of Poly (ADP-Ribose) Polymerase," *Int'l J. Mol. Med.* 11(2):191-193.

Kun, E. et al. (2006). "Quantitative Correlation Between Cellular Proliferation and Nuclear Poly (ADP-Ribose) Polymerase (PARP-1)," *Int'l J. Mol. Med.* 17:293-300.

Lau, A. et al. (Oct. 21-24, 2008). "Pre-Clinical Activity of the PARP Inhibitor Olaparib (AZD2281) in Homologous Recombination Repair Deficient Triple Negative Breast Cancer," Poster at *20th EORTC-NCI-AACR Symposium on "Molecular Targets and Cancer Therapeutics,"* Oct. 21-24, 2008, Geneva, Switzerland, two pages.

Lee, W.-N. et al. (Mar. 20, 1995). "Isotopomer Study of Lipogenesis in Human Hepatoma Cells in Culture: Contribution of Carbon and Hydrogen Atoms from Glucose," *Anal. Biochem.* 226(1):100-112.

Lee-Jones, L. (Aug. 2003). "Ovary: Germ Cell Tumors," *Atlas of Genetics and Cytogenetics in Oncology and Haematology*, pp. 591-605, located at http://atlasgeneticsoncology.org/Tumors/OvarianGermCellID5067.pdf, last visited on Sep. 25, 2009, 15 pages total.

Lee-Jones, L. (Nov. 2003). "Ovary: Sex Cord-Stromal Tumors," *Atlas of Genetics and Cytogenetics in Oncology and Haematology*, 8(1):125-131, located at http://AtlasGeneticsOncology.org/Tumors/OvarSexCordStromID5223.html, last visited on Sep. 25, 2009, 15 pages total.

Lee-Jones, L. (Dec. 2003). "Ovary: Epithelial Tumors," *Atlas Genet Cytogenet Oncol Haematol* 8(2):256-306, located at http://atlasgeneticsoncology.org/Tumors/OvaryEpithTumID5230.pdf, 51 pages total.

Leslie, K. K. et al. (2005). "Tyrosine Kinase Inhibitors in Endometrial Cancer," *Int. J. Gynecol. Cancer* 15:409-411, abstract No. 0020.

Lev, D. C. et al. (Aug. 2003). "Dacarbazine Causes Transcriptional up-Regulation of Interleukin 8 and Vascular Endothelial Growth Factor in Melanoma Cells; A Possible Escape Mechanism From Chemotherapy," *Mol. Cancer Therap.* 2(8):753-763.

Lever, A. et al. (Sep. 1989). "Identification of a Sequence Required for Efficient Packaging of Human Immunodeficiency Virus Type 1 RNA into Virions," *J. Virol.* 63(9):4085-4087.

Lewis, G. D. et al. (Sep. 1993). "Differential Responses of Human Tumor Cell Lines to Anti-p185$^{HER2}$ Monoclonal Antibodies," *Cancer Immunol. Immunother.* 37(4):255-263.

Li, D. et al. (Mar. 27, 2004). "Pancreatic Cancer," *The Lancet* 363:1049-1057.

Li, J.-H. et al. (2001). "Synthesis of Substituted 5[*H*]phenanthridin-6-ones as Potent Poly(ADP-Ribose)Polymerase-1 (PARP1) Inhibitors," *Bioorg. Med. Chem. Lett.* 11:1687-1690.

Loesch, D. M. (Dec. 8-11, 2005). "Phase II Trial of Gemcitabine Plus Carboplatin (plus Trastuzumab in HER-2 Positive Patients) in Metastatic Breast Cancer Patients," *Breast Cancer Research and Treatment, Special Issue 28th annual San Antonio Breast Cancer Symposium 2005*, San Antonio, Texas, vol. 94, Supplement 1, p. S280, Poster Session VI, Abstract No. 6092.

Marchesi, F. et al. (Oct. 2007). "Triazene Compounds: Mechanism of Action and Related DNA Repair Systems," *Pharmacol. Res.* 56(4):275-287.

Marsit, C. J. et al. (Jan. 29, 2004). "Inactivation of the Fanconi Anemia/BRCA Pathway in Lung and Oral Cancers: Implications for Treatment and Survival," *Oncogene* 23(4):1000-1004.

Masson, M. et al. (Jun. 1998). "XRCC1 is Specifically Associated With Poly(ADP-Ribose) Polymerase and Negatively Regulates its Activity Following DNA Damage," *Mol. Cell Biol.* 18(6):3563-3571.

Masutani, M. et al. (Dec. 2003). "Poly(ADP-Ribose) and Carcinogenesis," *Genes, Chromosomes, and Cancer* 38(4):339-348.

Mayr, D. et al. (Sep. 2002). "Characteristic Pattern of Genetic Aberrations in Ovarian Granulosa Cell Tumors," *Mod. Pathol.* 15(9):951-957.

Mazzon, E. et al. (Mar. 2001). "GPI 6150, a Poly (ADP-Ribose) Polymerase Inhibitor, Exhibits an Anti-Inflammatory Effect in Rat Models of Inflammation," *Eur. J. Pharmacol.* 415(1):85-94.

McCabe, N. et al. (Aug. 15, 2006). "Deficiency in the Repair of DNA Damage by Homologous Recombination and Sensitivity to Poly(ADP-ribose) Polymerase Inhibition," *Cancer Res.* 66(16):8109-8115.

McCluggage, W. G. (May 2002). "Malignant Biphasic Uterine Tumors: Carcinosarcomas or Metaplastic Carcinomas?" *J. Clin. Pathol.* 55(5):321-325.

McLaughlin, P. et al. (Aug. 1998). "Rituximab Chimeric Anti-CD20 Monoclonal Antibody Therapy for Relapsed Indolent Lymphoma: Half of Patients Respond to a Four-Dose Treatment Program," *J. Clin. Oncol.* 16(8):2825-2833.

Mendeleyev, J. et al. (Aug. 25, 1995). "Potential Chemotherapeutic Activity of 4-Iodo-3-Nitrobenzamide. Metabolic Reduction to the 3-Ntroso Derivative and Induction of Cell Death in Tumor Cells in Culture," *Biochem Pharmacol.* 50(5):705-714.

Ménissier De Murcia, J. et al. (Jul. 8, 1997). "Requirement of Poly(ADP-Ribose) Polymerase in Recovery From DNA Damage in Mice and in Cells," *Proc. Nat'l. Acad. Sci. USA* 94(14):7303-7307.

Meric, C. et al. (Apr. 1989). "Characterization of Moloney Murine Leukemia Virus Mutants with Single-Amino-Acid Substitutions in the Cys-His Box of the Nucleocapsid Protein," *J. Virol.* 63(4):1558-1568.

Miller, D. S. et al. (Aug. 2005). "Phase II Evaluation of Topotecan in Carcinosarcoma of the Uterus: A Gynecologic Oncology Group Study," *Gynecol. Oncol.* 98(2):217-221.

Mitsuuchi, Y. et al. (Oct. 30, 2002). "Cytogenetics and Molecular Genetics of Lung Cancer," *Am. J. Med. Genet.* 115(3):183-188.

Mrózek, K. et al. (Mar. 1990). "Trisomy of Chromosome 12 in a Case of Thecoma of the Ovary," *Gynecol. Oncol.* 36(3):413-416.

Mugneret, F. et al. (Jun. 1988). "Chromosomes in Ewing's Sarcoma. II. Nonrandom Additional Changes, Trisomy 8 and der(16)t(1;16)," *Cancer Genet. Cytogenet.* 32(2):239-245.

Nahleh, Z. et al. (Nov. 2007). "Trastuzumab not for Ductal Carcinoma in Situ?" *Anticancer Drugs* 18(10):1231-1235.

Nahta, R. et al. (May 2006). "Mechanisms of Disease: Understanding Resistance to HER2-Targeted Therapy in Human Breast Cancer," *Nat. Clin. Pract. Oncol.* 3(5):269-280.

Narod, S. A. et al. (Sep. 2004). "*BRCA1* and *BRCA2*: 1994 and Beyond," *Nat. Rev. Cancer* 4(9):665-676.

National Cancer Institute. (2005). "Bevacizumab Combined With Chemotherapy Improves Progression-Free Survival for Patients With Advanced Breast Cancer," U.S. National Institutes of Health, available at: http://www.cancer.gov/newscenter/pressreleases/AvastinBreast, last visited Oct. 2, 2009, 2 pages, also *Ther.* 4(8):1239.

Nguewa, P. A. et al. (2003). "Pharmacological Modulation of Poly(ADP-Ribose) Polymerase-Mediated Cell Death: Exploitation in Cancer Chemotherapy," *Mol. Pharmacol.* 64(5):1007-1014.

Nitta, K. at al. (Mar. 1987). "Antitumor Activity of New Derivatives of Camptothecin," *Gan To Kagaku Ryoho.* 14(3 Pt 2):850-857. This article is in Japanese with English abstract on p. 857.

Nomura, F. et al. (May 2000). "Enhancement of Poly-Adenosine Diphosphate-Ribosylation in Human Hepatocellular Carcinoma," *J. Gastroenterol. Hepatol.* 15(5):529-535.

O'Brien, J. et al. (2000). "Investigation of the Alamar Blue (Resazurin) Fluorescent Dye for the Assessment of Mammalian Cell Cytotoxicity," *Eur. J. Biochem. FEBS* 267(17):5421-5426.

Ogston, K. N. et al. (2003). "A New Histological Grading System to Assess Response of Breast Cancers to Primary Chemotherapy: Prognostic Significance and Survival," *Breast* 12:320-327.

Okano, S. et al. (Jun. 2003). "Spatial and Temporal Cellular Responses to Single-Strand Breaks in Human Cells," *Mol. Cell Biol.* 23(11): 3974-3981.

Olver, I. N. (Feb. 2008). "Trastuzumab as the Lead Monoclonal Antibody in Advanced Breast Cancer: Choosing Which Patient and When," *Future Oncol.* 4(1):125-131.

Omura, G. A. et al. (Aug. 15, 1983). "A Randomized Study of Adriamycin With and Without Dimethyl Triazenoimidazole Carboxamide in Advanced Uterine Sarcomas," *Cancer* 52(4):626-632.

Oosting-Lenstra, S. F. et al. (Dec. 2007). "Failure of Chop with Rituximab for Lymphomatoid Granulomatosis," *Neth. J. Med.* 65(11):442-447.

(OSI)™ Pharmaceuticals, (Aug. 9, 2005). "Tarceva® (Erlotinib) Tablets NDA 21-743, S003, Supplemental NDA: Pancreatic Cancer, Briefing Document, ODAC Meeting Sep. 13, 2005," PDF located at http://www.fda.gov/ohrms/dockets/AC/05/briefing/2005-4174B1_03_01-OSI-Tarceva.pdf, 66 pages total, last visited Sep. 25, 2009.

Paez, J. G. et al. (Jun. 4, 2004). "*EGFR* Mutations in Lung Cancer: Correlation With Clinical Response to Gefitinib Therapy," *Science* 304(5676):1497-1500.

Palmer, B. D. et al. (Jul. 8, 1994). "Hypoxia-Selective Antitumor Agents. 9. Structure-Activity Relationships for Hypoxia-Selective Cytotoxicity Among Analogues of 5-[*N,N*-bis(2-Chloroethyl)Amino]-2,4-Dinitrobenzamide," *J. Med. Chem.* 37(14):2175-2184.

Pao, W. et al. (Sep. 7, 2004). "EGF Receptor Gene Mutations are Common in Lung Cancers From 'Never Smokers' and are Associated With Sensitivity of Tumors to Gefitinib and Erlotinib," *Proc. Nat'l. Acad. Sci. USA* 101(36):13306-13311.

Park, C. et al. (2005). "Induction of Apoptosis and Inhibition of Cycloosygenase-2 Expression by *N*-Methyl-*N*-Nitro-*N*-Nitrosoguanidine in Human Leukemia Cells," *Anti-Cancer Drugs* 16(5):507-513.

Parker, R. M. C. et al. (1999). "mRNA: Detection by in Situ and Northern Hybridization," *Methods in Molecular Biology, Chapter 14*, 106:247-283.

Pedersen, M. I. et al. (Feb. 1, 1986). "Nonrandom Chromosome Structural Aberrations and Oncogene Loci in Human Malignant Melanoma," *Cancer Genet. Cytogenet.* 20(1-2):11-27.

Pejovic, T. et al. (May 1990). "Trisomy 12 is a Consistent Chromosomal Aberration in Benign Ovarian Tumors," *Genes Chromosomes Cancer* 2(1):48-52.

Pejovic, T. et al. (Jan. 1992). "Chromosome Aberrations in 35 Primary Ovarian Carcinomas," *Genes Chromosomes Cancer* 4(1):58-68.

Pejovic, T. et al. (Feb. 1995). "Genetic Changes in Ovarian Cancer," *Ann. Med.* 27(1):73-78.

Perkins, E. et al. (May 15, 2001). "Novel Inhibitors of Poly(ADP-Ribose) Polymerase/PARP1 and PARP2 Identified Using a Cell-Based Screen in Yeast," *Cancer Res.* 61:4175-4183.

Plummer, R. et al. (2005). "First in Human Phase I Trial of the PARP Inhibitor AG-014699 With Temozolomide (TMZ) in Patients (pts) With Advanced Solid Tumors,"2005 41$^{st}$ Annual Meeting of the American Society of Clinical Oncology, May 13-17, 2005, Orlando Florida, 2005 Annual Meeting Proceedings Part I, (a supplement to the Journal of Clinical Oncology, vol. 23, No. 16S, Part I of II (Jun. 1 Supplement), p. 208s, abstract No. 3065.

Plummer, R. et al. (2006)."First and Final Report of a Phase II Study of the Poly(ADP-Ribose) Polymerase (PARP) Inhibitor, AG014699, in Combination With Temozolomide (TMZ) in Patients With Metastatic Malignant Melanoma (MM)," 2006 42$^{nd}$ Annual Meeting of the American Society of Clinical Oncology, Jun. 2-6, 2006, Atlanta, GA, Supplement to the *J. Clin. Oncol*. Part I of II, vol. 24, No. 18S (Jun. 20, 2006) p. 456s, abstract No. 8013.

Porta, M. et al. (Dec. 18/25, 1999). "Serum Concentrations of Organochlorine Compounds and K-*ras* Mutations in Exocrine Pancreatic Cancer," from the Pankras II Study Group, *The Lancet* 354:2125-2129.

Powell, S. N. et al. (Sep. 1, 2003). "Roles of BRCA1 and BRCA2 in Homologous Recombination, DNA Replication Fidelity and the Cellular Response in Ionizing Radiation," *Oncogene* 22(37):5784-5791.

Powles, T. J. et al. (Mar. 1995). "Randomized Trial of Chemoendocrine Therapy Started Before or After Surgery for Treatment of Primary Breast Cancer," *J. Clin. Oncol.* 13(3):547-552.

Ramonas, K. et al. (2005). "Treatment of Transgenic Murine Retinoblastoma With 4-lodo-3-Nitrobenzamide (INO$_2$BA), a Novel Chemotherapeutic Agent," *Invest. Ophthalmol. Vis. Sci.* 46(5):E-Abstract 3422-B975, 2 pages total, also located at http://abstracts.iovs.org/cgi/content/abstract/46/5/3422, 2 pages.

Ratnam, K. et al. (Mar. 1, 2007). "Current Development of Clinical Inhibitors of Poly(ADP-Ribose) Polymerase in Oncology," *Clin. Cancer Res.* 13(5):1383-1388.

Rattan, S. I. et al. (Jun. 15, 1994). "Kinetin Delays the Onset of Ageing Characteristics in Human Fibroblasts," *Biochem. Biophys. Res. Comm*. 201(2):665-672.

Razzak, A. R. et al. (2008). "Heterogeneity of Breast Cancer and Implications of Adjuvant Chemotherapy," *Breast Cancer* 15(1):31-34.

Reis-Filho, J. S. et al. (2008). "Triple Negative Tumours: a Critical Review," *Histopathol.* 52:108-118.

Richmond, A. et al. (Mar. 1986). "Growth Factor and Cytogenetic Abnormalities in Cultured Nevi and Malignant Melanomas," *J. Invest. Dermatol*. 86(3):295-302.

Ries, L. A. G. et al. (eds). (2007) SEER Cancer Statistics Review, 1975-2004, National Cancer Institute. Bethesda, MD, based on Nov. 2006 SEER data submission, posted to the SEER web site, 2007, located at http://seer.cancer.gov/csr/1975_2004/, 3 pages.

Roberts, C. G. et al. (Sep. 1990). "Cytogenetic Study of Solid Ovarian Tumors," *Cancer Genet. Cytogenet*. 48(2):243-253.

Roche—Media News. (2006). "US Phase III Study of Avastin in Advanced Pancreatic Cancer Does Not Meet Primary Endpoint," Basel, Jun. 27, 2006, Roche Web site, located at http://www.roche.com/investors/ir_update/inv-update-2006-06-27.htm, last visited Oct. 2, 2009, 2 pages.

Rottenberg, S. et al. (Nov. 4, 2008). "High Sensitivity of BRCA1-Deficient Mammary Tumors to the PARP Inhibitor AZD2281 Alone and in Combination With Platinum Drugs," *Proc. Nat'l. Acad. Sci. USA* 105(44):17079-17084.

Ruscetti, T. et al. (Jun. 5, 1998). "Stimulation of the DNA-Dependent Protein Kinase by Polv(ADP-Ribose) Polymerase," *J. Biol. Chem.* 273(23):14461-14467.

Said, S. I. et al. (May 1996). "Excitotoxicity in the Lung: *N*-Methyl-D-Aspartate-Induced, Nitric Oxide-Dependent, Pulmonary Edema is Attenuated by Vasoactive Intestinal Peptide and by Inhibitors of Poly(ADP-Ribose) Polymerase," *Proc. Natl. Acad. Sci. USA* 93:4688-4692.

Saito, A. et al. (Apr. 1999). "A Synthetic Inhibitor of Histone Deacetylase, MS-27-275, With Marked in vivo Antitumor Activity Against Human Tumors," *Proc. Nat'l Acad. Sci. USA* 96:4592-4597.

Sakai, W. et al. (Feb. 28, 2008). "Secondary Mutations as a Mechanism of Cisplatin Resistance in BRCA2-Mutated Cancers," *Nature* 451:1116-1121.

Sataloff, D. M. et al. (Mar. 1995). "Pathologic Response to Induction Chemotherapy in Locally Advanced Carcinoma of the Breast: a Determinant of Outcome," *J. Am. Coll. Surg*. 180(3):297-306.

Schlicker, A. et al. (Jan. 1, 1999). "4-Amino-1,8-Naphthalimide: a Novel Inhibitor of Poly(ADP-Ribose) Polymerase and Radiation Sensitizer," *Int. J. Radiat. Biol*. 75(1):91-100.

Schreiber, V. et al. (Jul. 2006). "Poly(ADP-ribose): Novel Functions for an Old Molecule," *Nat. Rev. Mol. Cell Biol*.7(7):517-528.

Seracchioli, R. et al. (Jun. 2001). "Conservative Treatment of Recurrent Ovarian Fibromas in a Young Patient Affected by Gorlin Syndrome," *Hum. Reprod*. 16(6):1261-1263.

Serra, V. et al. (Oct. 1, 2008). "NVP-BEZ235, a Dual PI3K/mTOR Inhibitor, Prevents PI3K Signaling and Inhibits the Growth of Cancer Cells with Activating PI3K Mutations," *Cancer Res*. 68(19):8022-8030.

Shah, Y. M. et al. (2005). "Selenium Disrupts Estrogen Receptor α Signaling and Potentiates Tamoxifen Antagonism in Endometrial Cancer Cells and Tamoxifen-Resistant Breast Cancer Cells," *Mol Cancer Ther*. 4(8):1239-1249.

Shall, S. et al. (May 11, 1999). "Preparation of Aminobenzamides and Related Compounds as Inhibitors of Poly(ADP-Ribose)-Metabolizing Enzymes," *Chemical Abstracts* 116(19):193929e.

Shall, S. et al. (Jun. 30, 2000). "Poly(ADP-Ribose) Polymerase-1: What Have We Learned From the Deficient Mouse Model?" *Mutat Res*. 460(1):1-15.

Shaw, E. et al. (1998). "Practice Parameters in Adults With Suspected or Known Supratentorial Nonoptic Pathway Low-Grade Glioma," *Neurosurg. Focus.* From American Association of Neurological Surgeons, 4(6), Article 10, 11 pages total.

Shen, D.-W. et al. (Jun. 15, 1986). "Multiple Drug-Resistant Human KB Carcinoma Cells Independently Selected for High-Level Resistance to Colchicine, Adriamycin, or Vinblastine Show Changes in Expression of Specific Proteins," *J. Biol. Chem*. 261(17):7762-7770.

Silverberg, S. G. et al. (1991). "Carcinomas," in Tumors of the Uterine Corpus and Gestational Trophoblastic Disease, Atlas of Tumor Pathology, in 3$^{rd}$ Series, Fascicule 3, Washington D. C., Armed Forces Institute of Pathology, pp. 166-179.

Simbulan-Rosenthal, C. M. et al. (Oct. 10, 2000). "Misregulation of Gene Expression in Primary Fibroblasts Lacking Poly(ADP-Ribose) Polymerase," *Proc. Nat'l Acad. Sci. USA* 97(21):11274-11279.

Simbulan-Rosenthal, C. M. et al. (Nov. 20, 2003). "PARP-1 Binds E2F-1 Independently of its DNA Binding and Catalytic Domains, and Acts as a Novel Coactivator of E2F-1-Mediated Transcription During Re-Entry of Quiescent Cells into S Phase," *Oncogene* 22(52):8460-8471.

Simon, R. (Mar. 1989). "Optimal Two-Stage Designs for Phase II Clinical Trials," *Control Clin. Trials* 10(1):1-10.

Simonin, F. et al. (Jun. 25, 1993). "The Carboxyl-Terminal Domain of Human Poly(ADP-Ribose) Polymerase. Overproduction in *Escherichia coli*, Large Scale Purification and Characterization," *J. Biol. Chem.* 268(18):13454-13461.

Singh, N. (Jun. 14, 1991). "Enhanced Poly ADP-Ribosylation in Human Leukemia Lymphocytes and Ovarian Cancers," *Cancer Lett.* 58(1-2):131-135.

Slayton, R. E. et al. (Jun. 1987). "Phase II Trial of Etoposide in the Management of Advanced or Recurrent Mixed Mesodermal Sarcomas of the Uterus: A Gynecologic Oncology Group Study," *Cancer Treatment Reports* 71(6):661-662.

Sonoda, G. et al. (Dec. 1997). "Comparative Genomic Hybridization Detects Frequent Overrepresentation of Chromosomal Material From 3q26, 8q24, and 20q13 in Human Ovarian Carcinomas," *Genes Chromosomes Cancer* 20(4):320-328.

Soriano, F. G. et al. (Jan. 2001). "Diabetic Endothelial Dysfunction: The Role of Poly(ADP-Ribose) Polymerase Activation," *Nature Medicine* 7(1):108-113.

Sorlie, T. et al. (Jul. 8, 2003). "Repeated Observation of Breast Tumor Subtypes in Independent Gene Expression Data Sets," *Proc. Nat'l. Acad. Sci. USA* 100(14):8418-8423. Epub Jun. 26, 2003.

Stephenson, C. F. et al. (Nov. 1992). "Cytogenetic and Pathologic Aspects of Ewing's Sarcoma and Neuroectodermal Tumors," *Hum. Pathol.* 23(11):1270-1277.

Stryer, L. (1981). *Biochemistry*, Second Edition, W.H. Freeman and Company: San Francisco, CA, Part II, Chapter 15 entitled "Pentose Phosphate Pathway and Glucogenesis," pp. 343-345.

Sutton, G. P. et al. (Aug. 1989). "Phase II Trial of Ifosfamide and Mesna in Mixed Mesodermal Tumors of the Uterus, (A Gynecologic Oncology Group Study)," *Am. J. Obstet. Gynecol.* 161 (2):309-312.

Sutton, G. et al. (Nov. 2000). "A Phase III Trial of Ifosfamide With or Without Cisplatin in Carcinosarcoma of the Uterus, A Gynecologic Oncology Group Study," *Gynecol. Oncol.* 79(2):147-153.

Suzuki, S. et al. (Oct. 1, 2000). "An Approach to Analysis of Large-Scale Correlations Between Genome Changes and Clinical Endpoints in Ovarian Cancer," *Cancer Research* 60(19):5382-5385.

Szabó, C. et al. (Jun. 1997). "Regulation of Components of the Inflammatory Response by 5-Iodo-6-Amino-1,2Benzopyrone, an Inhibitor of Poly(ADP-Ribose) Synthetase and Pleiotropic Modifier of Cellular Signal Pathways," *Int. J. Oncol.* 10(6)1093-1101.

Szoka, F. et al. (Sep. 1978). "Procedure for Preparation of Liposomes With Large Internal Aqueous Space and High Capture by Reverse-Phase Evaporation," *Proc. Nat'l Acad. Sci. USA* 75(9):4194-4198.

Taetle, R. et al. (Jul. 1999). "Chromosome Abnormalities Adenocarcinoma: I. Nonrandom Chromosome Abnormalities from 244 Cases," *Genes Chromosomes Cancer* 25(3):290-300.

Tanner, M. M. et al. (May 2000). "Frequent Amplification of Chromosomal Region 20q12-q13 in Ovarian Cancer," *Clin. Cancer Res.* 6(5):1833-1839.

Taruscio, D. et al. (Jun. 1993). "Detection of Trisomy 12 on Ovarian Sex Cord Stromal Tumors by Fluorescence in Situ Hybridization," *Diagn. Mol. Pathol.* 2(2):94-98.

Thigpen, J. T. et al. (Feb. 1986). "Phase II Trial of Cisplatin in the Treatment of Patients with Advanced or Recurrent Mixed Mesodermal Sarcomas of the Uterus: A Gynecologic Oncology Group Study," *Cancer Treatment Reports* 70(2):271-274.

Thigpen, J. T. et al. (Oct. 1, 2004). "Phase III Trial of Doxorubicin With or Without Cisplatin in Advanced Endometrial Carcinoma: A Gynecologic Oncology Group Study," *J. Clin. Oncol.* 22(19):3902-3908.

Thomas, H. D. et al. (Mar. 2007). "Preclinical Selection of a Novel Poly(ADP-Ribose) Polymerase Inhibitor for Clinical Trial," *Mol. Cancer Ther.* 6(3):945-956.

Thompson, F. H. et al. (Mar. 1994). "Clonal Chromosome Abnormalities in 54 Cases of Ovarian Carcinoma," *Cancer Genet. Cytogenet.* 73(1):33-45.

Tuma, R. S. et al. (Sep. 25, 2007). "Targeting DNA Repair in BRCA Mutation Carriers," *Oncology Times* 29(18):52-53.

Turc-Carel, C. et al. (Jun. 1988). "Chromosomes in Ewing's Sarcoma. I. An Evaluation of 85 Cases of Remarkable Consistency of t(11;22)(q24;q12)," *Cancer Genet. Cytogenet.* 32(2):229-238.

Virag, L. et al. (1999). "Inhibition of Poly(ADP-Ribose) Synthetase (PARS) and Protection Against Peroxynitrite-Induced Cytotoxicity by Zinc Chelation," *Br. J. Pharmacol.* 126:769-777.

Virag, L. (1999). "Requirement of Intracellular Calcium Mobilization for Peroxynitrite-Induced Poly(ADP-Ribose) Synthetase Activation and Cytotoxicity," *Mol. Pharmacol.* 56:824-833.

Virag, L. et al. (Jan. 2001). "Purines Inhibit Poly(ADP-Ribose) Polymerase Activation and Modulate Oxidant-Induced Cell Death," *FASEB J.* 15:99-107.

Virag, L. et al. (2002). "The Therapeutic Potential of Poly(ADP-Ribose) Polymerase Inhibitors," *Pharmacol Rev.* 54(3):375-429.

Wang, Z. Q. et al. (1995). "Mice Lacking ADPRT and Poly(ADP-Ribosyl)ation Develop Normally but are Susceptible to Skin Disease," *Genes Dev.* 9:509-520.

Wang, Z.-Q. et al. (Sep. 15, 1997). "PARP is Important for Genomic Stability but Dispensable in Apoptosis," *Genes Dev.* 11(18):2347-2358.

Wasserman, E. J. et al. (2008). "Evolving Strategies for the Treatment of 'Triple-Negative' Breast Cancer," *American Society of Clinical Oncology Educational Book*, pp. 120-126.

Watson, C. Y. et al. (1998). "Synthesis of 3-Substituted Benzamides and 5-Substituted Isoquinolin-1(2H)-ones and Preliminary Evaluation as Inhibitors of Poly(ADP-Ribose)Polymerase (PARP)," *Bioorg Med Chem.* 6:721-734.

Weisner, R. J. et al. (Aug. 1992). "Detection of Rare mRNAs via Quantitative RT-PCR," *Trends Genet.* 8(8):263-264.

White, A. W. et al. (2000). "Resistance-Modifying Agents. 9. Synthesis and Biological Properties of Benzimidazole Inhibitors of the DNA Repair Enzyme Poly(ADP-Ribose) Polymerase," *J. Med. Chem.* 43:4084-4097.

Wiewrodt, D. et al. (Mar. 15, 2008). "MGMT in Primary and Recurrent Human Glioblastomas After Radiation and Chemotherapy and Comparison With p53 Status and Clinical Outcome," *Int. J. Cancer* 122(6):1391-1399.

Williams, C. et al. (1998). "Tamoxifen for Relapse of Ovarian Cancer," *Cochrane Database of Systematic Reviews of 1998*, Issue 2, reprinted and published in the Cochrane Library 2009, Issue 4, 19 pages total.

Winer, E. P. et al. (2007). "Optimizing Treatment of 'Triple-Negative' Breast Cancer," *30th Annual San Antonio Breast Cancer Symposium, selection from SABCS 2007: Improving Outcomes in Advanced and Metastatic Breast Cancer*, 4 pages total.

Wolff, M. E. ed. (1995). *Burger's Medicinal Chemistry and Drug Discovery, vol. I: Principles and Practice*, 5th edition, John Wiley & Sons, pp. 975-977.

Yalcintepe, L. et al. (Mar. 2005). "Changes in NAD/ADP-Ribose Metabolism in Rectal Cancer," *Braz. J. Med. Biol. Res.* 38(3):361-365.

Yang-Feng, T. L. et al. (Jul. 9, 1991). "Trisomy 12 and K-*ras*-2-Amplification in Human Ovarian Tumors," *Int. J. Cancer* 48(5):678-681.

Yanochko, G. M. et al. (Apr. 3, 2006). "Type I Insulin-Like Growth Factor Receptor Over-Expression Induces Proliferation and Anti-Apoptotic Signaling in a Three-Dimensional Culture Model of Breast Epithelial Cells," *Breast Cancer Res.* 8(2):R18, pp. 1-13.

Yoshida, S. et al. (Jan. 1991). "Production of 2-Methyl-4[$3H$]-Quinazolinone, an Inhibitor of Poly(ADP-Ribose) Synthetase, by Bacterium," *The Journal of Antibiotics* (Tokyo), 44(1):111-112.

Zabarovsky, E. R. et al. (Oct. 7, 2002). "Tumor Suppressor Genes on Chromosome 3p Involved in the Pathogenesis of Lung and Other Cancers," *Oncogene* 21(45):6915-6935.

Zhang, J. et al. (Nov. 30, 2000). "GPI 6150 Prevents $H_2O_2$ Cytotoxicity by Inhibiting Poly(ADP-Ribose) Polymerase," *Biochem. Biophys. Res. Comm.* 278(3):590-598.

International Search Report mailed on Oct. 16, 2007, for PCT Application No. PCT/US06/27907 filed on Jul. 18, 2006, 1 page.

Written Opinion of the International Search Authority mailed on Oct. 16, 2007, for PCT Patent Application No. PCT/US06/27907 filed on Jul. 18, 2006, 3 pages.

International Search Report mailed on Jun. 16, 2008, for PCT Application No. PCT/US07/77651 filed on Sep. 5, 2007, 1 page.

Written Opinion of the International Search Authority mailed on Jun. 16, 2008, for PCT Application No. PCT/US07/77651 filed on Sep. 5, 2007, 4 pages.

International Search Report mailed on Dec. 3, 2007, for PCT Application No. PCT/US07/71053 filed on Jun. 12, 2007, 1 page.

Written Opinion of the International Search Authority mailed on Dec. 3, 2007, for PCT Application No. PCT/US07/71053 filed on Jun. 12, 2007, 5 pages.

International Search Report mailed on Feb. 13, 2009, for PCT Application No. PCT/US08/85756 filed on Dec. 5, 2008, 1 page.

Non Final Office Action mailed on Dec. 2, 2009, for U.S. Appl. No. 11/850,626, filed Sep. 5, 2007, 8 pages.

Non Final Office Action mailed on Aug. 11, 2009, for U.S. Appl. No. 12/269,024, filed Nov. 11, 2008, 13 pages.

Non Final Office Action mailed on Mar. 4, 2010, for U.S. Appl. No. 12/269,833, filed Nov. 12, 2008, 25 pages.

U.S. Appl. No. 12/510,969, filed Jul. 28, 2009, for Sherman et al.

U.S. Appl. No. 12/748,209, filed Mar. 26, 2010, for Ossovskaya et al.

Balakumar, et al. Effect of 3-Aminobenzamide, an Inhibitor of Poly (ADP-Ribose)Polymerase in Experimental Cardiac Hypertrophy. International Journal of Pharmacology. 2006;2(5): 543-548.

Anders, C. et al. (Oct. 2008). "Understanding and Treating Triple-Negative Breast Cancer," *Oncology* 22(11):1233-1243.

Bakke, J. E. et al. (Jan. 1, 1988). "Metabolism of 2,6-Dichlorobenzamide in Rats and Mice," *Xenobiotica* 18(7):817-829.

Balendiran, G. K. et al. (Jan. 1, 2004). "The Role of Glutathione in Cancer," *Cell Biochemistry and Function* 22:343-352.

Behrens, P. et al. (2001). "Invasive Properties of Serous Human Epithelial Ovarian Tumors are Related to Ets-1, MMP-1 and MMP-9 Expression," *Int. J. Mol. Med.* 8:149-154.

Behrens, P. et al. (2001). "The Ets-1 Transcription Factor is Up-Regulated Together with MMP 1 and MMP 9 in the Stroma of Pre-Invasive Breast Cancer," *J. Pathol.* 194:43-50.

Bischoff, J. R. et al. (Nov. 1999). "The Aurora/Ipl1p Kinase Family: Regulators of Chromosome Segregation and Cytokinesis," *Trends Cell Biol.* 9:454-459.

Blakeley, J. O. et al. (Jun. 5, 2010). "Poly (ADP-ribose) Polymerase-1 (PARP1) Inhibitor BSI-201 in Combination with Temozolomide (TMZ) in Malignant Gilmoa," *J. Clin. Oncol.* 28(15)(May 20 Supplement):2012, also located at *ASCO Annual Meeting Proceedings* (*Post-Meeting Edition*) located at http://meeting.ascopubs.org/cgi/content/abstract/28/15_suppl/2012, 2 pages.

Bohula, E. A. et al. (Oct. 2003). "Targeting the Type 1 Insulin-like Growth Factor Receptor as Anti-Cancer Treatment," *Anti-Cancer Drugs* 14(9):669-682.

Bold, R. J. et al. (Sep. 2001). "Chemosensitization of Pancreatic Cancer by Inhibition of the 26S Proteasome," *J. Surg. Res.* 100(1):11-17.

Bryant, H. E. et al. (2004). "Poly(ADP-ribose) Polymerase Inhibitors as Potential Chemotherapeutic Agents," *Biochemical Society Transactions* 32(6):959-961.

Canova-Davis, E. et al. (Feb. 1976). "Chemical Modification of the Tryptophan Residue in Adrenocorticotropin," *Biochem.* 15(4):921-927.

Carey, L. A. (2010). "Directed Therapy of Subtypes of Triple Negative Breast Cancer," *The Oncologist* 15(Supplement 3 Preview):8-15.

Carey, L. A. et al. (Jan. 5, 2011). "PARP and Cancer—If It's Broke, Don't Fix It," *New England J. Med.* Located at http://www.nejm.org/doi/full/10.1056/NEJMe1012546, last visited on Jan. 6, 2011, 3 pages.

Castro, M. et al. (2010). "Pharmacokinetics of BSI-201, a Poly (ADP-ribose) Polymerase-1 (PARP1) Inhibitor, in Cerebrospinal Fluid (CSF) of a Patient with Breast Cancer with Carcinomatous Meningitits," *J. Clin. Oncol.* 28-Supplemental, Abstract No. e13559, 2 pages.

Chang, W. et al. (Dec. 14, 2001). "The Sequence-specific DNA Binding of NF-κb is Reversibly Regulated by the Automodification Reaction of Poly (ADP-ribose) Polymerase 1," *J. Biol. Chem.* 276(50):47664-47670.

Clinical Trial Registry NCT 00298675 (Mar. 2006). "Phase 1/1b Dose Escalation Study Evaluating BSI-201 as a Single Agent and in Combination With Irinotecan in Subjects With Advanced Solid Tumors," located at http://clinicaltrials.gov/ct2/show/NCT00298675, last visited on Oct. 27, 2010, first received on Mar. 1, 2006; last updated on Jun. 14, 2010, 5 pages.

Clinical Trial Registry NCT 00422682 (Jan. 2007). "A Study Evaluating BSI-201 in Combination With Chemotherapeutic Regimens in Subjects With Advanced Solid Tumors," located at http://clinicaltrials.gov/ct2/show/NCT00422682, last visited on Oct. 27, 2010, first received on Jan. 12, 2007, last updated on Jun. 14, 2010, 6 pages.

Clinical Trial Registry NCT 00540358 (Oct. 2007). "A Phase 2 Trial of Standard Chemotherapy, With or Without BSI-201, in Patients With Triple Negative Metastatic Breast Cancer," located at http://clinicaltrials.gov/ct2/show/NCT00540358, last visited on Oct. 27, 2010, first received on Oct. 4, 2007, last updated on Jun. 14, 2010, 7 pages.

Clinical Trial Registry NCT 00687765 (May 2008). "Study of the Poly (ADP-ribose) Polymerase-1 (PARP-1) Inhibitor BSI-201 in Patients With Newly Diagnosed Malignant Glioma," located at http://clinicaltrials.gov/ct2/show/NCT00687765, last visited on Oct. 27, 2010, first received on May 28, 2008, last updated on Jun. 14, 2010, 6 pages.

Clinical Trial Registry NCT 00687687 (May 2008). "Evaluation of Paclitaxel (Taxol, NSC #673089), Carboplatin (Paraplatin, NSC #241240), and BSI-201 (NSC #746045, IND #71,677) in the Treatment of Advanced, Persistent, or Recurrent Uterine Carcinosarcoma," located at http://clinicaltrials.gov/ct2/show/NCT00687687, last visited on Oct. 27, 2010, first received on May 28, 2008, last updated on Jun. 14, 2010, 5 pages.

Clinical Trial Registry NCT 00677079 (May 2008). "Single Arm Study of BSI-201 in Patients With BRCA-1 or BRCA-2 Associated Advanced Epithelial Ovarian, Fallopian Tube, or Primary Peritoneal Cancer," located at http://clinicaltrials.gov/ct2/show/NCT00677079, last visited on Oct. 27, 2010, first received on May 9, 2008, last updated on Jun. 14, 2010, 5 pages.

Clinical Trial Registry NCT 00813956 (Dec. 2008). "A Phase 2 Study of Standard Chemotherapy Plus BSI-201 (a PARP Inhibitor) in the Neoadjuvant Treatment of Triple Negative Breast Cancer," located at http://clinicaltrials.gov/ct2/show/NCT00813956, last visited on Oct. 27, 2010, first received on Dec. 19, 2008, last updated on Jun. 14, 2010, 5 pages.

Clinical Trial Registry NCT 00938652 (Jul. 10, 2009). "A Phase 3, Multi-Center Study of Gemcitabine/Carboplatin, With or Without BSI-201, in Patients With ER-, PR-, and Her2-Negative Metastatic Breast Cancer," located at http://clinicaltrials.gov/ct2/show/NCT00938652, last visited on Oct. 27, 2010, first received on Jul. 10, 2009, last updated on Jun. 14, 2010, 7 pages.

Clinical Trial Registry NCT 01033292 (Dec. 2009). "A Single-Arm Study Evaluating Carboplatin/Gemcitabine in Combination With BSI-201 in Patients With Platinum-Resistant Recurrent Ovarian Cancer," located at http://clinicaltrials.gov/ct2/show/NCT01033292, last visited on Oct. 27, 2010, first received on Dec. 14, 2009, last updated on Jun. 14, 2010, 6 pages.

Clinical Trial Registry NCT 01033123 (Dec. 2009). "A Single-Arm Study Evaluating Carboplatin/Gemcitabine in Combination With BSI-201 in Patients With Platinum-Sensitive Recurrent Ovarian Cancer," located at http://clinicaltrials.gov/ct2/show/NCT01033123, last visited on Oct. 27, 2010, first received on Dec. 14, 2009, last updated on Jun. 14, 2010, 6 pages.

Clinical Trial Registry NCT 01045304 (Jan. 2010). "Study of SAR240550 (BSI-201) in Combination With Gemcitabine/Carboplatin, in Patients With Metastatic Triple Negative Breast Cancer," located at http://www.clinicaltrials.gov/ct2/show/NCT01045304, last visited on Oct. 27, 2010, first received on Jan. 7, 2010, last updated on Sep. 2, 2010, 7 pages.

Clinical Trial Registry NCT 01082549 (Mar. 2010). "Trial of Gemcitabine/Carboplatin With or Without BSI-201 (a PARP1 Inhibitor) in Patients With Previously Untreated Advanced Squamous Cell Lung Cancer," located at http://clinicaltrials.gov/ct2/show/NCT01082549, last visited on Oct. 27, 2010, first received on Mar. 5, 2010, last updated on Aug. 30, 2010, 7 pages.

Clinical Trial Registry NCT 01130259 (May 2010). "An Open-Label, Expanded Access Protocol of Iniparib Breast Cancer," located at http://clinicaltrials.gov/ct2/show/NCT01130259, last visited on Oct. 27, 2010, first received on May 24, 2010, with no changes posted, 3 pages.

Clinical Trial Registry NCT 01173497 (Jul. 2010). "A Study Evaluating INIPARIB in Combination With Chemotherapy to Treat Triple Negative Breast Cancer Brain Metastasis," http://clinicaltrials.gov/ct2/show/NCT01173497, last visited on Oct. 27, 2010, first received on Jul. 28, 2010, last updated on Jul. 29, 2010; 5 pages.

Clinical Trial Registry NCT 01161836 (Aug. 2010). An Open-label Study Investigating the Disposition and QT/QTc Interval Effects of 400 mg [14C]-Iniparib(3.7 MBq, 100 µCi), located at http://clinicaltrials.gov/ct2/show/NCT01161836, last visited on Oct. 27, 2010, first received on Jul. 12, 2010, last updated on Aug. 20, 2010, 5 pages.

Clinical Trial Registry NCT 01086254 (Oct. 2010). "SAR240550 in Combination With Gemcitabine/Cisplatin in Non-small Cell Lung Cancer," located at http://clinicaltrials.gov/ct2/show/NCT01086254, last visited on Oct. 27, 2010, first received on Mar. 11, 2010, last updated on Aug. 17, 2010, 7 pages.

Clinical Trial Registry NCT 01204125, (Sep. 13, 2010). Two Regimens of SAR240550/Weekly Paclitaxel and Paclitaxel Alone as Neoadjuvant Therapy in Triple Negative Breast Cancer Patients (SOLTI NEOPARP), located at http://clinicaltrials.gov/ct2/show/NCT01204125, last visited on Jan. 26, 2011, first received on Sep. 13, 2010, last updated on Nov. 17, 2010, 13 pages.

Clinical Trial Registry NCT 01213381, (Sep. 30, 2010). "Safety and Pharmacokinetics of SAR240550 (BSI-201) Twice Weekly in Patients With Advanced Solid Tumors," located at http://clinicaltrials.gov/ct2/show/NCT01213381, last visited on Jan. 26, 2011, first received on Sep. 30, 2010, last updated on Oct. 1, 2010, 10 pages.

Cohen-Armon, M. (2007). "PARP-1 Activation in the ERK Signaling Pathway," *Trends Pharmacol. Sci.* 28(11):556-560.

Cory, S. et al. (2003). "The Bcl-2 Family: Roles in Cell Survival and Oncogenesis," *Oncogene* 22:8590-8607.

Curtin, N.J. (Mar. 15, 2005). "PARP Inhibitors for Cancer Therapy," *Expert. Rev. Mol. Med.* 7(4):1-20.

Cusack, J. C. et al. (May 1, 2001). "Enhanced Chemosensitivity to CPT-11 with Proteasome Inhibitor PS-341: Implications for Systemic Nuclear Factor-κB Inhibition," *Cancer Res.* 61:3535-3540.

Dittmer, J. (Aug. 20, 2003). "The Biology of the Ets1 Proto-Oncogene," *Mol. Cancer*, available at http://www.molecular-cancer.com/content/2/1/29, 2(29):1-21.

Donleavy, J. J. et al. (Jul. 1, 1947). "Alkamine Esters and Amides of Some Amino-Alkylmercaptobenzoic Acids," *J. Amer. Chem. Soc.* 69(7):1781-1784.

Dwyer, J. et al. (2007). "Transcriptional Regulation of Telomerase Activity: Roles of the the Ets Transcription Factor Family," *Ann. New York Acad. Sci.* 1114:36-47.

Fischer, F. et al. (Dec. 2007). "5-Fluorouracil is Efficiently Removed from DNA by the Base Excision and Mismatch Repair Systems," *Gastroenterology* 133(6):1858-1868.

Geissler, T. et al. (2010). "PARP Inhibitors as Agrochemically Active Substances," *PARP 2010, 18th International Conference on ADP-Ribose Metabolism*, Aug. 18-21, 2010, University of Zurich-Irchel, Zurich, Switzerland, Poster Presentation, Abstract No. P71, 3 pages.

Gonzalez, R. J. et al. (2001). "Evaluation of Hepatic Subcellular Fractions for Alamar Blue and MTT Reductase Activity," *Toxicol. In Vitro* 15:257-259.

Goodman et al. (1996). The Pharmacological Basis of Therapeutic, 9th Edition, pp. 1225-1232, 1269-1271.

Gotlieb, W. H. et al. (2006). "Insulin-like Growth Factor Receptor I Targeting in Epithelial Ovarian Cancer," *Gynecol. Oncol.* 100:389-396.

Hagan, M. P. et al. (2007). "Radiation-Induced PARP Activation is Enhanced Through EGFR-ERK Signaling," *J. Cell Biochem.* 101:1384-1393.

Hatake, K. et al. (Apr. 2007). "Next Generation Molecular Targeted Agents for Breast Cancer: Focus on EGFR and VEGFR Pathways," *Breast Cancer* 14(2):132-149.

Hideshima, T. et al. (May 10, 2002). "NF-κB as a Therapeutic Target in Multiple Myeloma," *J. Biol. Chem.*, available at http://www.jbc.org (last visited on Aug. 31, 2010), 277(19):16639-16647.

Hirai, K. et al. (Jul. 1983). "Aberration of Poly(Adenosine Diphosphate-Ribose) Metabolism in Human Colon Adenomatous Polyps and Cancers," *Cancer Research* 43:3441-3446.

Hutcheson, I. R. et al. (2006). "Inductive Mechanisms Limiting Response to Anti-Epidermal Growth Factor Receptor Therapy," *Endocrine-Rel. Cancer* 13:S89-S97.

Jiang, Y. et al. (Sep. 7, 2001). "Invasiveness of Hepatocellular Carcinoma Cell Lines: Contribution of Hepatocyte Growth Factor, c-met, and Transcription Factor Ets-1," *Biochem. Biophys. Res. Commun.* 286(5):1123-1130.

Jones, H. E. et al. (2006). "Growth Factor Receptor Interplay and Resistance in Cancer," *Endocrine-Rel. Cancer* 13:S45-S51.

Kang, S. P. et al. (Feb. 2008). "Triple Negative Breast Cancer: Current Understanding of Biology and Treatment Options," *Curr. Opin. Obstet. Gynecol.* 20(1):40-46.

Karamouzis, M. V. et al. (Jul. 4, 2007). "Therapies Directed Against Epidermal Growth Factor Receptor in Aerodigestive Carcinomas," *JAMA* 298(1):70-82.

Kari, C. et al. (Jan. 1, 2003). "Targeting the Epidermal Growth Factor Receptor in Cancer: Apoptosis Takes Center Stage," *Cancer Res.* 63:1-5.

Kelly, E. A. B. et al. (2000). "Increased Matrix Metalloproteinase-9 in the Airway After Allergen Challenge," *Am. J. Resp. Crit. Care Med.* 162:1157-1161.

Khan, Z. A. et al. (2006). "Therapeutic Targeting of Endothelial Dysfunction in Chromic Diabetic Complications," *Recent Patents in Cardiovascular Drug Discovery* 1:167-175.

Khandwala, H. M. et al. (2000). "The Effects of Insulin-Like Growth Factors on Tumorigenesis and Neoplastic Growth," *Endo. Rev.* 21(3):215-244.

Kimura, M. et al. (May 23, 1997). "Cell Cycle-dependent Expression and Spindle Pole Localization of a Novel Human Protein Kinase, Aik, Related to Aurora of *Drosophila* and Yeast Ipl1," *J. Biol. Chem.*, available at http://www.jbc.org (last visited on Sep. 7, 2010), 272(21):13766-13771.

Kitange, G. et al. (Apr. 1999). "Ets-1 Transcription Factor-Mediated Urokinase-Type Plasminogen Activator Expression and Invasion in Glioma Cells Stimulated by Serum and Basic Fibroblast Growth Factors," *Lab. Invest.* 79(4):407-416.

Kopetz, S. et al. (May 20, 2008). "First in Human Phase I Study of BSI-201, a Small Molecule Inhibitor of Poly ADP-Ribose Polymerase (PARP) in Subjects with Advanced Solid Tumors," *J. Clin. Oncol.* 26(Supplemental), Abstract No. 3577, 3 pages.

Kopetz, S. et al. (May 20, 2008). "First in Human Phase I Study of BSI-201, a Small Molecule Inhibitor of Poly ADP-Ribose Polymerase (PARP) in Subjects with Advanced Solid Tumors," Poster Session presented for *J. Clin. Oncol.* 26(Supplemental), Abstract No. 3577, 1 page (Poster).

Li, Z. et al. (Jan. 1, 2005). "BCL-6 Negatively Regulates Expression of the NF-κB1 p105/p50 Subunit," *J. Immunol.* 174:205-214.

Linardopoulos, S. (Sep. 2007). "Aurora-A Kinase Regulates NF-kB Activity: Lessons from Combination Studies," *J. Buon.* 12(Suppl. 1):S67-S70.

Mabuchi, S. et al. (May 28, 2004). "Inhibition of NFκB Increases the Efficacy of Cisplatin in in Vitro and in Vivo Ovarian Cancer Models," *J. Biol. Chem.*, available at http://www.jbc.org (last visited on Sep. 1, 2010), 279(22):23477-23485.

Maegley, K. A. et al. (2010). "An In Vitro Mechanistic Comparison of Clinical PARP Inhibitors," *PARP 2010, 18th International Conference on ADP-Ribose Metabolism*, Aug. 18-21, 2010, University of Zurich-Irchel, Zurich, Switzerland, Poster Presentation, Abstract No. P72, 3 pages.

Mahaney, J. J. et al. (May 20, 2008). "A Phase IB Study Evaluating BSI-201 in Combination with Chemotherapy in Subjects with Advanced Solid Tumours," *J. Clin. Oncol.* 26(Supplemental), Abstract No. 3579, 3 pages.

Makarov, V. et al. (2006). "Synthesis and Antileprosy Activity of Some Dialkyldithiocarbamates," *J. Antimicrob. Chemotherapy* 57:1134-1138.

Martin, S. A. et al. (Feb. 2008, e-pub. Mar. 14, 2008). "DNA Repair Deficiency as a Therapeutic Target in Cancer," *Curr. Opin. Genet. Dev.* 18(1):80-86.

Melisi, D. et al. (Oct. 2007). "The Novel Poly(ADP-ribose) Polymerase (PARP)-1 Inhibitor, BSI-401, has Antitumor Activity and Potentiates Oxaliplatin Cytotoxic Activity in Human Pancreatic Cancer," *AACR-NCI-EORTC International Conference: Molecular Targets and Cancer Therapeutics*, San Francisco, CA, Oct. 22-26, 2007, Abstract B282, located at <http://www.aacrmeetingabstracts.org/cgi/content/meeting_abstract/2007/3_Molecular_Targets_Meeting/B282?maxtoshow=&HITS=10&hits=10&RESULTFORMAT=&author1=melisi&andorexactfulltext=and&searchid=1&FIRSTINDEX=0&sortspec=relevance&resourcetype=HWCIT>, last visited on Jul. 15, 2010, 2 pages.

Melisi, D. et al. (Jan. 2009). "Antitumour Efficacy of the Novel Poly(ADP-Ribose) Polymerase (PARP-1) Inhibitor BSI-401 and Synergism with Oxaliplatin (OX) in an Orthotopic Murine Model of Pancreatic Cancer (PC)," *2009 Gastrointestinal Cancers Symposium*, located at <http://www.asco.org/ASCOv2/Meetings/Abstracts?&vmview=abst_detail_view&confID=63&abstractID=10481>, last visited on Jul. 12, 2010, Abstract No. 164, 4 pages.

Mori, N. et al. (Apr. 1, 1999). "Constitutive Activation of NF-κB in Primary Adult T-Cell Leukemia Cells," *Blood* 93(7):2360-2368.

Mori, N. et al. (Sep. 1, 2002). "Bay 11-7082 Inhibits Transcription Factor NF-κB and Induces Apoptosis of HTLV-I-Infected T-cell Lines and Primary Adult T-cell Leukemia Cells," *Blood* 100(5):1828-1834.

Moschos, S. J. et al. (2002). "The Role of the IGF System in Cancer: From Basic to Clinical Studies and Clinical Applications," *Oncology* 63:317-332.

Moulder, S. et al. (Dec. 12, 2010). "[P6-15-01] A Phase 1b Study to Assess the Safety and Tolerability of the PARP Inhibitor Iniparib (BSI-201) in Combination With Irinotecan for the Treatment of Patients With Metastatic Breast Cancer (MBC)," *Abstract related to Poster Session No. 6: Treatment—Therapeutic Strategies: Novel Targets and Targeted Agents, presented at the 33rd Annual San Antonio Breast Cancer Symposium*, held on Dec. 8-12, 2010, San Antonio, Texas,, Abstract located at http://www.abstracts2view.com/sabcs10/view.php?nu=SABCS10L_1107&terms=, last visited on Dec. 22, 2010, 1 page (Abstract).

Moulder, S. et al. (Dec. 12, 2010). "[P6-15-01] A Phase 1b Study to Assess the Safety and Tolerability of the PARP Inhibitor Iniparib (BSI-201) in Combination With Irinotecan for the Treatment of Patients With Metastatic Breast Cancer (MBC)," *Poster Session No. 6: Treatment—Therapeutic Strategies: Novel Targets and Targeted Agents, presented at the 33rd Annual San Antonio Breast Cancer Symposium*, held on Dec. 8-12, 2010, San Antonio, Texas, 1 page (Poster).

Naito, S. et al. (2000). "Overexpression of Ets-1 Transcription Factor in Angiosarcoma of the Skin," *Pathol. Res. Pract.* 196:103-109.

Nakada, M. et al. (Apr. 1999). "Ets-1 Positively Regulates Expression of Urokinase-type Plasminogen Activator (uPA) and Invasiveness of Astrocytic Tumors," *J. Neuropathol. Exp. Neurol.* 58(4):329-334.

Neumeister, V. et al. (Dec. 12, 2010). [P6-04-04] Hypoxia is Associated With Somatic Loss of BRCA1 Protein and Pathway Activity in Triple Negative Breast Cancer, *Abstract related to Poster Session 6: Tumor Cell and Molecular Biology: Molecular Profiles, presented at the 33rd Annual San Antonio Breast Cancer Symposium*, held on Dec. 8-12, 2010, San Antonio, Texas, 1 page (Abstract).

O'Shaughnessy, J. et al. (Dec. 12, 2008). "Triple Negative Breast Cancer: A Phase 2, Multi-center, Open-label, Randomized Trial of Gemcitabine/Carboplatin (G/C), with or without BSI-201, a PARP Inhibitor," *San Antonio Breast Cancer Symposium Annual Meeting 2008*, San Antonio, TX, located at <http://www.abstracts2view.com/sabcs/view.php?nu=SABCSO8L_612&terms=>, last visited on Jul. 12, 2010, 1 page.

O'Shaughnessy, J. et al. (2009). "Efficacy of BSI-201, A Poly (ADP-ribose) Polymerase-1 (PARP1) Inhibitor, in Combination with Gemcitabine/Carboplatin (G/C) in Patients with Metastatic Triple-Negative Breast Cancer (TNBC): Results of a Randomized Phase II Trial," *J. Clinl. Oncol.* 27:182, Abstract No. 3, 4 pages.

O'Shaughnessy, J. et al. (Dec. 11, 2009). "Updated Results of a Randomized Phase II Study Demonstrating Efficacy and Safety fo BSI-201, A PARP Inhibitor, in Combination with Gemcitabine/Carboplatin in Metastatic Triple-Negative Breast Cancer," *San Antonio Breast Cancer Symposium*, San Antonio, Texas, Dec. 9-13, 2009, located at <http://www.posters2view.com/sabcs09/viewp.php?nu=3122>, last visited on Jul. 12, 2010, 1 page.

O'Shaughnessy, J. (2010). "Triple Negative Breast Cancer: The Emerging Treatment with BSI-201 (Iniparib)," *The Oncologist* 15(Supplement 3 Preview):1-7.

O'Shaughnessy, J. et al. (Oct. 2010). Final Efficacy and Safety Results of a Randomized Phase II Study of the PARP Inhibitor Iniparib (BSI-201) in Combination With Gemcitabine/Carboplatin (G/C) in Metastatic Triple Negative Breast Cancer (TNBC), *Annals of Oncology, ESMO 2010 Late-Breaking Abstracts, Presidential Symposium*, 21(8): Abstract No. LAB11, p. viii5.

O'Shaughnessy, J. et al. (Oct. 2010). "LAB11—Iniparib With Gem/Carbo, A PARP Inhibitor Strategy, in Metastatic Triple Negative Breast Cancer," & A. Awada et al. "Cationic Liposomal Paclitaxel, A Vascular Disruption Strategy in Advanced Triple Negative Breast Cancer," *Final Oral presentation presentation presented by J. O'shaughnessy et al., and A. Awada et al., at the ESMO 2010 Congress*, Milan 2010, 17 pages total.

O'Shaughnessy, J. et al. (2011). "Iniparib Plus Chemotherapy in Metastatic Triple-Negative Breast Cancer," *The New England Journal of Medicine*, 10.1056/NEJMoa1011418, and Supplementary Appendix, for a total of 14 pages.

Oda, N. et al. (1999). "ETS-1 Converts Endothelial Cells to the Angiogenic Phenotype by Inducing the Expression of Matrix Metalloproteinases and Integrin $\beta_3$," *J. Cell. Physiol.* 178:121-132.

Oda, K. et al. (2005). "A Comprehensive Pathway Map of Epidermal Growth Factor Receptor Signaling," *Mol. Sys. Biol.* 2005.0010:1-17.

Ossavskaya, V. et al. (Oct. 2007). "PARP1 Gene Over-expression in Primary Human Cancers: A Potential Marker for PARP Inhibition," *AACR-NCI-EORTC International Conference: Molecular Targets and Cancer Therapeutics*, San Francisco, CA, Oct. 22-26, 2007, located at <http://www.aacrmeetingabstracts.org/cgi/content/meeting_abstract/2007/3_Molecular_Targets_Meeting/C125?maxtoshow=&HITS=10&hits=10&RESULTFORMAT=&fulltext=bsi-201&andorexactfulltext=and&searchid=1&FIRSTINDEX=0&sortspec=relevance&resourcetype=HWCIT>, last visited on Jul. 15, 2010, Abstract C125, 2 pages.

Ossovskaya, V. et al. (Nov. 2007). "The PARP1 Gene is Over-expressed in Triple Negative Breast Cancer," *European Journal of Cancer Supplements* 5(8):31, Abstract No. P57.

Ossovskaya, V. et al. (Apr. 2008). "Activity of BSI-201, a Potent Poly(ADP-ribose) Polymerase (PARP1) Inhibitor, Alone and in Combination with Topotecan in Human Ovarian Xenografts," *99th AACR Annual Meeting*, San Diego, CA, Apr. 12-16, 2008, Abstract No. 2311 located at <http://www.aacrmeetingabstracts.org/cgi/content/meeting_abstract/2008/1_Annual_Meeting/2311?maxtoshow=&HITS=10&hits=10&RESULTFORMAT=&fulltext=bsi-201&andorexactfulltext=and&searchid=1&FIRSTINDEX=0&sortspec=relevance&resourcetype=HWCIT>, last visited on Jul. 15, 2010, 2 pages.

Ossovskaya, V. et al. (Apr. 22, 2009). "BSI-201 Enhances the Activity of Multiple Classes of Cytotoxic Agents and Irradiation in Triple Negative Breast Cancer," *2009 AACR Annual Meeting*, Denver, CO, Apr. 18-22, 2009, located at <http://www.abstractsonline.com/viewer/viewAbstract.asp?CKey=%7BA98A01B0-1623-4F71-99C7-FCE19F299C1F%7D&MKey=%7BD007B270-E8F6-492D-803B-7582CE7A0988%7D&AKey=%7B728BCE9C-121B-46B9-A8EE-DC51FDFC6C15%7D&SKey=%7BCCA05FCE-642E-4E26-AD12-29C831335BE1%7D>, last visited on Jul. 12, 2010, 2 pages.

Ossovskaya, V. et al. (2010). "Pathway Analysis of Primary Human Triple-Negative Breast Cancers," Poster Session No. 6: Tumor Cell and Molecular Biology: Molecular Profiles, presented at the 33rd Annual San Antonio Breast Cancer Symposium, San Antonio, Texas, USA, Dec. 8-12, 2010, one page (Poster).

Ossovskaya, V. et al. (2010). "[P06-04-12] Pathway Analysis of Primary Human Triple-Negative Breast Cancers," Abstract presented at the 33rd Annual San Antonio Breast Cancer Symposium, San Antonio, Texas, USA, Dec. 12, 2010, abstract located at http://www.abstracts2view.com/sabcs10/view.php?nu=SABCS10L_423&terms=, last visited on Jan. 6, 2011, one page (Abstract).

Ossovskaya, V. et al. (2010). "Cell Cycle Effects of Iniparib, A PARP Inhibitor, in Combination With Gemcitabine and Carboplatin in the MDA-MB-468(−) Triple-Negative Breast Cancer (TNBC) Cell Line," Oral Presentation No. P05-06-09, presented at the 33rd Annual San Antonio Breast Cancer Symposium, San Antonio, Texas, USA, Dec. 8-12, 2010, one page.

Pal, S. K. et al. (2010). "Triple Negative Breast Cancer: Unmet Medical Needs," *Breast Cancer Research and Treatment* 125(3):627-636.

Parker, J. S. et al. (Mar. 10, 2009). "Supervised Risk Predictor of Breast Cancer Based on Intrinsic Subtypes," *J. Clin. Oncol.* 27(8):1160-1167.

Phend, C. (Jan. 5, 2011). "PARP Inhibitor Shines in Triple-Negative Breast Cancer," *News Release from Medpage Today*, article located at http://www.medpagetoday.com/HematologyOncology/BreastCancer/24195, last visited on Jan. 6, 2011, 4 pages.

Pollak, M. N. et al. (Jul. 2004). "Insulin-like Growth Factors and Neoplasia," *Nature Rev. Cancer* 4(7):505-518.

Prat, A. et al. (2010). "Deconstructing the Molecular Portraits of Breast Cancer," *Molecular Oncology* XXX:1-18 (doi:10/1016/j.molonc.2010.04.003).

Riedemann, J. et al. (2006). "IGF1 R Signalling and Its Inhibition," *Endocr. Relat. Cancer* 13:S33-S43.

Roberts, R. B. at al. (Feb. 5, 2002). "Importance of Epidermal Growth Factor Receptor Signaling in Establishment of Adenomas and Maintenance of Carcinomas During Intestinal Tumorigenesis," *PNAS* 99(3):1521-1526.

Rocha-Lima, C. M. et al. (Jul. 2007). "EGFR Targeting of Solid Tumors," *Cancer Control* 14(3):295-304.

Rodon, J. et al. (Jan. 2009). "Development of PARP Inhibitors in Oncology," *Expert Opin. Investig. Drugs* 18(1):31-43.

Sano, K. et al. (Jan. 1, 2001). "Metabolism of Sulphobromophtalein I: Positional Isomers of Sulphobromophthalein Monoglutathione Conjugate," *J. Pharmacy & Pharmacology* 53:1015-1020.

Sato, Y. et al. (2000). "Signal Transduction and Transcriptional Regulation of Angiogenesis," in *Angiogenesis From the Molecular to Integrative Pharmacology*, Maragoudakis, M.E. ed., Kluwer Academic/Plenum Publishers, New York, NY, 476:109-115.

Sementchenko, V. I. et al. (2000). "Ets Target Genes: Past, Present and Future," *Oncogene* 19:6533-6548.

Sequist, L. V. (2007). "Second-Generation Epidermal Growth Factor Receptor Tyrosine Kinase Inhibitors in Non-Small Cell Lunch Cancer," *Oncologist*, available at http://www.TheOncologist.com (last visited on Sep. 1, 2010), 12:325-330.

Sestili, P. et al. (1990). "Structural Requirements for Inhibitors of Poly(ADP-ribose) Polymerase," *J. Cancer. Res. Clin. Oncol.* 116:615-622.

Shah, S. A. et al. (2001). "26S Proteasome Inhibition Induces Apoptosis and Limits Growth of Human Pancreatic Cancer," *J. Cell Biochem.* 82:110-122.

Sharrocks, A. D. et al. (1997). "The ETS-domain Transcription Factor Family," *Int. J. Biochem. Cell. Biol.* 29(12):1371-1387.

Shiu, K.K. et al. (Sep. 2008). "Development of Therapeutic Approaches to 'Triple Negative' Phenotype Breast Cancer," *Expert Opin. Ther. Targets* 12(9):1123-1137.

Sørlie, T. et al. (Sep. 11, 2001). "Gene Expression Patterns of Breast Carcinomas Distinguish Tumor Subclasses with Clinical Implications," *Proc. Natl. Acad. Sci. USA* 98(19):10869-10874.

St-Pierre, Y. et al. (2004). "Regulation of MMP-9 Gene Expression for the Development of Novel Molecular Targets Against Cancer and Inflammatory Diseases," *Expert Opin. Therp. Targets* 8(5):473-489.

Takanami, I. et al. (2001). "Expression of Ets-1 is Correlated with Urokinase-Type Plasminogen Activator and Poor Prognosis in Pulmonary Adenocarcinoma," *Tumor Biol.* 22:205-210.

Tong, Q. et al. (Mar. 2, 2006). "VEGF is Upregulated by Hypoxia-induced Mitogenic Factor via the PI-3K/Akt-NF-κB Signaling Pathway," *Respir. Res.* 7(37):1-14.

Toshi, L. et al. (2007). "Understanding the New Genetics of Responsiveness to Epidermal Growth Factor Receptor Tyrosine Kinase Inhibitors," *Oncologist* 12:211-220.

Tummino, P. J. et al. (Feb. 1, 1997). "The Human Immunodeficiency Virus Type 1 (HIV-1) Nucleocapsid Protein Zinc Ejection Activity of Disulfide Benzamides and Benzisothiazolones: Correlation With Anti-HIV and Virucidal Activities," *Antimicrobial Agents and Chemotherapy* 41(2):394-400.

Wang, T-L. et al. (Mar. 2, 2004). "Digital Karyotyping Identifies Thymidylate Synthase Amplification as a Mechanism of Resistance to 5-Fluorouracil in Metastatic Colorectal Cancer Patients," *Proc. Natl. Acad. Sci. USA* 101(9):3089-3094.

Werner, H. et al. (2003). "The *IGFI* Receptor Gene: A Molecular Target for Disrupted Transcription Factors," *Genes, Chromo. Cancer* 36:113-120.

Wikipedia (2011). "Fatty Acid Synthesis," located at http://en.wikipedia.org/wiki/Fatty_acid_synthesis, last visited on Jan. 18, 2011, this page was created on Feb. 18, 2007, and last modified on Jan. 7, 2011 at 02:23, 2 pages.

Woodhouse, B.C. et al. (Jul. 1, 2008, e-pub. May 12, 2008). "Poly ADP-ribose Polymerase-1: An International Molecule of Mystery," *DNA Repair (Amst.)*7(7):1077-1076.

Xie, Z. et al. (Jun. 7, 2007). "A Multiplex RT-PCR for Simultaneous Differentiation of Three Viral Pathogens of Penaeid Shrimp," *Dis. Aquat. Organ.* 76:77-80.

Yang, J. et al. (Feb. 1, 2006). "BMS-345541 Targets Inhibitor of κB Kinase and Induces Apoptosis in Melanoma: Involvement of Nuclear Factor κB and Mitochondria Pathways," *Clin. Cancer Res.* 12(3):950-960.

Zingarelli, B. et al. (1997). "Protection Against Myocardial Ischemia and Reperfusion Injury by 3-Aminobenzamide, an Inhibitor of Poly (ADP-ribose) Synthetase," *Cardiovascular Research* 36:205-215.

International Search Report mailed on Jun. 18, 2008, for PCT Patent Application No. PCT/US07/77662 filed on Sep. 5, 2007, published on Mar. 13, 2008, for PCT Publication No. WO 2008/30891, 2 pages.

Written Opinion mailed on Jun. 18, 2008, for PCT Patent Application No. PCT/US07/77662 filed on Sep. 5, 2007, published on Mar. 13, 2008, for PCT Publication No. WO 2008/30891, 3 pages.

Written Opinion mailed on Feb. 13, 2009, for PCT Application No. PCT/US08/85756 filed on Dec. 5, 2008, published on Jun. 11, 2009, as PCT Publication No. WO 2009/073869, 4 pages.

International Preliminary Report on Patentability mailed on Jun. 17, 2010, for PCT Application No. PCT/US08/85756 filed on Dec. 5, 2008, 6 pages.

International Search Report mailed on Sep. 10, 2009, for PCT Patent Application No. PCT/US09/033117, filed on Feb. 4, 2009, published on Aug. 13, 2009, as PCT Publication No. WO 2009/100159, 5 pages.

Written Opinion mailed on Sep. 10, 2009, for PCT Patent Application No. PCT/US09/033117, filed on Feb. 4, 2009, published on Aug. 13, 2009, as PCT Publication No. WO 2009/100159, 4 pages.

International Search Report mailed on Mar. 23, 2010, for PCT Patent Application No. PCT/US2010/023137 filed on Feb. 4, 2010, published on Aug. 12, 2010, as PCT Publication No. WO 2010/091140, 4 pages.

Written Opinion mailed on Mar. 23, 2010, for PCT Patent Application No. PCT/US2010/023137 filed on Feb. 4, 2010, published on Aug. 12, 2010, as PCT Publication No. WO 2010/091140, 5 pages.

Supplementary European Search Report mailed Dec. 13, 2010, for EP Patent Application No. 07814695.8, filed on Sep. 5, 2007, 8 pages.

European Search Opinion mailed Dec. 13, 2010, for EP Patent Application No. 07814695.8, filed on Sep. 5, 2007, 8 pages.

Supplementary European Search Report mailed on Jul. 6, 2010, for EP Patent Application No. 07841902.5, filed on Sep. 5, 2007, 9 pages.

European Search Opinion mailed on Jul. 6, 2010, for EP Patent Application No. 07841902.5, filed on Sep. 5, 2007, 6 pages.

Supplementary European Search Report mailed on Jul. 8, 2010, for EP Patent Application No. 07875034.6, filed on Jun. 12, 2007, 14 pages.

European Search Opinion mailed on Jul. 8, 2010, for EP Patent Application No. 07875034.6, filed on Jun. 12, 2007, 8 pages.

Non Final Office Action mailed on Jul. 30, 2010, for U.S. Appl. No. 12/165,437, filed Jun. 30, 2008.

Final Office Action mailed on Jan. 6, 2011, for U.S. Appl. No. 12/165,437, filed Jun. 30, 2008, 11 pages.

Final Office Action mailed on Oct. 8, 2010, for U.S. Appl. No. 12/269,833, filed Nov. 12, 2008, 19 pages.

Kuhajda, F. P. et al. (Jul. 5, 1994). "Fatty Acid Synthesis: A Potential Selective Target for Antineoplastic Therapy," *Proc. Nat'l. Acad. Sci USA* 91(14):6379-6383.

Kuhajda, F. P. et al. (Mar. 28, 2000). "Synthesis and Antitumor Activity of an Inhibitor of Fatty Acid Synthase," *Proc. Nat'l. Acad. Sci USA* 97(7):3450-3454.

Menendez, J. A. et al. (Apr. 1, 2005). "Does Endogenous Fatty Acid Metabolism Allow Cancer Cells to Sense Hypoxia and Mediate Hypoxic Vasodilation? Characterization of a Novel Molecular Connection Between Fatty Acid Synthase (FAS) and Hypoxia-Inducible Factor-1α (HIF-1α)-Related Expression of Vascular Endothelial Growth Factor (VEGF) in Cancer Cells Overexpressing Her-2/*neu* Oncogene," *J. Cell Biochem* 94(5):857-863.

Menendez, J. A. et al. (Jul./Aug. 2005). "Targeting Fatty Acid Synthase: Potential for Therapeutic Intervention in Her-2/*neu*-Overexpressing Breast Cancer," *Drug News & Perspective* 18(6):375-385.

* cited by examiner

MONITORING OF THE INHIBITION OF FATTY ACID SYNTHESIS BY IODO-NITROBENZAMIDE COMPOUNDS

CROSS-REFERENCE

This application claims the benefit of U.S. Provisional Application No. 60/842,479, filed Sep. 5, 2006, which is incorporated herein by reference in its entirety.

BACKGROUND OF THE INVENTION

Fatty acid synthase (FAS) is an enzyme required to convert carbohydrates to fatty acids. In normal humans, the fatty acid synthetic pathway is down-regulated because of sufficiently high levels of dietary fat. However, in a wide variety of human malignancies and their precursor lesions, such as, prostate cancer, ovarian cancer, and breast cancer, the tissues express high levels of fatty acid synthase resulting in high levels of fatty acids. An up-regulation of FAS in most human cancers leads to the notion that FAS plays a role in the development, maintenance, and/or enhancement of the malignant cancer phenotype and that FAS can be a target for anticancer drug development.

About 1.2 billion people in the world are overweight and at least 300 million of them are obese. In the United States, more than 97 million adults—that's more than half—are overweight and almost one in five adults is obese. Reduction of the fatty acid synthesis in the obese can be an effective treatment for obesity.

Treatment of cancer cells in vitro with cerulenin, a covalent inactivator of the β-ketoacyl synthase reaction on FAS, led to cell death by means of apoptosis, demonstrating that cancer cells with highly active fatty acid synthesis require a functional pathway (Pizer et al. (1996) *Cancer Res.* 56, 2745-2747). Cerulenin, however, has limited in vivo activity. FAS has been shown to be one of the genes regulated by Her-2/neu at the level of transcription, translation, and biosynthetic activity (Menedez et al. (2005) *Drug New Perspect*, 18(6), July/August). This Her-2/neu-induced up-regulation of breast-cancer associated FAS is inhibitable by anti-Her-2/neu antibodies such as trastuzumab. Studies with C75, an inhibitor of fatty acid synthesis, have shown anti-tumor activity with inhibition of fatty acid synthesis in tumor tissue (Kuhajda et al. (2000) *Proc. Natl. Acad. Sci.* vol. 97, no. 7, 3450-3454). FAS inhibitors have also been shown to activate weight-reducing pathways (Loftus, T. M. et al. (2000)*Science* 288, 2379-2381).

As fatty acid synthesis plays a role in cancer and weight gain pathways, there continues to be a need to develop effective fatty acid synthesis inhibitors.

SUMMARY OF THE INVENTION

One aspect of the invention relates to a method of treating a fatty acid synthesis and metabolism related disease comprising administering to a patient in need thereof an effective amount of a PARP inhibitor or metabolite thereof to inhibit fatty acid synthesis, wherein the fatty acid synthesis related disease is obesity, diabetes, or cardiovascular disease.

Another aspect of the present invention relates to a method of treating a cancer in a subject comprising: (i) identifying a level of fatty acid in a sample from the subject, and (ii) administering an effective amount of a PARP inhibitor or metabolite thereof to inhibit fatty acid synthesis wherein the administration is based on the level of fatty acid, thereby treating the cancer in the subject.

In some embodiments of the present invention, the fatty acid is a medium chain fatty acid or a long chain fatty acid. The medium chain fatty acids include C:6-C:12. The long chain fatty acids include a chain length of greater than 12 carbons. In some embodiments, the inhibition of the fatty acid synthesis comprises inhibiting at least one enzyme of a glucose pathway. In some embodiments, the inhibition of the fatty acid synthesis comprises inhibiting at least one enzyme of a fatty acid biosynthetic pathway. In some embodiments, the inhibition of the fatty acid synthesis comprises inhibiting at least one enzyme selected from the group consisting of acetyl Co-A, malonyl Co-A, acetyl Co-A carboxylase, and fatty acid synthase. In some embodiments, the fatty acid synthase comprises acyl carrier protein, acetyl transferase, malonyl transferase, 3-keto-acyl-ACP synthase, 3-ketoacyl-ACP reductase, 3-hydroxy-acyl-ACP dehydratase, and enoyl-ACP reductase. In some embodiments, the inhibition of the fatty acid synthesis comprises inhibiting at least one enzyme of a fatty acid synthase. In some embodiments, the inhibition of the fatty acid synthesis comprises inhibiting synthesis of an acetyl-CoA from a glucose. In some embodiments, the inhibition of the fatty acid synthesis comprises inhibiting the fatty acid synthesis from an acetyl-CoA.

In some embodiments of the aforementioned aspect of the present invention, the long chain fatty acid is C:14-C:30. In some embodiments, the long chain fatty acid is C:14, C:16, C:18, C:18-1, C:20, C:22, or C:24. In some embodiments, the inhibition is determined by analyzing a metabolite or a molecular flux of a glucose pathway or a fatty acid biosynthetic pathway. In some embodiments, the metabolite is selected from the group consisting of glucose, glycogen, lactate, $CO_2$, fatty acid, acetyl Co-A, RNA ribose and DNA deoxyribose. In some embodiments, the metabolite is chemically derivatized for the analysis. In some embodiments, the analysis comprises mass spectrometry. In some embodiments, the mass spectrometry is mass isotopomer distribution analysis. In some embodiments, the level of fatty acid is up-regulated.

In some embodiments of the aforementioned aspect of the present invention, the PARP inhibitor or metabolite thereof is a compound of formula I, its pharmaceutically acceptable salts or prodrugs thereof:

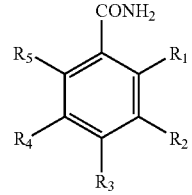

Formula I wherein, $R_1$, $R_2$, $R_3$, $R_4$, and $R_5$ are independently selected from the group consisting of hydrogen, hydroxy, optionally substituted amine, carboxyl, ester, nitroso, nitro, halogen, optionally substituted ($C_1$-$C_6$) alkyl, optionally substituted ($C_1$-$C_6$) alkoxy, optionally substituted ($C_3$-$C_7$) cycloalkyl, optionally substituted ($C_3$-$C_7$) heterocyclic, optionally substituted aryl and a sulfur-containing moiety. In some embodiments, the sulfur containing moiety is —$SR_6$, wherein $R_6$ is selected from the group consisting of hydrogen, $C_1$-$C_6$ acyl, optionally substituted ($C_1$-$C_6$) alkyl, optionally substituted ($C_3$-$C_7$) cycloalkyl, optionally substituted ($C_3$-$C_7$) heterocyclic and optionally substituted aryl.

In some preferred embodiments of the aforementioned aspect of the present invention, the PARP inhibitor or metabolite thereof is a compound of formula II, its pharmaceutically acceptable salts or prodrugs thereof:

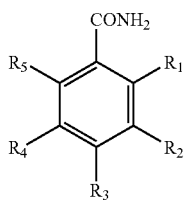

Formula II wherein, $R_1$, $R_3$, $R_4$, and $R_5$ are independently selected from the group consisting of hydrogen, hydroxy, optionally substituted amine, carboxyl, ester, nitroso, nitro, halogen, optionally substituted ($C_1$-$C_6$) alkyl, optionally substituted ($C_1$-$C_6$) alkoxy, optionally substituted ($C_3$-$C_7$) cycloalkyl, optionally substituted ($C_3$-$C_7$) heterocyclic, optionally substituted aryl and —$SR_6$; $R_2$ is either nitro or nitroso; and wherein at least two of the $R_1$, $R_3$, $R_4$, and $R_5$ substituents are always hydrogen; wherein $R_6$ is —$SR_6$, wherein $R_6$ is selected from the group consisting of hydrogen, $C_1$-$C_6$ acyl, optionally substituted ($C_1$-$C_6$) alkyl, optionally substituted ($C_3$-$C_7$) cycloalkyl, optionally substituted ($C_3$-$C_7$) heterocyclic and optionally substituted aryl and the optional substituents. In some embodiments $R_6$ is an optionally substituted ($C_1$-$C_6$) alkyl, which is a residue of an S-linked cysteine moiety, which may be a single cysteine amino acid or may form part of a dipeptide, tripeptide, tetrapeptide, pentapeptide or higher-order peptide containing cysteine as an amino acid.

In some preferred embodiments of the aforementioned aspect of the present invention, the PARP inhibitor is a compound of formula III, its pharmaceutically acceptable salts, metabolites or prodrugs thereof:

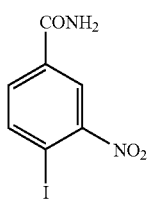

Formula III

In some embodiments of the aforementioned aspect of the present invention, the cancer is selected from the group consisting of colon adenocarcinoma, esophagus adenocarcinoma, liver hepatocellular carcinoma, squamous cell carcinoma, pancreas adenocarcinoma, islet cell tumor, rectum adenocarcinoma, gastrointestinal stromal tumor, stomach adenocarcinoma, adrenal cortical carcinoma, follicular carcinoma, papillary carcinoma, breast cancer, ductal carcinoma, lobular carcinoma, intraductal carcinoma, mucinous carcinoma, phyllodes tumor, ovarian adenocarcinoma, endometrium adenocarcinoma, granulose cell tumor, mucinous cystadenocarcinoma, cervix adenocarcinoma, vulva squamous cell carcinoma, basal cell carcinoma, prostate adenocarcinoma, giant cell tumor of bone, bone osteosarcoma, larynx carcinoma, lung adenocarcinoma, kidney carcinoma, urinary bladder carcinoma, Wilm's tumor, and lymphoma.

In some embodiments of the aforementioned aspect of the present invention, the treatment is selected from the group consisting of oral administration, transmucosal administration, buccal administration, nasal administration, inhalation, parental administration, intravenous, subcutaneous, intramuscular, sublingual, transdermal administration, and rectal administration.

In some embodiments of the aforementioned aspect of the present invention, the sample from the subject is selected from the group consisting of tumor tissue, hair, blood, cell, tissue, organ, brain tissue, blood, serum, sputum, saliva, plasma, nipple aspirant, synovial fluid, cerebrospinal fluid, sweat, urine, fecal matter, pancreatic fluid, trabecular fluid, cerebrospinal fluid, tears, bronchial lavage, swabbing, bronchial aspirant, semen, prostatic fluid, precervicular fluid, vaginal fluids, and pre-ejaculate.

Yet another aspect of the present invention relates to a method of monitoring a therapeutic effectiveness of a PARP inhibitor or metabolite thereof in a treatment of a disease comprising: (i) administering an effective amount of a PARP inhibitor or metabolite thereof to a patient to inhibit fatty acid synthesis; (ii) comparing a first and a second level of fatty acid in a first and second sample respectively, from the patient wherein the first level and the first sample are obtained prior to administration of the PARP inhibitor or metabolite thereof and the second level and the second sample are obtained after administration of the PARP inhibitor or metabolite thereof; and (iii) determining a therapeutic effectiveness of the PARP inhibitor or metabolite thereof in a treatment of a disease in the patient based on the comparison.

In some embodiments of the aforementioned aspect of the present invention, the inhibition of the fatty acid synthesis comprises inhibiting at least one enzyme of a glucose pathway or a fatty acid biosynthetic pathway. In some embodiments, when the second level of fatty acid in the second sample is lower than the first level of fatty acid in the first sample then the PARP inhibitor or metabolite thereof is therapeutically effective. In some embodiments, when the second level of fatty acid in the second sample is higher than the first level of fatty acid in the first sample then the PARP inhibitor or metabolite thereof is therapeutically ineffective. In some embodiments, the first level and the second level of fatty acid is determined by assay techniques. In some embodiments, the first level and the second level of fatty acid is determined by mass spectrometry. In some embodiments, the mass spectrometry is mass isotopomer distribution analysis.

In some embodiments of the aforementioned aspect of the present invention, the PARP inhibitor or metabolite thereof is a compound of formula I, its pharmaceutically acceptable salts or prodrugs thereof:

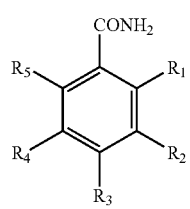

Formula I wherein, $R_1$, $R_2$, $R_3$, $R_4$, and $R_5$ are independently selected from the group consisting of hydrogen, hydroxy, optionally substituted amine, carboxyl, ester, nitroso, nitro, halogen, optionally substituted ($C_1$-$C_6$) alkyl, optionally substituted ($C_1$-$C_6$) alkoxy, optionally substituted ($C_3$-$C_7$) cycloalkyl, optionally substituted ($C_3$-$C_7$) heterocyclic, optionally substituted aryl and a sulfur-containing moiety. In some embodiments, the sulfur containing moiety is —$SR_6$, wherein $R_6$ is selected from the group consisting of hydrogen, $C_1$-$C_6$ acyl, optionally substituted ($C_1$-$C_6$) alkyl, optionally substituted ($C_3$-$C_7$) cycloalkyl, optionally substituted ($C_3$-$C_7$) heterocyclic and optionally substituted aryl.

In some embodiments of the aforementioned aspect of the present invention, the PARP inhibitor or metabolite thereof is a compound of formula II, its pharmaceutically acceptable salts or prodrugs thereof:

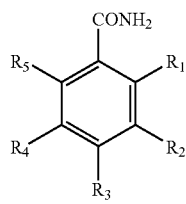

Formula II wherein, $R_1$, $R_3$, $R_4$, and $R_5$ are independently selected from the group consisting of hydrogen, hydroxy, optionally substituted amine, carboxyl, ester, nitroso, nitro, halogen, optionally substituted ($C_1$-$C_6$) alkyl, optionally substituted ($C_1$-$C_6$) alkoxy, optionally substituted ($C_3$-$C_7$) cycloalkyl, optionally substituted ($C_3$-$C_7$) heterocyclic, optionally substituted aryl and —$SR_6$; $R_2$ is either nitro or nitroso; and wherein at least two of the $R_1$, $R_3$, $R_4$, and $R_5$ substituents are always hydrogen; wherein $R_6$ is —$SR_6$, wherein $R_6$ is selected from the group consisting of hydrogen, $C_1$-$C_6$ acyl, optionally substituted ($C_1$-$C_6$) alkyl, optionally substituted ($C_3$-$C_7$) cycloalkyl, optionally substituted ($C_3$-$C_7$) heterocyclic and optionally substituted aryl and the optional substituents. In some embodiments $R_6$ is an optionally substituted ($C_1$-$C_6$) alkyl, which is a residue of an S-linked cysteine moiety, which may be a single cysteine amino acid or may form part of a dipeptide, tripeptide, tetrapeptide, pentapeptide or higher-order peptide containing cysteine as an amino acid.

In some embodiments of the aforementioned aspect of the present invention, the PARP inhibitor is a compound of formula III, its pharmaceutically acceptable salts or prodrugs thereof:

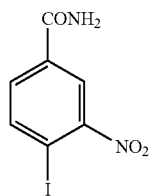

Formula III

In some embodiments of the aforementioned aspect of the present invention, the disease is cancer, cardiovascular, diabetes and obesity. In some embodiments, the administration is selected from the group consisting of oral administration, transmucosal administration, buccal administration, nasal administration, inhalation, parental administration, intravenous, subcutaneous, intramuscular, sublingual, transdermal administration, and rectal administration. In some embodiments, the first level of fatty acid in the first sample is determined from the patient's medical history.

Another aspect of the present invention relates to a method of treating a Her-2 related cancer comprising administering to a patient in need thereof an effective amount of a PARP inhibitor or metabolite thereof, wherein the PARP inhibitor or metabolite thereof inhibits a fatty acid synthesis. Yet another aspect of the present invention relates to a method of treating a Her-2 related cancer in a subject comprising: (i) determining a level of Her-2 expression in a sample from a subject, and (ii) administering an effective amount of a PARP inhibitor or metabolite thereof to the subject to inhibit fatty acid synthesis wherein the administration is based on the determination of the level of Her-2 expression, thereby treating the Her-2 related cancer in the subject.

In some embodiments of the aforementioned aspect of the present invention, the inhibition of the fatty acid synthesis comprises inhibiting at least one enzyme of a glucose pathway or a fatty acid biosynthetic pathway. In some embodiments, the inhibition of the fatty acid synthesis comprises inhibiting at least one enzyme of a fatty acid synthase wherein the enzyme is selected from the group consisting of acyl carrier protein, acetyl transferase, malonyl transferase, 3-keto-acyl-ACP synthase, 3-ketoacyl-ACP reductase, 3-hydroxy-acyl-ACP dehydratase, and enoyl-ACP reductase. In some embodiments, the level of Her-2 expression is up-regulated.

In some embodiments of the aforementioned aspect of the present invention, the PARP inhibitor or metabolite thereof is a compound of formula II, its pharmaceutically acceptable salts or prodrugs thereof:

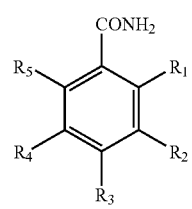

Formula II wherein, $R_1$, $R_3$, $R_4$, and $R_5$ are independently selected from the group consisting of hydrogen, hydroxy, optionally substituted amine, carboxyl, ester, nitroso, nitro, halogen, optionally substituted ($C_1$-$C_6$) alkyl, optionally substituted ($C_1$-$C_6$) alkoxy, optionally substituted ($C_3$-$C_7$) cycloalkyl, optionally substituted ($C_3$-$C_7$) heterocyclic, optionally substituted aryl and —$SR_6$; $R_2$ is either nitro or nitroso; and wherein at least two of the $R_1$, $R_3$, $R_4$, and $R_5$ substituents are always hydrogen; wherein $R_5$ is —$SR_6$, wherein $R_6$ is selected from the group consisting of hydrogen, $C_1$-$C_6$ acyl, optionally substituted ($C_1$-$C_6$) alkyl, optionally substituted ($C_3$-$C_7$) cycloalkyl, optionally substituted ($C_3$-$C_7$) heterocyclic and optionally substituted aryl and the optional substituents. In some embodiments $R_6$ is an optionally substituted ($C_1$-$C_6$) alkyl, which is a residue of an S-linked cysteine moiety, which may be a single cysteine amino acid or may form part of a dipeptide, tripeptide, tetrapeptide, pentapeptide or higher-order peptide containing cysteine as an amino acid.

In some preferred embodiments of the aforementioned aspect of the present invention, the PARP inhibitor is a compound of formula III, its pharmaceutically acceptable salts or prodrugs thereof:

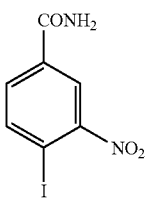

Formula III

In some embodiments of the aforementioned aspect of the present invention, the treatment is selected from the group consisting of oral administration, transmucosal administration, buccal administration, nasal administration, inhalation, parental administration, intravenous, subcutaneous, intramuscular, sublingual, transdermal administration, and rectal administration. In some embodiments, the sample comprises a cancer cell. In some embodiments, the method further comprises administering a Her-2 antibody. In some embodiments, the method further comprises surgery, radiation therapy, chemotherapy, gene therapy, immunotherapy, or a combination thereof.

Yet another aspect of the present invention relates to a method of treating a metabolic disease, comprising administering to a patient in need thereof an effective amount of a compound of formula II, its pharmaceutically acceptable salts or prodrugs thereof,

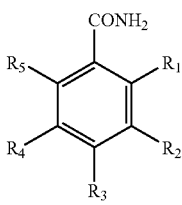

Formula II wherein, $R_1$, $R_3$, $R_4$, and $R_5$ are independently selected from the group consisting of hydrogen, hydroxy, optionally substituted amine, carboxyl, ester, nitroso, nitro, halogen, optionally substituted ($C_1$-$C_6$) alkyl, optionally substituted ($C_1$-$C_6$) alkoxy, optionally substituted ($C_3$-$C_7$) cycloalkyl, optionally substituted ($C_3$-$C_7$) heterocyclic, optionally substituted aryl and —$SR_6$; $R_2$ is either nitro or nitroso; and wherein at least two of the $R_1$, $R_3$, $R_4$, and $R_5$ substituents are always hydrogen; wherein $R_6$ is —$SR_6$, wherein $R_6$ is selected from the group consisting of hydrogen, $C_1$-$C_6$ acyl, optionally substituted ($C_1$-$C_6$) alkyl, optionally substituted ($C_3$-$C_7$) cycloalkyl, optionally substituted ($C_3$-$C_7$) heterocyclic and optionally substituted aryl and the optional substituents. In some embodiments $R_6$ is an optionally substituted ($C_1$-$C_6$) alkyl, which is a residue of an S-linked cysteine moiety, which may be a single cysteine amino acid or may form part of a dipeptide, tripeptide, tetrapeptide, pentapeptide or higher-order peptide containing cysteine as an amino acid. In some preferred embodiments, the compound of formula II, the pharmaceutically acceptable salts or the prodrugs thereof inhibits fatty acid synthesis, thereby treating the metabolic disease in the subject.

Yet another aspect of the present invention relates to a method of treating a cancer in a subject comprising: (i) determining a level of fatty acid in a sample from a subject, (ii) administering an effective amount of a compound of formula II, its pharmaceutically acceptable salts or prodrugs thereof, to the subject wherein the administration is based on the determination of the level of fatty acid, wherein the compound of formula II, its pharmaceutically acceptable salts or prodrugs thereof comprises:

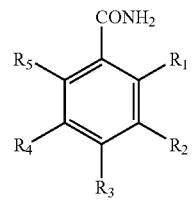

Formula II wherein, $R_1$, $R_3$, $R_4$, and $R_5$ are independently selected from the group consisting of hydrogen, hydroxy, optionally substituted amine, carboxyl, ester, nitroso, nitro, halogen, optionally substituted ($C_1$-$C_6$) alkyl, optionally substituted ($C_1$-$C_6$) alkoxy, optionally substituted ($C_3$-$C_7$) cycloalkyl, optionally substituted ($C_3$-$C_7$) heterocyclic, optionally substituted aryl and —$SR_6$; $R_2$ is either nitro or nitroso; and wherein at least two of the $R_1$, $R_3$, $R_4$, and $R_5$ substituents are always hydrogen; wherein $R_6$ is —$SR_6$, wherein $R_6$ is selected from the group consisting of hydrogen, $C_1$-$C_6$ acyl, optionally substituted ($C_1$-$C_6$) alkyl, optionally substituted ($C_3$-$C_7$) cycloalkyl, optionally substituted ($C_3$-$C_7$) heterocyclic and optionally substituted aryl and the optional substituents. In some embodiments $R_6$ is an optionally substituted ($C_1$-$C_6$) alkyl, which is a residue of an S-linked cysteine moiety, which may be a single cysteine amino acid or may form part of a dipeptide, tripeptide, tetrapeptide, pentapeptide or higher-order peptide containing cysteine as an amino acid. In some preferred embodiments, the compound of formula II, the pharmaceutically acceptable salts or the prodrugs thereof inhibit fatty acid synthesis, thereby treating the cancer in the subject.

In some embodiments of the aforementioned aspect of the present invention, the inhibition of the fatty acid synthesis comprises inhibiting at least one enzyme of a glucose pathway or a fatty acid biosynthetic pathway. In some embodiments, the inhibition of the fatty acid synthesis comprises inhibiting at least one enzyme of a fatty acid synthase wherein the enzyme is selected from the group consisting of acyl carrier protein, acetyl transferase, malonyl transferase, 3-keto-acyl-ACP synthase, 3-ketoacyl-ACP reductase, 3-hydroxy-acyl-ACP dehydratase, and enoyl-ACP reductase. In some embodiments, the compound of formula II, the pharmaceutically acceptable salts or the prodrugs thereof, comprises a compound of formula III, or a metabolite thereof:

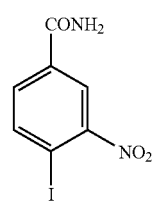

Formula III

In some embodiments of the aforementioned aspect of the present invention, the treatment is selected from the group consisting of oral administration, transmucosal administration, buccal administration, nasal administration, inhalation, parental administration, intravenous, subcutaneous, intramuscular, sublingual, transdermal administration, and rectal administration. In some embodiments, the metabolic disease is cardiovascular, diabetes or obesity. In some embodiments, the cancer is for example, Her-2 related cancer, colon adenocarcinoma, esophagus adenocarcinoma, liver hepatocellular carcinoma, squamous cell carcinoma, pancreas adenocarcinoma, islet cell tumor, rectum adenocarcinoma, gastrointestinal stromal tumor, stomach adenocarcinoma, adrenal cortical carcinoma, follicular carcinoma, papillary carcinoma, breast cancer, ductal carcinoma, lobular carcinoma, intraductal carcinoma, mucinous carcinoma, phyllodes tumor, ovarian adenocarcinoma, endometrium adenocarcinoma, granulose cell tumor, mucinous cystadenocarcinoma, cervix adenocarcinoma, vulva squamous cell carcinoma, basal cell carcinoma, prostate adenocarcinoma, giant cell tumor of bone, bone osteosarcoma, larynx carcinoma, lung adenocarcinoma, kidney carcinoma, urinary bladder carcinoma, Wilm's tumor, and lymphoma.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
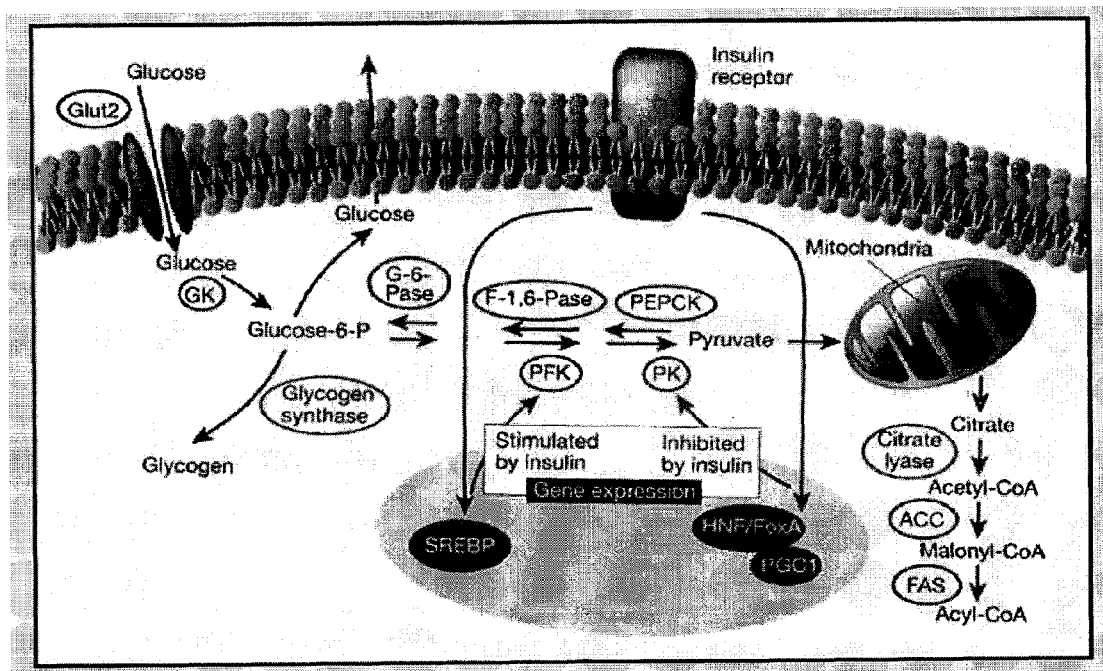
FIG. 1 depicts metabolic flux of a glucose pathway.

The term, "aryl" refers to optionally substituted mono- or bicyclic aromatic rings containing only carbon atoms. The term can also include phenyl group fused to a monocyclic cycloalkyl or monocyclic cycloheteroalkyl group in which the point of attachment is on an aromatic portion. Examples of aryl groups include, e.g., phenyl, naphthyl, indanyl, indenyl, tetrahydronaphthyl, 2,3-dihydrobenzofuranyl, dihydrobenzopyranyl, 1,4-benzodioxanyl, and the like.

The term, "heterocyclic" refers to an optionally substituted mono- or bicyclic aromatic ring containing at least one heteroatom (an atom other than carbon), such as N, O and S, with each ring containing about 5 to about 6 atoms. Examples of heterocyclic groups include, e.g., pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

The term "inhibit" or its grammatical equivalent, such as "inhibitory," is not intended to require complete reduction in a biological activity being considered such as, synthesis of fatty acid. Such reduction is preferably by at least about 50%, at least about 75%, at least about 90%, and more preferably by at least about 95% of the activity of the molecule in the absence of the inhibitory effect, e.g., in the absence of an inhibitor, such as PARP inhibitors disclosed in the invention. Most preferably, the term refers to an observable or measurable reduction in the synthesis of fatty acid. In treatment scenarios, preferably the inhibition is sufficient to produce a therapeutic and/or prophylactic benefit in the condition being treated.

The term "pharmaceutically acceptable salt" as used herein, means those salts which retain the biological effectiveness and properties of the compounds of the present invention, and which are not biologically or otherwise undesirable.

The term "subject" or its grammatical equivalents as used herein refers to a warm-blooded animal such as a mammal who is healthy or is afflicted with, or suspected to be afflicted with a disease. Preferably, "subject" refers to a human.

The term "treating" or its grammatical equivalents as used herein, means achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the compositions can be administered to a patient at risk of developing a particular disease, or to a patient reporting one or more of the physiological symptoms of a disease, even though a diagnosis of this disease can not have been made.

Definitions

"Nitrobenzamide precursor compound(s)" means a compound of the formula (Ia)

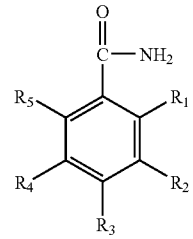

(Ia)

wherein $R_1$, $R_2$, $R_3$, $R_4$, and $R_5$ are, independently selected from the group consisting of hydrogen, hydroxy, amino, nitro, iodo, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, and pharmaceutically acceptable salts, solvates, isomers, tautomers, metabolites, analogs, or prodrugs thereof. $R_1$, $R_2$, $R_3$, $R_4$, and $R_5$ can also be a halide such as chloro, fluoro, or bromo. "Precursor compound" is a compound that undergoes one or more chemical or biochemical processes (e.g., in a cell or in an organism) that result in a metabolite compound. The terms "precursor", "precursor compound", "benzamide precursor" or "nitrobenzamide precursor" are used interchangeably herein.

"Metabolite" means a compound produced through any in vitro or in vivo metabolic process which results in a product that is different in structure than that of the starting compound. In other words, the term "metabolite" includes nitrobenzamide metabolite compounds. A metabolite can include a varying number or types of substituents that are present at any position relative to a precursor compound, such as the precursor compound depicted in the formula (Ia). In addition, a metabolite can vary in the number of types of substituents that are present at any position relative to the compounds described herein. In addition, the terms "metabolite", "metabolite compound", "benzamide metabolite compound" or "nitrobenzamide metabolite compound" are used interchangeably herein.

"Surgery" means any therapeutic or diagnostic procedure that involves methodical action of the hand or of the hand with an instrument, on the body of a human or other mammal, to produce a curative, remedial, or diagnostic effect.

"Radiation therapy" means exposing a patient to high-energy radiation, including without limitation x-rays, gamma rays, and neutrons. This type of therapy includes without limitation external-beam therapy, internal radiation therapy, implant radiation, brachytherapy, systemic radiation therapy, and radiotherapy.

"Chemotherapy" means the administration of one or more anti-cancer drugs and/or other agents to a cancer patient by various methods, including intravenous, oral, intramuscular, intraperitoneal, intravesical, subcutaneous, transdermal, buccal, or inhalation or in the form of a suppository. Chemotherapy may be given prior to surgery to shrink a large tumor prior to a surgical procedure to remove it, after surgery or radiation therapy to prevent the growth of any remaining cancer cells in the body.

The terms "effective amount" or "pharmaceutically effective amount" refer to a non-toxic but sufficient amount of the agent to provide the desired biological, therapeutic, and/or prophylactic result. That result can be reduction and/or alleviation of the signs, symptoms, or causes of a disease, or any other desired alteration of a biological system. For example, an "effective amount" for therapeutic uses is the amount of a nitrobenzamide metabolite compound as disclosed herein per se or a composition comprising the nitrobenzamide metabolite compound herein required to result in a clinically significant decrease in a disease. An appropriate effective amount in any individual case may be determined by one of ordinary skill in the art using routine experimentation.

The term "PARP inhibitor or metabolite thereof" includes compounds that are themselves PARP inhibitors as well as the active metabolites of those compounds. In some embodiments, said metabolites of PARP inhibitors are themselves PARP inhibitors, whether isolated or not. I some embodiments, said metabolites of PARP inhibitors are isolated and purified to a purity of at least 50%, at least 55%, at least 60%, at least 70%, at least 75%, at least 80%, at least 90%, at least 92%, at least 94%, at least 95%, at least 96%, at least 97%, at least 98%, at least 99%, at least 99.5%, at least 99.9% or purer, before being combined with one or more pharmaceutically acceptable ingredients to make a pharmaceutically acceptable dosage form as described in more detail herein. Metabolites of PARP inhibitors are metabolized forms of PARP inhibitor "precursor compounds" or "precursors," which are described in more detail herein.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

The term "treating" and its grammatical equivalents as used herein include achieving a therapeutic benefit and/or a prophylactic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder. For prophylactic benefit, a method of the invention may be performed on, or a composition of the invention administered to a patient at risk of developing cancer, or to a patient reporting one or more of the physiological symptoms of such conditions, even though a diagnosis of the condition may not have been made.

As used herein "BA" means 4-iodo-3-nitrobenzamide; "BNO" means 4-iodo-3-nitrosobenzamide; "BNHOH" means 4-iodo-3-hydroxyaminobenzamide.

Nitrobenzamide Metabolite Compounds

PARP inhibitors (Precursor compounds) useful in the present invention are of Formula (Ia)

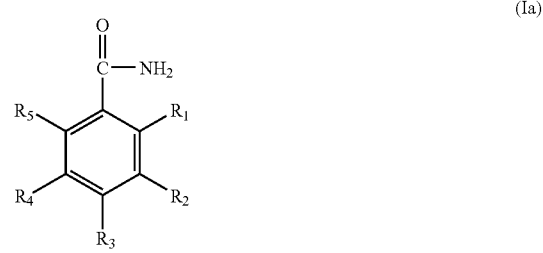

(Ia)

wherein $R_1$, $R_2$, $R_3$, $R_4$, and $R_5$ are, independently selected from the group consisting of hydrogen, hydroxy, amino, nitro, iodo, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, and pharmaceutically acceptable salts, solvates, isomers, tautomers, metabolites, analogs, or pro-drugs thereof. $R_1$, $R_2$, $R_3$, $R_4$, and $R_5$ can also be a halide such as chloro, fluoro, or bromo substituents.

A preferred (PARP inhibitor) precursor compound of formula Ia is:

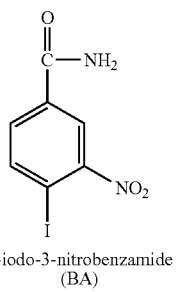

4-iodo-3-nitrobenzamide
(BA)

Metabolites of PARP inhibitors useful in the present invention are of the Formula (IIa):

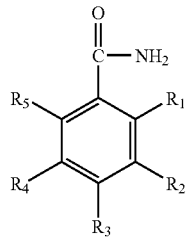

(IIa)

wherein either: (1) at least one of $R_1$, $R_2$, $R_3$, $R_4$, and $R_5$ substituent is always a sulfur-containing substituent, and the remaining substituents $R_1$, $R_2$, $R_3$, $R_4$, and $R_5$ are independently selected from the group consisting of hydrogen, hydroxy, amino, nitro, iodo, bromo, fluoro, chloro, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen; or (2) at least one of $R_1$, $R_2$, $R_3$, $R_4$, and $R_5$ substituents is not a sulfur-containing substituent and at least one of the five substituents $R_1$, $R_2$, $R_3$, $R_4$, and $R_5$ is always iodo, and wherein said iodo is always adjacent to a $R_1$, $R_2$, $R_3$, $R_4$, or $R_5$ group that is either a nitro, a nitroso, a hydroxyamino, hydroxy or an amino group; and pharmaceutically acceptable salts, solvates, isomers, tautomers, metabolites, analogs, or pro-drugs thereof. In some embodiments, the compounds of (2) are such that the iodo group is always adjacent a $R_1$, $R_2$, $R_3$, $R_4$ or $R_5$ group that is a nitroso, hydroxyamino, hydroxy or amino group. In some embodiments, the compounds of (2) are such that the iodo the iodo group is always adjacent a $R_1$, $R_2$, $R_3$, $R_4$ or $R_5$ group that is a nitroso, hydroxyamino, or amino group. In some embodiments, the sulfur-containing substituent is —$SR_6$, wherein $R_6$ is selected from the group consisting of hydrogen, $C_1$-$C_6$ acyl, optionally substituted ($C_1$-$C_6$) alkyl, optionally substituted ($C_3$-$C_7$) cycloalkyl, optionally substituted ($C_3$-$C_7$) heterocyclic and optionally substituted aryl.

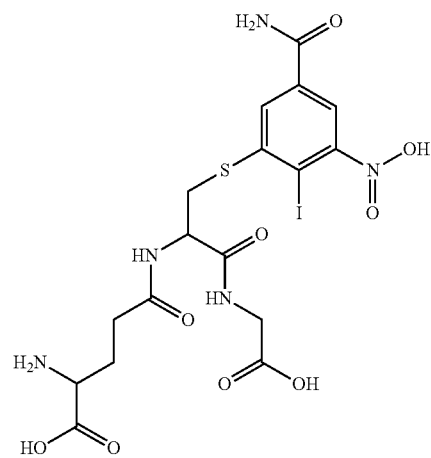

MS601

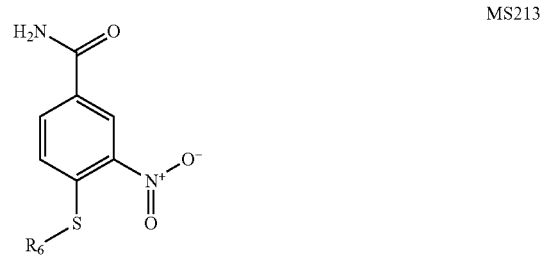

MS213

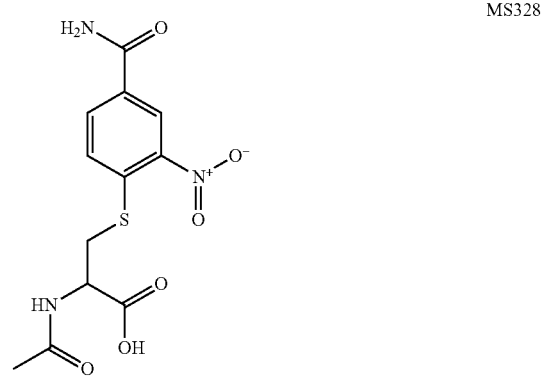

MS328

$R_6$ is selected from a group consisting of hydrogen, alkyl ($C_1$-$C_8$), alkoxy ($C_1$-$C_8$), isoquinolinones, indoles, thiazole, oxazole, oxadiazole, thiophene, or phenyl.

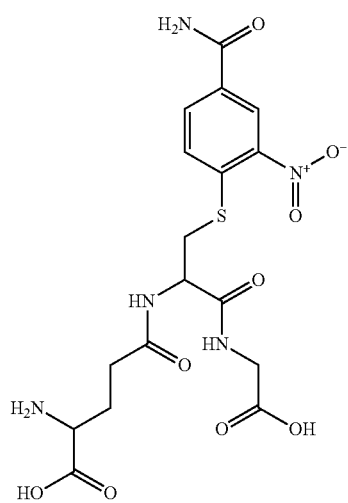

MS472

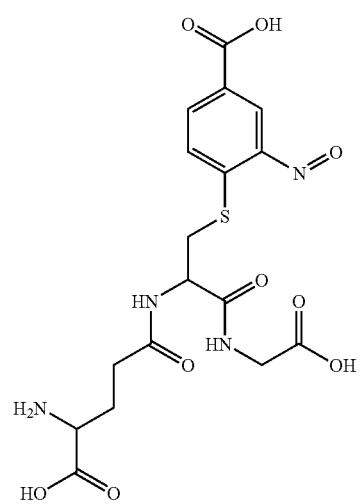

MS456

MS183
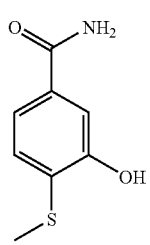
MS261
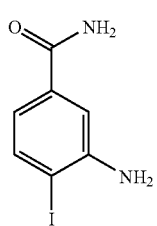
MS182
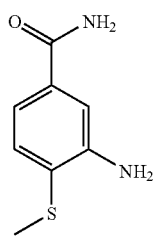
MS263
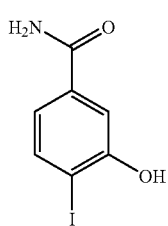
MS276
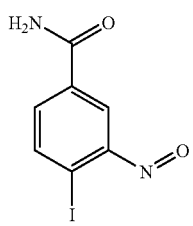
MS278
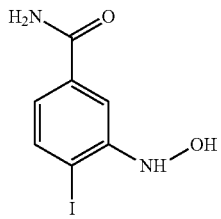
MS635a
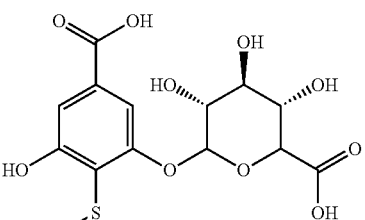
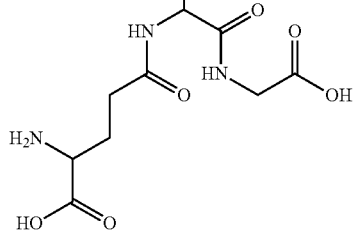
MS635b
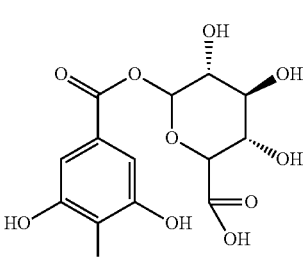
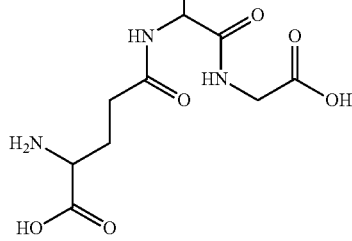
MS471
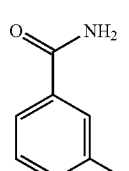
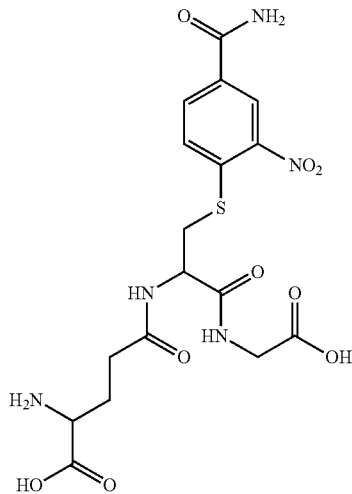

-continued
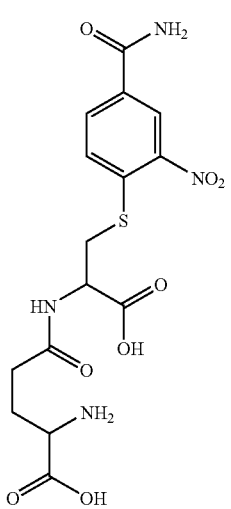
MS414
MS692
While not being limited to any one particular mechanism, the following provides an example for MS292 metabolism via a nitroreductase or glutathione conjugation mechanism:
Nitroreductase Mechanism
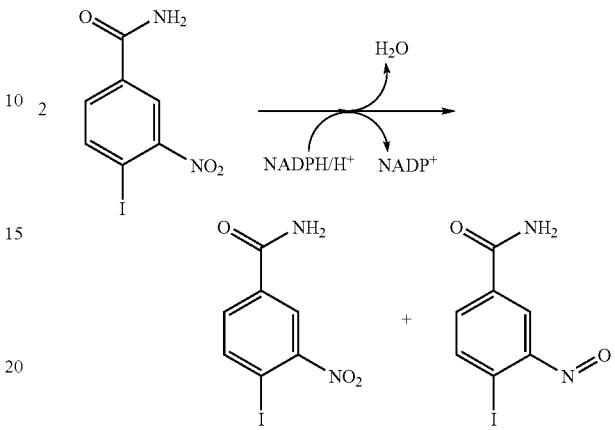
BA Glutathione Conjugation and Metabolism:
Glutathione conjugation and metabolism
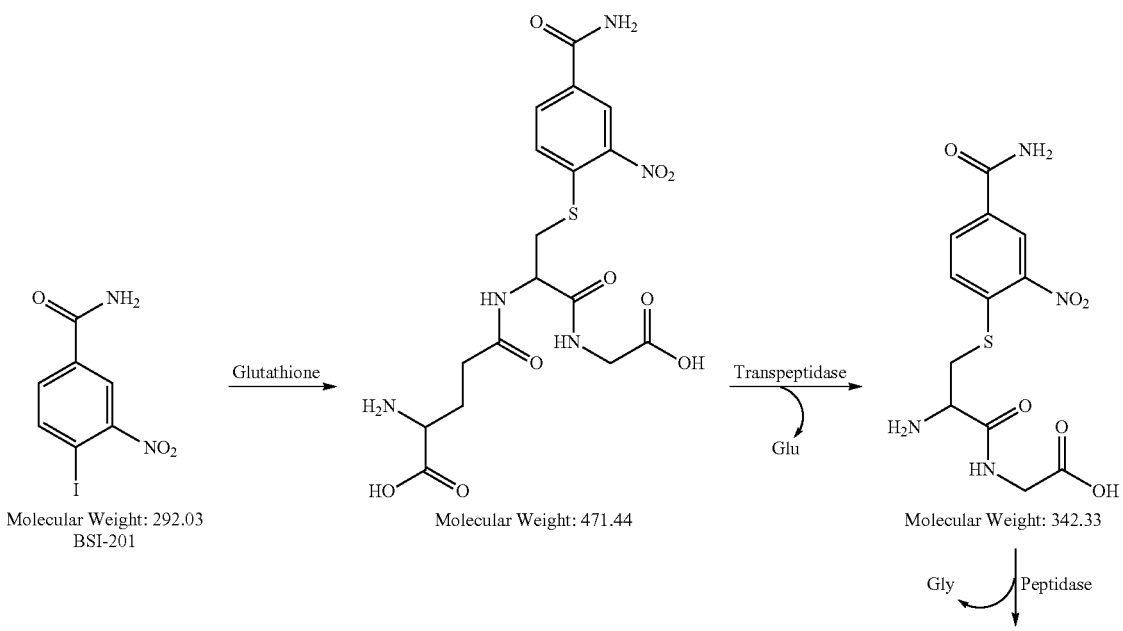

-continued

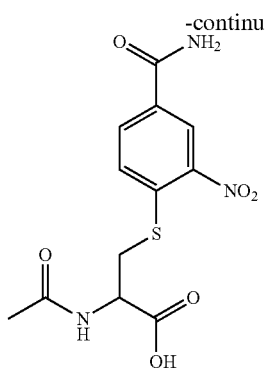

Molecular Weight: 327.31

⇌ N-acetyltransferase
HSCoA   CH₃COSCoA

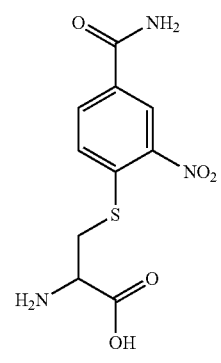

Molecular Weight: 285.28

The present invention provides for the use of the aforesaid nitrobenzamide metabolite compounds for the treatment of other breast cancers including a ductal carcinoma in a mammary gland, other forms of leukemia including acute promyelocytic leukemia in peripheral blood, ovarian cancer, lung cancer, bladder cancer, prostate cancer, pancreatic cancer, and cervical cancer, as well as other cancer types described herein.

It has been reported that nitrobenzamide metabolite compounds have selective cytotoxicity upon malignant cancer cells but not upon non-malignant cancer cells. See Rice et al., Proc. Natl. Acad. Sci. USA 89:7703-7707 (1992). In one embodiment, the nitrobenzamide metabolite compounds utilized in the methods of the present invention may exhibit more selective toxicity towards tumor cells than non-tumor cells.

One aspect of the present invention provides methods of treating fatty acid synthesis related diseases by administering an effective amount of a poly(ADP)ribose polymerase enzyme (PARP) inhibitor wherein the PARP inhibitor inhibits fatty acid synthesis. Fatty acid synthesis relate diseases include, but are not limited to cancer, diabetes, obesity, Niemann-Pick disease, Gaucher's disease, metachromatic leukodystrophy, Fabry's disease, hyaline membrane disease, Tay-Sachs disease, Sandhoff diseases, Krabbe's disease, fucosidosis, sulfatide lipodosis, and Farber's lipogranulomatosis. The fatty acid synthesis related diseases includes diseases with abnormality in fatty acid metabolism.

Fatty acid synthesis is also related to inflammation (predominantly those of the joints, skin and eyes), reproductive function (including the induction of labor), inhibiting gastric acid secretion, regulating blood pressure through vasodilation or constriction, and inhibiting or activating platelet aggregation and thrombosis. In some preferred embodiments, the fatty acid synthesis related diseases include obesity, diabetes, or cardiovascular disease.

Another aspect of the present invention relates to methods for treatment of cancer in a subject by administering an effective amount of a PARP inhibitor or metabolite thereof wherein the PARP inhibitor or metabolite thereof inhibits fatty acid synthesis. The methods particularly relate to treating a cancer in a subject by identifying a level of a fatty acid in a sample of a subject, and administering an effective amount of a PARP inhibitor or metabolite thereof to inhibit fatty acid synthesis where the administration is based on the level of fatty acid, thereby treating the cancer in the subject.

The test sample can be used directly as obtained from the source or following a pretreatment to modify the character of the sample. The sample can be derived from any biological source, such as tissues or extracts, including cells, and physiological fluids, such as, for example, whole blood, plasma, serum, saliva, ocular lens fluid, cerebrospinal fluid, sweat, urine, milk, ascots fluid, synovial fluid, peritoneal fluid and the like. The sample is obtained from animals or humans, preferably from humans. The sample can be treated prior to use, such as preparing plasma from blood, diluting viscous fluids, and the like. Methods of treating a sample can involve filtration, distillation, extraction, concentration, inactivation of interfering components, the addition of reagents, and the like.

Typically, in normal humans, the fatty acid biosynthetic pathway is down-regulated and most of the fatty acid in the body comes from dietary fat. However, in humans suffering from cancer, fatty acid biosynthetic pathway is up-regulated resulting in elevated levels of fatty acid in the tumor tissues. The up-regulated fatty acid synthesis in various cancers suggests that fatty acid synthesis provides an advantage for tumor growth. The inhibition of fatty acid synthesis can result in depletion of the membrane lipids, which can cause cell death (Khaddar et al. Proc. Natl. Acad. Sic. 1994, vol. 91, p. 6379-6383). The present invention provides treatment of cancer with an effective amount of a PARP inhibitor or metabolite thereof wherein the PARP inhibitor or metabolite thereof inhibits the fatty acid synthesis. Various cancers include but are not limited to, bladder, breast, colon, rectum, prostate, ovary, salivary gland, skin adnexae, bile duct, endocervix, ectocervix, vagina, esophagus, nasopharynx, oropharynx, or those of germ cell origin, carcinomas or adenocarcinomas of the stomach, endometrium, kidney, liver and lung, melanoma and mesothelioma.

In some embodiments of the present invention, the method includes treatment of Her-2 related cancer by administering an effective amount of a PARP inhibitor or metabolite thereof wherein the PARP inhibitor or metabolite thereof inhibits a fatty acid synthesis. Not intending to limit the scope of the present invention, the fatty acid synthase (FAS)-catalyzed de novo fatty acid biosynthesis may contribute to the cancer phenotype by virtue of its ability to specifically regulate the expression and activity of Her-2/neu (erbB-2) oncogene (Menendez J A et al. Drug News Perspect. 2005, 18(6), 375-85; Menendez J A et al. J. Cell Biochem. 2005, 94(5), 857-63). The inhibition of the fatty acid synthesis by the PARP inhibitor or metabolite thereof can result in treatment of Her-2 related cancer.

In some embodiments of the present invention, the method of treatment of Her-2 related cancer includes determining a level of Her-2 expression in a sample from a subject and administering an effective amount of a PARP inhibitor or metabolite thereof to the subject to inhibit fatty acid synthesis wherein the administration is based on the determination of the level of Her-2 expression in the sample from the subject. In some preferred embodiments, the sample comprises a cancer cell. If the level of Her-2 expression in the sample is higher then the patient is treated with an effective amount of the PARP inhibitor or metabolite thereof. Without limiting the scope of the present invention the PARP inhibitor or metabolite thereof inhibits fatty acid synthesis and thereby treats a Her-2 related cancer. In some embodiments, the PARP inhibitor or metabolite thereof inhibits fatty acid synthesis by inhibiting one or more enzymes of a glucose pathway or a fatty acid biosynthetic pathway. In some embodiments, the PARP inhibitor or metabolite thereof is administered in combination with a Her-2 antibody. An example of a Her-2 antibody is herceptin.

In some preferred embodiments, the methods include treatment of obesity by administering an effective amount of a PARP inhibitor or metabolite thereof wherein the PARP inhibitor or metabolite thereof inhibits a fatty acid synthesis. Obesity is a major health problem that is becoming more common among adults and increasing rapidly in children and adolescents. Obesity has been linked to a broad range of physical, emotional and socioeconomic problems. The method of the present invention for reducing obesity, are applicable to humans and other animals including vertebrates, especially mammals. Animals include poultry, swine, cattle, sheep, and other animals where reduction in fat accumulation without reduction in muscle mass can be desirable for veterinary health or economic reasons. The PARP inhibitors can be administered in accordance with the methods of the present invention to dogs, cats, horses and other animals for veterinary health reasons.

In some preferred embodiments of the present invention the methods include treatment of cardiovascular disease by administering an effective amount of a PARP inhibitor or metabolite thereof wherein the PARP inhibitor or metabolite thereof inhibits a fatty acid synthesis. In some people excess body fat causes an increased risk for vascular disease, including heart disease and stroke. Increased fat stored in intra-abdominal deposits can be associated with, and can cause, an increase in risk factors for atherosclerotic cardiovascular disease (ASCVD). The risk factors for ASCVD include: hypertension, elevated levels of cholesterol, particularly LDL-cholesterol, in the blood, diabetes and hyperglycemia. People with hypertension are likely to develop impaired glucose tolerance, a type of pre-diabetes.

In some preferred embodiments, the methods include treatment of diabetes by administering an effective amount of a PARP inhibitor or metabolite thereof wherein the PARP inhibitor or metabolite thereof inhibits a fatty acid synthesis. Patients suffering from diabetes can have any of several lipid abnormalities. Common lipid profiles in the patient with diabetes include, elevated levels of triglycerides, low-density lipoproteins (LDL), and very low-density lipoproteins (VLDL), along with lower than normal levels of high-density lipoprotein (HDL). The combined effect of these factors results in promotion of atherosclerosis and thrombosis. Other diseases include, but are not limited to, hyperinsulinemia, insulin resistance, myocardial infarction, fatty liver, polycystic ovarian syndrome, hemochromatosis, non-alcoholic steatohepatitis, diabetic kidney disease, etc.

While it is preferred that the level of the fatty acid in a subject is determined prior to the treatment with PARP inhibitors or metabolites thereof, the skilled clinician will recognize that such determination is not always necessary. The reduction of the tumor burden after the treatment of a cancer patient with a PARP inhibitor or metabolite thereof would demonstrate the presence of elevated levels of fatty acid in the tumor before the treatment. Where a cancer patient can be successfully treated by the method of this invention, independent determination of a level of fatty acid in a subject can be unnecessary. Such empirical treatment of cancer of the type usually found to express elevated levels of fatty acid is also within the scope of the present invention.

Another aspect of the present invention relates to a method of monitoring a therapeutic effectiveness of a PARP inhibitor or metabolite thereof in a treatment of a disease by administering an effective amount of a PARP inhibitor or metabolite thereof to a patient to inhibit fatty acid synthesis; comparing a first and a second level of fatty acid in a first and second sample from the patient wherein the first level and the first sample are obtained prior to administration of the PARP inhibitor or metabolite thereof and the second level and the second sample are obtained after administration of the PARP inhibitor or metabolite thereof; and determining a therapeutic effectiveness of the PARP inhibitor or metabolite thereof in a treatment of a disease in the patient based on the comparison.

The first level of the fatty acid from the first sample can be determined just before the administration of the PARP inhibitor or metabolite thereof to the patient or can be obtained day/s before, week/s before, month/s before, or year/s before the administration of the PARP inhibitor or metabolite thereof to the patient. The first level from first sample can be obtained from a medical history of the patient. The second level of the fatty acid from the second sample can be found to be lower than the first level of the fatty acid from the first sample thereby indicating the inhibition of the fatty acid synthesis in the patient by the PARP inhibitor or metabolite thereof and hence indicating the therapeutic effectiveness of the PARP inhibitor or metabolite thereof. The second level of the fatty acid from the second sample can be found to be higher than the first level of the fatty acid from the first sample and may thereby indicate the less therapeutic effectiveness of the PARP inhibitor or metabolite thereof. Such monitoring of the therapeutic effectiveness of the PARP inhibitor or metabolite thereof can be useful in adjusting the dosage and personalizing the dosing regimen for the patient. Such monitoring can also be used in clinical trials.

The inhibition of fatty acid synthesis in the methods of the present invention can involve inhibition of one or more enzymes of a glucose pathway or a fatty acid biosynthetic pathway. Without limiting the scope of the present invention, various steps and the enzymes involved in the glucose pathway and the fatty acid biosynthetic pathway are disclosed herein. Any one or more of the steps and/or the enzymes can be inhibited by the PARP inhibitors or metabolites thereof of the present invention.

Glucose Pathway

Figure 2:
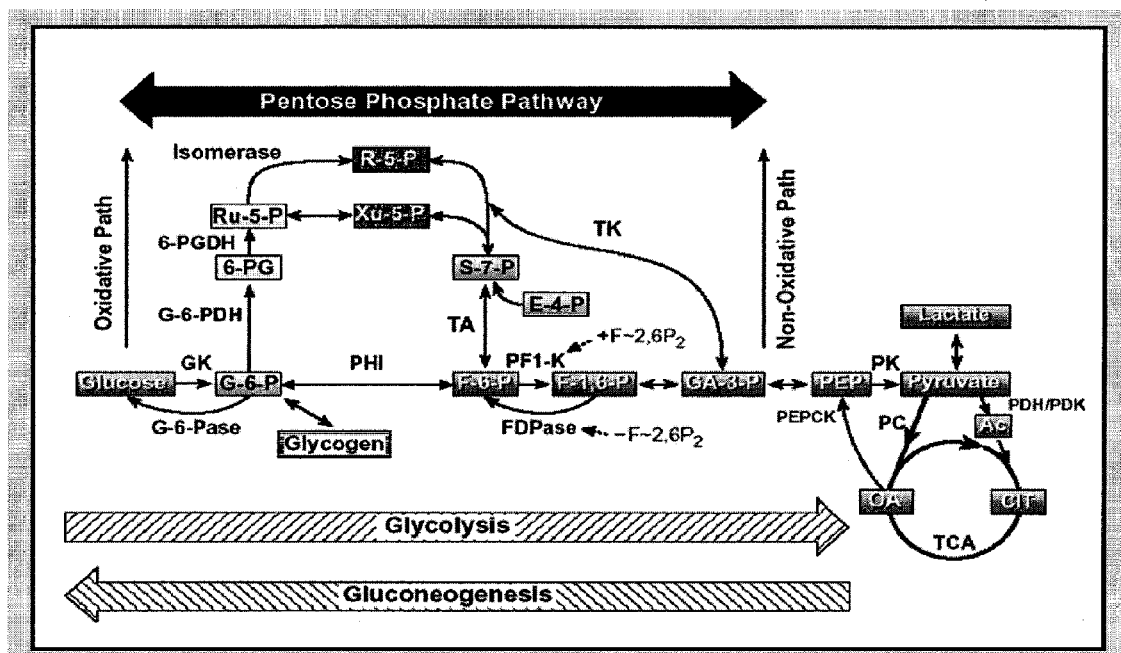
FIG. 2 depicts pentose and futile cycles of a glucose pathway.

Oxidation of glucose is known as glycolysis where glucose is oxidized to either lactate or pyruvate. Under aerobic conditions, the product in most tissues is pyruvate and the pathway is known as aerobic glycolysis. When oxygen is depleted, as for instance during prolonged vigorous exercise, the dominant glycolytic product in many tissues is lactate and the process is known as anaerobic glycolysis. The pathway of glycolysis can be seen as consisting of 2 separate phases. In the first phase, 2 equivalents of ATP are used to convert glucose to fructose 1,6-bisphosphate (F1,6BP). In the second phase F1,6BP is degraded to pyruvate, with the production of 4 equivalents of ATP and 2 equivalents of NADH (see FIGS. 1 and 2).

The ATP-dependent phosphorylation of glucose to form glucose 6-phosphate (G6P) is the first reaction of glycolysis, and is catalyzed by tissue-specific isoenzymes known as hexokinases. Four mammalian isozymes of hexokinase are known (types I-IV), with the type IV isozyme often referred to as glucokinase. Glucokinase is the form of the enzyme found in hepatocytes. The regulation of hexokinase and glucokinase activities is also different. Hexokinases I, II, and III are allosterically inhibited by product (G6P) accumulation, whereas glucokinases are not. The latter further insures liver accumulation of glucose stores during times of glucose excess, while favoring peripheral glucose utilization when glucose is required to supply energy to peripheral tissues.

The second reaction of glycolysis is an isomerization, in which G6P is converted to fructose 6-phosphate (F6P). The enzyme catalyzing this reaction is phosphohexose isomerase (also known as phosphoglucose isomerase). The next reaction of glycolysis involves the utilization of a second ATP to convert F6P to fructose 1,6-bisphosphate (F1,6BP). This reaction is catalyzed by 6-phosphofructo-1-kinase, better known as phosphofructokinase-1 or PFK-1. Fructose units readily flow in the reverse (gluconeogenic) direction because of the ubiquitous presence of the hydrolytic enzyme, fructose-1,6-bisphosphatase (F-1,6-BPase). The presence of these two enzymes in the same cell compartment provides an example of a metabolic futile cycle, which if unregulated would rapidly deplete cell energy stores. However, the activity of these two enzymes is so highly regulated that PFK-1 is considered to be the rate-limiting enzyme of glycolysis and F-1,6-BPase is considered to be the rate-limiting enzyme in gluconeogenesis.

Aldolase catalyses the hydrolysis of F1,6BP into two 3-carbon products: dihydroxyacetone phosphate (DHAP) and glyceraldehyde 3-phosphate (G3P). The aldolase reaction proceeds readily in the reverse direction, being utilized for both glycolysis and gluconeogenesis. The two products of the aldolase reaction equilibrate readily in a reaction catalyzed by triose phosphate isomerase. Succeeding reactions of glycolysis utilize G3P as a substrate; thus, the aldolase reaction is pulled in the glycolytic direction by mass action principals.

The second phase of glucose catabolism features the energy-yielding glycolytic reactions that produce ATP and NADH. In the first of these reactions, glyceraldehyde-3-P dehydrogenase (G3PDH) catalyzes the $NAD^+$-dependent oxidation of G3P to 1,3-bisphosphoglycerate (1,3BPG) and NADH. The G3PDH reaction is reversible, and the same enzyme catalyzes the reverse reaction during gluconeogenesis.

The high-energy phosphate of 1,3-BPG is used to form ATP and 3-phosphoglycerate (3PG) by the enzyme phosphoglycerate kinase. Associated with the phosphoglycerate kinase pathway is an important reaction of erythrocytes, the formation of 2,3-bisphosphoglycerate, 2,3BPG by the enzyme bisphosphoglycerate mutase. 2,3BPG is an important regulator of hemoglobin's affinity for oxygen. The 2,3-bisphosphoglycerate phosphatase degrades 2,3BPG to 3-phosphoglycerate, a normal intermediate of glycolysis. The 2,3BPG shunt thus operates with the expenditure of 1 equivalent of ATP per triose passed through the shunt.

The remaining reactions of glycolysis are aimed at converting the 3PG to 2PG by phosphoglycerate mutase and the 2PG conversion to phosphoenoylpyruvate (PEP) is catalyzed by enolase. The final reaction of aerobic glycolysis is catalyzed by the highly regulated enzyme pyruvate kinase (PK). In this exergonic reaction, the high-energy phosphate of PEP is conserved as ATP. The loss of phosphate by PEP leads to the production of pyruvate in an unstable enol form, which spontaneously tautomerizes to the more stable, keto form of pyruvate. Under anaerobic conditions and in erythrocytes under aerobic conditions, pyruvate is converted to lactate by the enzyme lactate dehydrogenase (LDH), and the lactate is transported out of the cell into the circulation.

Under aerobic conditions, pyruvate in most cells is further metabolized via the TCA cycle. Pyruvate is preferentially oxidized to $CO_2$ and $H_2O$ in the TCA cycle. When transported into the mitochondrion, pyruvate encounters two principal metabolizing enzymes: pyruvate carboxylase (a gluconeogenic enzyme) and pyruvate dehydrogenase (PDH), the first enzyme of the PDH complex. When the energy charge is low, CoA is not acylated, pyruvate carboxylase is inactive, and pyruvate is preferentially metabolized via the PDH complex and the enzymes of the TCA cycle to $CO_2$ and $H_2O$. The PDH complex is comprised of multiple copies of 3 separate enzymes: pyruvate dehydrogenase (20-30 copies), dihydrolipoyl transacetylase (60 copies) and dihydrolipoyl dehydrogenase (6 copies). The complex also requires 5 different coenzymes: CoA, $NAD^+$, $FAD^+$, lipoic acid and thiamine pyrophosphate (TPP). The net result of the reactions of the PDH complex are:

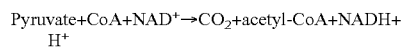

Pyruvate+CoA+$NAD^+$→$CO_2$+acetyl-CoA+NADH+$H^+$

The reactions of the PDH complex serve to interconnect the metabolic pathways of glycolysis, gluconeogenesis and fatty acid synthesis to the TCA cycle.

Fatty Acid Biosynthetic Pathway

Fatty acids are synthesized by fatty acid synthase (FAS) using the substrates acetyl CoA, malonyl CoA and NADPH. Thus, the fatty acid synthesis pathway is usually considered to involve four enzymes, FAS and the three enzymes which produce its substrates: acetyl CoA carboxylase (ACC), malic enzyme and citrate lyase. Other enzymes which can feed substrates into the pathway, such as the enzymes which produce NADPH via the hexose monophosphate shunt, can also affect the rate of fatty acid synthesis, and thus in cells that depend on endogenously synthesized fatty acid. Inhibition of the expression or the activity of any of these enzymes can affect growth of cancer cells that are dependent on endogenously synthesized fatty acid.

The synthesis of malonyl-CoA is the first step of fatty acid synthesis and the enzyme that catalyzes this reaction, acetyl-CoA carboxylase (ACC), is the site of regulation of fatty acid synthesis. Like other enzymes that transfer $CO_2$ to substrates, ACC requires a biotin co-factor. The synthesis of fatty acids from acetyl-CoA and malonyl-CoA is carried out by fatty acid synthase, FAS. The active enzyme is a dimer of identical subunits.

All of the reactions of fatty acid synthesis are carried out by the multiple enzymatic activities of FAS. Like fat oxidation, fat synthesis involves 4 enzymatic activities. These are β-keto-ACP synthase, β-keto-ACP reductase, 3-OH acyl-ACP dehydratase and enoyl-CoA reductase. The two reduction reactions require NADPH oxidation to $NADP^+$. The primary fatty acid synthesized by FAS is palmitate.

Palmitate is a 16:0 fatty acid, i.e. 16 carbons and no sites of unsaturation. Palmitate is then released from the enzyme and can then undergo separate elongation and/or unsaturation to yield other fatty acid molecules. Elongation and unsaturation of fatty acids occurs in both the mitochondria and endoplasmic reticulum (microsomal membranes). The predominant site of these processes is in the ER membranes. Elongation involves condensation of acyl-CoA groups with malonyl-CoA. The resultant product is two carbons longer ($CO_2$ is released from malonyl-CoA as in the FAS reaction) which undergoes reduction, dehydration and reduction yielding a saturated fatty acid. The reduction reactions of elongation require NADPH as co-factor just as for the similar reactions catalyzed by FAS. Mitochondrial elongation involves acetyl-CoA units and is a reversal of oxidation except that the final reduction utilizes NADPH instead of $FADH_2$ as co-factor.

Desaturation occurs in the ER membranes as well and in mammalian cells and involves 4 broad specificity fatty acyl-CoA desaturases (non-heme iron containing enzymes). These enzymes introduce unsaturation at $C_4$, $C_5$, $C_6$ or $C_9$. The electrons transferred from the oxidized fatty acids during desaturation are transferred from the desaturases to cytochrome b5 and then NADH-cytochrome b5 reductase. Some of the saturated fatty acids include, but are not limited to, lauric acid (C:12), myristic acid (C:14), palmitic acid (C:16), stearic acid (C:18), oleic acid (C:18-1), arachidic acid (C:20), C:22 and C:24. Some of the unsaturated acids include, but are not limited to, docosahexaenoic acid, eicosapentaenoic acid, arachidonic acid, oleic acid, and erucic acid.

Analysis Techniques

The determination of the level of fatty acid in a sample of a subject or the determination of the inhibition of fatty acid synthesis after treatment with PARP inhibitor or metabolite thereof can involve various detection techniques known in the art including but not limited to, enzyme assays, mass spectrometry such as gas chromatography/mass spectrometry (GC/MS), mass selective detector analysis (MSD), chemical ionization and selected monitoring (SIM), mass isotopomer distribution analysis (MIDA), high performance liquid chromatography (HPLC) or nuclear magnetic resonance (NMR).

The determination of inhibition of fatty acid synthesis after treatment of a subject with an effective amount of a PARP inhibitor or metabolite thereof can involve analyzing various metabolites or the molecular fluxes of the glucose or the fatty acid biosynthetic pathway in a sample from the subject. The determination can involve one or more comparisons with reference samples. The reference samples are typically obtained from the same subject or from a different subject who is either not affected with the disease (such as, normal subject) or is a patient. The reference sample could be obtained from one subject, multiple subjects or could be synthetically generated. The identification can also involve the comparison of the identification data with the databases. One embodiment of the invention relates to identifying the level of fatty acid in a subject afflicted with a disease, such as cancer and correlating it with the fatty acid level of the normal subjects. If the level of the fatty acid is up-regulated in the subject afflicted with the disease then the subject is treated with an effective amount of PARP inhibitor or metabolite thereof that inhibits the synthesis of the fatty acid.

In some embodiments, the step of comparison the level of fatty acid is performed by a software algorithm. Preferably, the data generated is transformed into computer readable form; and an algorithm is executed that classifies the data according to user input parameters, for detecting signals that represent level of fatty acid in diseased patients and level of fatty acid in normal subjects.

The metabolites of the glucose or the fatty acid biosynthetic pathway that can be analyzed in the methods of the present invention include but are not limited to, fatty acid or its metabolites, enzymes, glucose, glutamate, glycogen, lactate, $CO_2$, acetyl Co-A, RNA ribose and DNA deoxyribose. The molecular fluxes of the glucose or fatty acid biosynthetic pathway include, but are not limited to, glucose uptake from culture media; lactate production from glucose (anaerobic glycolysis); $^{13}CO_2$ release from glucose via TCA cycle; TCA cycle anaplerotic flux; glycogen synthesis; de novo fatty acid synthesis, elongation, desaturation and acetyl-CoA synthesis; and pentose cycle-RNA and DNA ribose synthesis via oxidative and non-oxidative reactions. The metabolites can be chemically derivatized after extraction and before analysis. The analyzing techniques are well known in the art and are within the scope of the present invention.

The assay techniques include activity assays or stains, immunoassays using antibodies, assays measuring enzyme mRNA such as FAS mRNA, and the like. Expression of the enzymes involved in the glucose pathway or the fatty acid biosynthetic pathway can be determined directly in tumor tissue samples obtained through procedures such as biopsies, resections or needle aspirates, using assays such as immunohistochemistry, cytosol enzyme immunoassay or radioimmunoassay, in situ hybridization of nucleic acid probes with mRNA targets, or direct measurement of enzyme activity. Expression of the enzymes can be indirectly measured in biological fluid samples obtained from subjects, such as blood, urine, serum, lymph, saliva, semen, ascites, or especially plasma, using any suitable assays. Preferred assays include enzyme immunoassay or radioimmunoassay.

In some embodiments, the therapeutic effect of a PARP inhibitor or metabolite thereof on a cell, tissue, or organism can be determined by analyzing the rates of synthesis or removal of a plurality of metabolites such as fatty acids in the cell, tissue, or organism after the administration of an effective amount of the PARP inhibitor or metabolite thereof. By this method, the inhibition of the fatty acid synthesis by the PARP inhibitor or metabolite thereof can be monitored.

In some preferred embodiments of the present invention, the metabolites or the molecular fluxes of the glucose or the fatty acid biosynthetic pathway are analyzed by mass isotopomer distribution analysis (MIDA). In some embodiments, a molecular flux rate of a plurality of metabolites in all or a portion of a cell, tissue or organism is analyzed. One or more isotope-labeled metabolites or metabolite precursors are administered to the cell, tissue or organism for a period of time sufficient for one or more isotope labels to be incorporated into a plurality of metabolites in the cell, tissue or organism. A media or a cell pellet is collected from the cell, tissue, or organism. A plurality of mass isotopomeric envelopes of ions representing individual metabolites in the cell pellet or the media are identified by mass spectrometry. In addition, the relative and absolute mass isotopomer abundances of the ions within the isotopic envelopes corresponding to each identified metabolite are quantified by mass spectrometry. These relative and absolute mass isotopomer abundances allow the rates of synthesis or removal of each identified metabolite to be calculated, and the molecular flux rates of the plurality of metabolites thereby to be determined. In some embodiments, the metabolites can be derivatized prior to introduction into the mass spectrometer. The derivatization can be any method known in the art, such as biochemically degrading the metabolites or chemically altering the metabolites.

Isotopic labels include specific heavy isotopes of elements, present in biomolecules, such as $^2H$, $^{13}C$, $^{15}N$, $^{18}O$, $^{35}S$, $^{34}S$, or can contain other isotopes of elements present in biomolecules, such as $^3H$, $^{14}C$, $^{35}S$, $^{125}I$, $^{131}I$. Isotope labeled metabolites include but are not limited to, $^2H_2O$, $^{15}NH_3$, $^{13}CO_2$, $H^{13}CO_3$, $^2H$-labeled amino acids, $^{13}C$-labeled amino acids, $^{15}N$-labeled amino adds, $^{18}O$-labeled amino acids, $^{33}S$ or $^{34}S$-labeled amino acids, $^3H_2O$, $^3H$-labeled amino adds, $^{14}C$-labeled amino acids, $^{14}CO_2$, and $H^{14}CO_2$ etc.

Metabolic flux estimation deals with uncovering the steady-state velocities of biochemical reactions in vivo. The knowledge of the fluxes helps in the optimization of the metabolic pathways towards high yield of the product metabolite of interest. The use of $^{13}$C-labeled substrate is a method to quantify intracellular fluxes of the cell when there is more than one alternative pathway between two metabolites. In the present invention, [1, 2$^{13}$C$_2$]-D-glucose is used in the media as the only source of glucose. The tracing methods are based on measuring the isotopomer distributions, that is, the different $^{13}$C-isotopic versions of the metabolite with their relative abundances. By comparing the measured isotopomer distribution to the distributions expected when using each alternative pathway, the information about the distribution of the fluxes among the pathways can be deduced.

There are two methods to determine the positional isotopomer distribution of the atoms, nuclear magnetic resonance (NMR) and mass spectrometry (MS). MS can be coupled with liquid (LC-MS) or gas (GC-MS) chromatographic separation. The methods also can be combined to gain more information about the positional isotopomer distribution and thus about the fluxes as well. In some preferred embodiments of the present invention, the isotopomer distribution of the atoms and the metabolic fluxes are determined by mass spectrometry. The mass spectrometric method that can be used is a GC-MS with electron impact (EI) ionization and a full scan mode. The mass isotopomers of the metabolite molecule fragment simultaneously in the ionization chamber because of high energy, and a set of fragment ions are observed in the spectrum. When GC-tandem mass spectrometry method (GC-MS/MS) is used, the isotopomer ion of interest can be chosen and fragmented (daughter ion scanning) to get an additional information. Many of the metabolites analyzed are polar, so derivatization may be needed to convert the metabolites to be volatile enough for GC-MS analysis. In isotopomer distribution calculations, the atoms from dramatizing reagent are also taken into account. With an LC-MS method, when an electrospray ionization (ESI) is used for analyzing polar metabolites, usually no derivatization may be needed.

The extent to which an isotopomer distribution is identifiable from tandem mass spectrometric data can depend on two aspects: first, the frequencies of mass isotopomers may need to be sufficient for the corresponding peaks to be reliably detected. Second, the fragmentation of the molecule may need to be sufficient. In order to completely pinpoint the abundance of each isotopomer, for every pair of carbons there may need to be a fragment where exactly one of the carbons appears.

Treatment with PARP Inhibitors or Metabolites Thereof

The compounds suitable for use in the present invention are compounds that inhibit fatty acid synthesis. Preferably the inhibitors (and metabolites thereof) are PARP inhibitors. The inhibition of fatty acid synthesis by the compounds as provided herein, can involve inhibition of one or more enzymes of a glucose pathway or a fatty acid biosynthetic pathway. A preferred PARP inhibitor of the present invention is a compound of formula I, its pharmaceutically acceptable salts or prodrugs thereof:

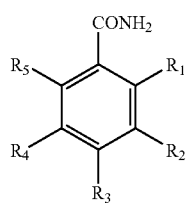

Formula I wherein, $R_1$, $R_2$, $R_3$, $R_4$, and $R_5$ are independently selected from a group consisting of hydrogen, hydroxy, optionally substituted amine, carboxyl, ester, nitroso, nitro, halogen, optionally substituted (C$_1$-C$_6$) alkyl, optionally substituted (C$_1$-C$_6$) alkoxy, optionally substituted (C$_3$-C$_7$) cycloalkyl, optionally substituted (C$_3$-C$_7$) heterocyclic, optionally substituted aryl and a sulfur-containing moiety. In some embodiments, the sulfur containing moiety is —SR$_6$, wherein R$_6$ is selected from the group consisting of hydrogen, C$_1$-C$_6$ acyl, optionally substituted (C$_1$-C$_6$) alkyl, optionally substituted (C$_3$-C$_7$) cycloalkyl, optionally substituted (C$_3$-C$_7$) heterocyclic and optionally substituted aryl.

Another preferred PARP inhibitor is compound of formula II, its pharmaceutically acceptable salts or prodrugs thereof:

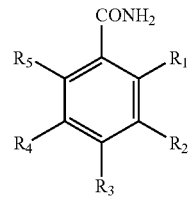

Formula II wherein, $R_1$, $R_3$, $R_4$, and $R_5$ are independently selected from a group consisting of hydrogen, hydroxy, optionally substituted amine, carboxyl, ester, nitroso, nitro, halogen, optionally substituted (C$_1$-C$_6$) alkyl, optionally substituted (C$_1$-C$_6$) alkoxy, optionally substituted (C$_3$-C$_7$) cycloalkyl, optionally substituted (C$_3$-C$_7$) heterocyclic, optionally substituted aryl and —SR$_6$; R$_2$ is either nitro or nitroso; and wherein at least two of the $R_1$, $R_3$, $R_4$, and $R_5$ substituents are always hydrogen; wherein R$_6$ is —SR$_6$, wherein R$_6$ is selected from the group consisting of hydrogen, C$_1$-C$_6$ acyl, optionally substituted (C$_1$-C$_6$) alkyl, optionally substituted (C$_3$-C$_7$) cycloalkyl, optionally substituted (C$_3$-C$_7$) heterocyclic and optionally substituted aryl and the optional substituents. In some embodiments R$_6$ is an optionally substituted (C$_1$-C$_6$) alkyl, which is a residue of an S-linked cysteine moiety, which may be a single cysteine amino acid or may form part of a dipeptide, tripeptide, tetrapeptide, pentapeptide or higher-order peptide containing cysteine as an amino acid.

A preferred PARP inhibitor is 3-nitro-4-iodobenzamide of formula III, its pharmaceutically acceptable salts or prodrugs thereof:

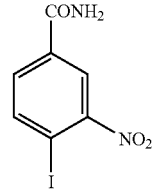

Formula III

Some embodiments of the present invention relate to a method of treating a metabolic disease by administering to a patient in need thereof an effective amount of a compound of formula II, its pharmaceutically acceptable salts or prodrugs thereof,

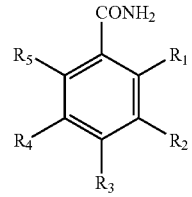

Formula II wherein, $R_1$, $R_3$, $R_4$, and $R_5$ are independently selected from the group consisting of hydrogen, hydroxy, optionally substituted amine, carboxyl, ester, nitroso, nitro, halogen, optionally substituted ($C_1$-$C_6$) alkyl, optionally substituted ($C_1$-$C_6$) alkoxy, optionally substituted ($C_3$-$C_7$) cycloalkyl, optionally substituted ($C_3$-$C_7$) heterocyclic, optionally substituted aryl and —$SR_6$; $R_2$ is either nitro or nitroso; and wherein at least two of the $R_1$, $R_3$, $R_4$, and $R_5$ substituents are always hydrogen; wherein $R_6$ is —$SR_6$, wherein $R_6$ is selected from the group consisting of hydrogen, $C_1$-$C_6$ acyl, optionally substituted ($C_1$-$C_6$) alkyl, optionally substituted ($C_3$-$C_7$) cycloalkyl, optionally substituted ($C_3$-$C_7$) heterocyclic and optionally substituted aryl and the optional substituents; and wherein the compound of formula II, its pharmaceutically acceptable salts or prodrugs thereof inhibits fatty acid synthesis, thereby treating the metabolic disease in the subject. In some embodiments $R_6$ is an optionally substituted ($C_1$-$C_6$) alkyl, which is a residue of an S-linked cysteine moiety, which may be a single cysteine amino acid or may form part of a dipeptide, tripeptide, tetrapeptide, pentapeptide or higher-order peptide containing cysteine as an amino acid.

The present invention further contemplates the use of metabolites of the compounds of formula I. Some metabolites useful in the present invention are of the Formula (IIa):

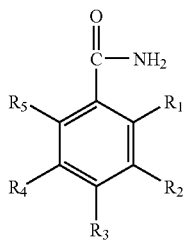

(IIa)

wherein either: (1) at least one of $R_1$, $R_2$, $R_3$, $R_4$, and $R_5$ substituent is always a sulfur-containing substituent, and the remaining substituents $R_1$, $R_2$, $R_3$, $R_4$, and $R_5$ are independently selected from the group consisting of hydrogen, hydroxy, amino, nitro, iodo, bromo, fluoro, chloro, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen; or (2) at least one of $R_1$, $R_2$, $R_3$, $R_4$, and $R_5$ substituents is not a sulfur-containing substituent and at least one of the five substituents $R_1$, $R_2$, $R_3$, $R_4$, and $R_5$ is always iodo, and wherein said iodo is always adjacent to a $R_1$, $R_2$, $R_3$, $R_4$, or $R_5$ group that is either a nitro, a nitroso, a hydroxyamino, hydroxy or an amino group; and pharmaceutically acceptable salts, solvates, isomers, tautomers, metabolites, analogs, or pro-drugs thereof. In some embodiments, the compounds of (2) are such that the iodo group is always adjacent a $R_1$, $R_2$, $R_3$, $R_4$ or $R_5$ group that is a nitroso, hydroxyamino, hydroxy or amino group. In some embodiments, the compounds of (2) are such that the iodo the iodo group is always adjacent a $R_1$, $R_2$, $R_3$, $R_4$ or $R_5$ group that is a nitroso, hydroxyamino, or amino group.

The following compositions are preferred metabolite compounds, each represented by a chemical formula:

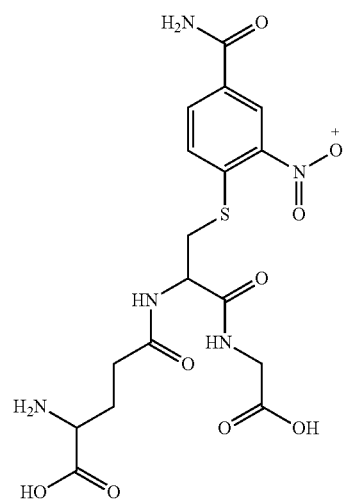

MS472

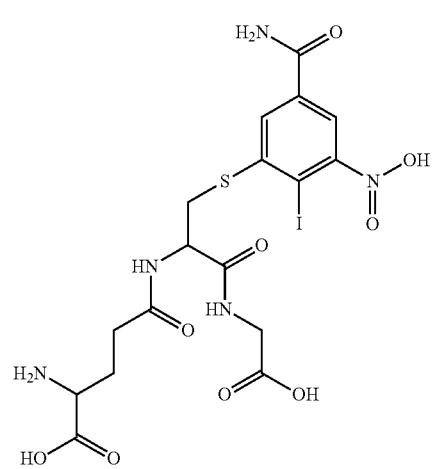

MS601

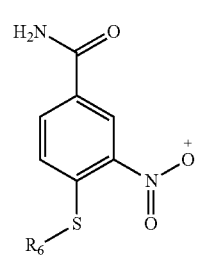

MS213

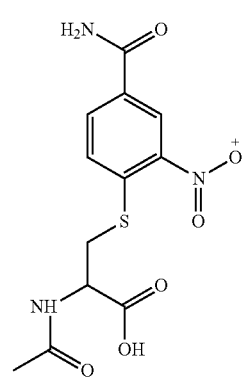

MS328

$R_6$ is selected from a group consisting of hydrogen, alkyl ($C_1$-$C_8$), alkoxy ($C_1$-$C_8$), isoquinolinones, indoles, thiazole, oxazole, oxadiazole, thiphene, or phenyl.

MS456
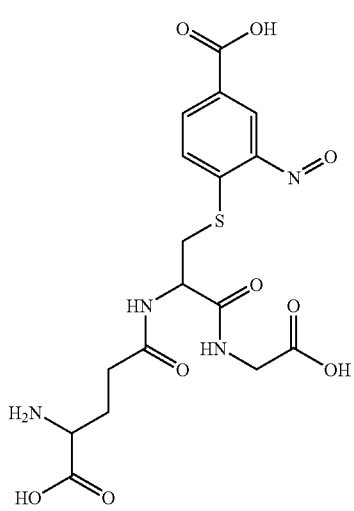
MS276
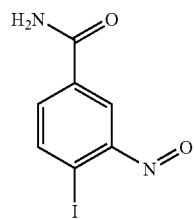
MS278
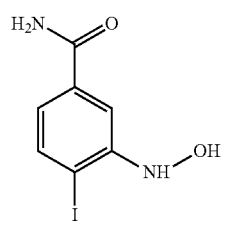
MS183
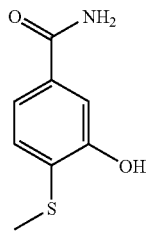
MS635a
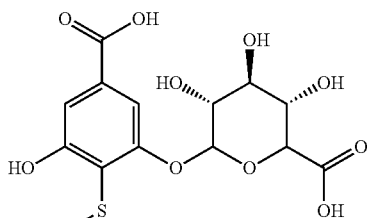
MS261
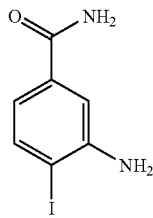
MS182
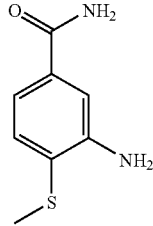
MS635b
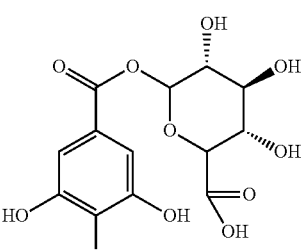
MS263
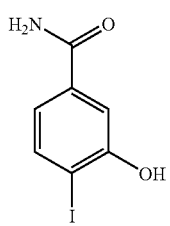
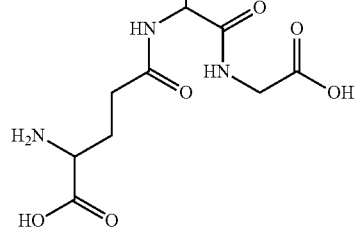

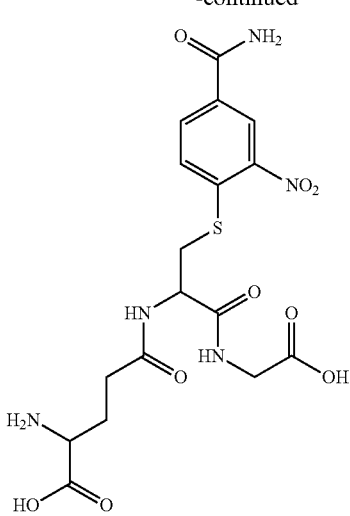

MS471

MS414

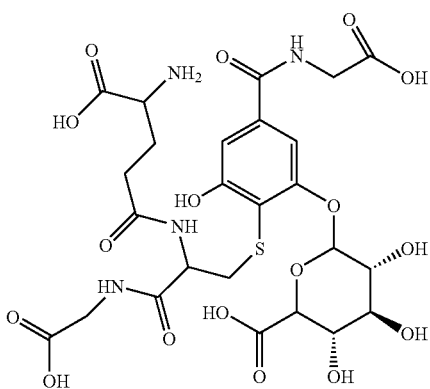

MS692

In some embodiments, the metabolites of the compounds as provided herein may be used in the methods of the present invention. For example, the metabolites include as described in U.S. application entitled, "Treatment of Cancer"; inventors Ernest Kun, Jerome Mendeleyev, Carol Basbaum, Hassan Lemjabbar-Alaoui, and Valeria Ossovskaya; filed on Sep. 5, 2006; Ser. No. 60/842,474, incorporated herein by reference in its entirety.

Some embodiments of the present invention relate to a method of treating cancer in a subject by determining a level of fatty acid in a sample from a subject, and administering an effective amount of a compound of formula II, its pharmaceutically acceptable salts or prodrugs thereof, to the subject wherein the administration is based on the determination of the level of fatty acid. The compound of formula II, its pharmaceutically acceptable salts or prodrugs thereof inhibit fatty acid synthesis, thereby treating cancer in the subject.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the compound(s) contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

The PARP inhibitors described herein can contain one or more asymmetric centers and thus occur as racemates and racemic mixtures, single enantiomers, individual diastereomers and diastereomeric mixtures. All such isomeric forms of these compounds are expressly included in the present invention. The PARP inhibitors described herein can also be represented in multiple tautomeric forms, all of which are included herein. The PARP inhibitors can also occur in cis- or trans- or E- or Z-double bond isomeric forms. All such isomeric forms of such inhibitors are expressly included in the present invention. All crystal forms of the PARP inhibitors described herein are expressly included in the present invention. The PARP inhibitors can also be present as their pharmaceutically acceptable salts, derivatives or prodrugs.

There are other PARP inhibitors known in the art and they are within the scope of the present invention. The PARP inhibitors have been designed as analogs of benzamides, which bind competitively with the natural substrate NAD in the catalytic site of PARP. The PARP inhibitors include, but are not limited to, benzamides, quinolones and isoquinolones, benzopyrones, methyl 3,5-diiodo-4-(4'-methoxyphenoxy)benzoate, and 3,5-diiodo-4-(4'-methoxyphenoxy)acetophenone (U.S. Pat. No. 5,464,871, U.S. Pat. No. 5,670,518, U.S. Pat. No. 6,004,978, U.S. Pat. No. 6,169,104, U.S. Pat. No. 5,922,775, U.S. Pat. No. 6,017,958, U.S. Pat. No. 5,736,576, and U.S. Pat. No. 5,484,951, all incorporated herein in their entirety). The PARP inhibitors include a variety of cyclic benzamide analogs (i.e. lactams) which are potent inhibitors at the NAD site. Other PARP inhibitors include, but are not limited to, benzimidazoles and indoles (EP 841924, EP 1127052, U.S. Pat. No. 6,100,283, U.S. Pat. No. 6,310,082, US 2002/156050, US 2005/054631, WO 05/012305, WO 99/11628, and US 2002/028815). Other PARP inhibitors known in the art can also inhibit the synthesis of the fatty acid and are within the scope of the present invention (U.S. Application No. 60/804,563, filed on Jun. 12, 2006, incorporated herein by reference in its entirety).

Cancer Types

The cancer in the present invention includes but is not limited to, colon adenocarcinoma, esophagus adenocarcinoma, liver hepatocellular carcinoma, squamous cell carcinoma, pancreas adenocarcinoma, islet cell tumor, rectum adenocarcinoma, gastrointestinal stromal tumor, stomach adenocarcinoma, adrenal cortical carcinoma, follicular carcinoma, papillary carcinoma, breast cancer, ductal carcinoma, lobular carcinoma, intraductal carcinoma, mucinous carcinoma, phyllodes tumor, ovarian adenocarcinoma, endometrium adenocarcinoma, granulose cell tumor, mucinous cystadenocarcinoma, cervix adenocarcinoma, vulva squamous cell carcinoma, basal cell carcinoma, prostate adenocarcinoma, giant cell tumor of bone, bone osteosarcoma, larynx carcinoma, lung adenocarcinoma, kidney carcinoma, urinary bladder carcinoma, Wilm's tumor, and lymphoma.

The other examples of the cancer include but are not limited to, adrenal cortical cancer, anal cancer, aplastic anemia, bile duct cancer, bladder cancer, bone cancer, bone metastasis, Adult CNS brain tumors, Children CNS brain tumors, breast cancer, Castleman Disease, cervical cancer, Childhood Non-Hodgkin's lymphoma, colon and rectum cancer, endometrial cancer, esophagus cancer, Ewing's family of tumors, eye cancer, gallbladder cancer, gastrointestinal carcinoid tumors, gastrointestinal stromal tumors, gestational trophoblastic disease, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, thyroid cancer, uterine sarcoma, vaginal cancer, vulvar cancer, and Waldenstr.o:m's macroglobulinemia.

The methods provided by the invention can comprise the administration of the PARP inhibitors in combination with other therapies. The choice of therapy that can be co-administered with the compositions of the invention can depend, in part, on the condition being treated. For example, for treating acute myeloid leukemia, a PARP inhibitor can be used in combination with radiation therapy, monoclonal antibody therapy, chemotherapy, bone marrow transplantation, gene therapy, immunotherapy, or a combination thereof.

Her-2 Related Cancer

In one aspect, the invention provides a method of treating Her-2 related cancer by administering an effective amount of PARP inhibitor. Her-2 disease is a type of breast cancer. Characterized by aggressive growth and a poor prognosis, it can be caused by the presence of excessive numbers of a gene called HER2 (human epidermal growth factor receptor-2) in tumor cells. Therapies that can used in combination with the PARP inhibitors as disclosed herein include, but are no limited to Her-2 antibodies such as herceptin, anti-hormones (e.g., selective estrogen receptor modulator (SERM) tamoxifen), chemotherapy and radiotherapy, aromatase inhibitors (e.g. anastrozole, letrozole and exemestane) and anti-estrogens (e.g., fulvestrant (Faslodex)).

Breast Cancer

In one aspect, the invention provides a method of treating breast cancer including but not limited to, a ductal carcinoma in duct tissue in a mammary gland.

A lobular carcinoma in situ and a ductal carcinoma in situ are breast cancers that develop in the lobules and ducts, respectively, but may not have spread to the fatty tissue surrounding the breast or to other areas of the body. An infiltrating (or invasive) lobular and a ductal carcinoma are cancers that have developed in the lobules and ducts, respectively, and have spread to either the breast's fatty tissue and/or other parts of the body. Other cancers of the breast that can benefit from treatment provided by the methods of the present invention are medullary carcinomas, colloid carcinomas, tubular carcinomas, and inflammatory breast cancer.

In some embodiments, the invention provides for treatment of so-called "triple negative" breast cancer. There are several subclasses of breast cancer identified by classic biomarkers such as estrogen receptor (ER) and/or progesterone receptor (PR) positive tumors, HER2-amplified tumors, and ER/PR/HER2-negative tumors. These three subtypes have been reproducibly identified by gene expression profiling in multiple breast cancer and exhibit basal-like subtype expression profiles and poor prognosis. Triple negative breast cancer is characterized by ER/PR/HER2-negative tumors.

Ovarian Cancer

In another aspect, the invention provides a method of treating ovarian cancer including but not limited to, epithelial ovarian tumors, adenocarcinoma in the ovary and an adenocarcinoma that has migrated from the ovary into the abdominal cavity. Treatments for ovarian cancer that can be used in combination with the PARP inhibitors of the present invention include but are not limited to, surgery, immunotherapy, chemotherapy, hormone therapy, radiation therapy, or a combination thereof. Some possible surgical procedures include debulking, and a unilateral or bilateral oophorectomy and/or a unilateral or bilateral salpigectomy.

Anti-cancer drugs that can be used in the combination therapy include cyclophosphamide, etoposide, altretamine, and ifosfamide. Hormone therapy with the drug tamoxifen can be used to shrink ovarian tumors. Radiation therapy can be external beam radiation therapy and/or brachytherapy.

Cervical Cancer

In another aspect, the invention provides a method of treating cervical cancer including but not limited to, an adenocarcinoma in the cervix epithelial. Two main types of this cancer exist: squamous cell carcinoma and adenocarcinomas. Some cervical cancers have characteristics of both of these and are called adenosquamous carcinomas or mixed carcinomas.

Prostate Cancer

In one other aspect, the invention provides methods to treat prostate cancer including but not limited to, an adenocarcinoma or an adenocarcinoma that has migrated to the bone. Prostate cancer develops in the prostate organ in men, which surrounds the first part of the urethra.

Pancreatic Cancer

In another aspect, the invention provides methods of treating pancreatic cancer including but not limited to, an epitheloid carcinoma in the pancreatic duct tissue and an adenocarcinoma in a pancreatic duct.

Treatments that can be used in combination with the PARP inhibitors of the present invention include but are not limited to, surgery, immunotherapy, radiation therapy, and chemotherapy. Possible surgical treatment options include a distal or total pancreatectomy and a pancreaticoduodenectomy (Whipple procedure). Radiation therapy can be an option for pancreatic cancer patients, such as external beam radiation where radiation is focused on the tumor by a machine outside the body. Another option is intraoperative electron beam radiation administered during an operation.

Bladder Cancer

In another aspect, the invention provides methods of treating bladder cancer including but not limited to, a transitional cell carcinoma in urinary bladder. Bladder cancers are urothelial carcinomas (transitional cell carcinomas) or tumors in the urothelial cells that line the bladder. The remaining cases of bladder cancer are squamous cell carcinomas, adenocarcinomas, and small cell cancers. Several subtypes of urothelial carcinomas exist depending on whether they are noninvasive or invasive and whether they are papillary, or flat. Noninvasive tumors are in the urothelium, the innermost layer of the bladder, while invasive tumors have spread from the urothelium to deeper layers of the bladder's main muscle wall. Invasive papillary urothelial carcinomas are slender finger-like projections that branch into the hollow center of the bladder and also grow outward into the bladder wall. Non-invasive papillary urothelial tumors grow towards the center of the bladder. While a non-invasive, flat urothelial tumor (also called a flat carcinoma in situ) is confined to the layer of cells closest to the inside hollow part of the bladder, an invasive flat urothelial carcinoma invades the deeper layer of the bladder, particularly the muscle layer.

The therapies that can be used in combination with the PARP inhibitors of the present invention for the treatment of bladder cancer include surgery, radiation therapy, immunotherapy, chemotherapy, or a combination thereof. Some surgical options are a transurethral resection, a cystectomy, or a radical cystectomy. Radiation therapy for bladder cancer can include external beam radiation and brachytherapy.

Immunotherapy is another method that can be used to treat a bladder cancer patient. One method is Bacillus Calmette-Guerin (BCG) where a bacterium sometimes used in tuberculosis vaccination is given directly to the bladder through a catheter. The body mounts an immune response to the bacterium, thereby attacking and killing the cancer cells. Another method of immunotherapy is the administration of interferons, glycoproteins that modulate the immune response. Interferon alpha is often used to treat bladder cancer.

Anti-cancer drugs that can be used in combination to treat bladder cancer include thitepa, methotrexate, vinblastine, doxorubicin, cyclophosphamide, paclitaxel, carboplatin, cisplatin, ifosfamide, gemcitabine, or combinations thereof.

Acute Myeloid Leukemia

In another aspect, the invention provides methods of treating acute myeloid leukemia (AML), preferably acute promyelocytic leukemia in peripheral blood. AML begins in the bone marrow but can spread to other parts of the body including the lymph nodes, liver, spleen, central nervous system, and testes. AML is characterized by immature bone marrow cells usually granulocytes or monocytes, which can continue to reproduce and accumulate.

AML can be treated by other therapies in combination with the PARP inhibitors of the present invention. Such therapies include but are not limited to, immunotherapy, radiation therapy, chemotherapy, bone marrow or peripheral blood stem cell transplantation, or a combination thereof. Radiation therapy includes external beam radiation and can have side effects. Anti-cancer drugs that can be used in chemotherapy to treat AML include cytarabine, anthracycline, anthracenedione, idarubicin, daunorubicin, idarubicin, mitoxantrone, thioguanine, vincristine, prednisone, etoposide, or a combination thereof.

Monoclonal antibody therapy can be used to treat AML patients. Small molecules or radioactive chemicals can be attached to these antibodies before administration to a patient in order to provide a means of killing leukemia cells in the body. The monoclonal antibody, gemtuzumab ozogamicin, which binds CD33 on AML cells, can be used to treat AML patients unable to tolerate prior chemotherapy regimens. Bone marrow or peripheral blood stem cell transplantation can be used to treat AML patients. Some possible transplantation procedures are an allogenic or an autologous transplant.

Other types of leukemia's that can be treated by the methods provided by the invention include but not limited to, Acute Lymphocytic Leukemia, Acute Myeloid Leukemia, Chronic Lymphocytic Leukemia, Chronic Myeloid Leukemia, Hairy Cell Leukemia, Myelodysplasia, and Myeloproliferative Disorders.

Lung Cancer

In another aspect, the invention provides methods to treat lung cancer. The common type of lung cancer is non-small cell lung cancer (NSCLC), which is divided into squamous cell carcinomas, adenocarcinomas, and large cell undifferentiated carcinomas. Treatment options for lung cancer in combination with the PARP inhibitors of the present invention include surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy can be external beam radiation therapy or brachytherapy.

Some anti-cancer drugs that can be used in chemotherapy to treat lung cancer include cisplatin, carboplatin, paclitaxel, docetaxel, gemcitabine, vinorelbine, irinotecan, etoposide, vinblastine, erlotinib, gefitinib, ifosfamide, methotrexate, or a combination thereof. Photodynamic therapy (PDT) can be used to treat lung cancer patients.

Skin Cancer

In another aspect, the invention provides methods to treat skin cancer. There are several types of cancer that start in the skin. The most common types are basal cell carcinoma and squamous cell carcinoma, which are non-melanoma skin cancers. Actinic keratosis is a skin condition that sometimes develops into squamous cell carcinoma. Non-melanoma skin cancers rarely spread to other parts of the body. Melanoma, the rarest form of skin cancer, is more likely to invade nearby tissues and spread to other parts of the body.

Different types of treatments that can be used in combination with the PARP inhibitors of the present invention include but are not limited to, surgery, radiation therapy, chemotherapy and photodynamic therapy. Some possible surgical options for treatment of skin cancer are Mohs micrographic surgery, simple excision, electrodesiccation and curettage, cryosurgery, laser surgery. Radiation therapy can be external beam radiation therapy or brachytherapy. Other types of treatments include biologic therapy or immunotherapy, chemoimmunotherapy, topical chemotherapy with fluorouracil and photodynamic therapy.

Eye Cancer, Retinoblastoma

In another aspect, the invention provides methods to treat eye retinoblastoma. Retinoblastoma is a malignant tumor of the retina. The tumor can be in one eye only or in both eyes. Treatment options that can be used in combination with the PARP inhibitors of the present invention include enucleation (surgery to remove the eye), radiation therapy, cryotherapy, photocoagulation, immunotherapy, thermotherapy and chemotherapy. Radiation therapy can be external beam radiation therapy or brachytherapy.

Eye Cancer, Intraocular Melanoma

In another aspect, the invention provides methods to treat intraocular (eye) melanoma. Intraocular melanoma is a disease in which cancer cells are found in the part of the eye called the uvea. The uvea includes the iris, the ciliary body, and the choroid. Intraocular melanoma occurs most often in people who are middle aged. Treatments that can be used in combination with the PARP inhibitors of the present invention include surgery, immunotherapy, radiation therapy and laser therapy. Surgery is the most common treatment of intraocular melanoma. Some possible surgical options are iridectomy, iridotrabeculectomy, iridocyclectomy, choroidectomy, enucleation and orbital exenteration. Radiation therapy can be external beam radiation therapy or brachytherapy. Laser therapy can be an intensely powerful beam of light to destroy the tumor, thermotherapy or photocoagulation.

Endometrium Cancer

In another aspect, the invention provides methods to treat endometrium cancer. Endometrial cancer is a cancer that starts in the endometrium, the inner lining of the uterus. Some of the examples of the cancer of uterus and endometrium include, but are not limited to, adenocarcinomas, adenoacanthomas, adenosquamous carcinomas, papillary serous adenocarcinomas, clear cell adenocarcinomas, uterine sarcomas, stromal sarcomas, malignant mixed mesodermal tumors, and leiomyosarcomas.

Liver Cancer

In another aspect, the invention provides methods to treat primary liver cancer (cancer that begins in the liver). Primary liver cancer can occur in both adults and children. Different types of treatments that can be used in combination with the PARP inhibitors of the present invention include surgery, immunotherapy, radiation therapy, chemotherapy and percutaneous ethanol injection. The types of surgery that can be used are cryosurgery, partial hepatectomy, total hepatectomy and radiofrequency ablation. Radiation therapy can be external beam radiation therapy, brachytherapy, radiosensitizers or radiolabel antibodies. Other types of treatment include hyperthermia therapy and immunotherapy.

Kidney Cancer

In another aspect, the invention provides methods to treat kidney cancer. Kidney cancer (also called renal cell cancer or renal adenocarcinoma) is a disease in which malignant cells are found in the lining of tubules in the kidney. Treatments that can be used in combination with the PARP inhibitors of the present invention include surgery, radiation therapy, chemotherapy and immunotherapy. Some possible surgical options to treat kidney cancer are partial nephrectomy, simple nephrectomy and radical nephrectomy. Radiation therapy can be external beam radiation therapy or brachytherapy. Stem cell transplant can be used to treat kidney cancer.

Thyroid Cancer

In another aspect, the invention provides methods to treat thyroid cancer. Thyroid cancer is a disease in which cancer (malignant) cells are found in the tissues of the thyroid gland. The four main types of thyroid cancer are papillary, follicular, medullary and anaplastic. Thyroid cancer can be treated by surgery, immunotherapy, radiation therapy, hormone therapy and chemotherapy. Some possible surgical options that can be used in combination with the PARP inhibitors of the present invention include but are not limited to, lobectomy, near-total thyroidectomy, total thyroidectomy and lymph node dissection. Radiation therapy can be external radiation therapy or can require intake of a liquid that contains radioactive iodine. Hormone therapy uses hormones to stop cancer cells from growing. In treating thyroid cancer, hormones can be used to stop the body from making other hormones that might make cancer cells grow.

AIDS Related Cancers
AIDS-Related Lymphoma

In another aspect, the invention provides methods to treat AIDS-related lymphoma. AIDS-related lymphoma is a disease in which malignant cells form in the lymph system of patients who have acquired immunodeficiency syndrome (AIDS). AIDS is caused by the human immunodeficiency virus (HIV), which attacks and weakens the body's immune system. The immune system is then unable to fight infection and diseases that invade the body. People with HIV disease have an increased risk of developing infections, lymphoma, and other types of cancer. Lymphomas are cancers that affect the white blood cells of the lymph system. Lymphomas are divided into two general types: Hodgkin's lymphoma and non-Hodgkin's lymphoma. Both Hodgkin's lymphoma and non-Hodgkin's lymphoma can occur in AIDS patients, but non-Hodgkin's lymphoma is more common. When a person with AIDS has non-Hodgkin's lymphoma, it is called an AIDS-related lymphoma. Non-Hodgkin's lymphomas can be indolent (slow-growing) or aggressive (fast-growing). AIDS-related lymphoma is usually aggressive. The three main types of AIDS-related lymphoma are diffuse large B-cell lymphoma, B-cell immunoblastic lymphoma and small non-cleaved cell lymphoma.

Highly-active antiretroviral therapy (HAART) is used to slow progression of HIV. Medicine to prevent and treat infections, which can be serious, is also used. AIDS-related lymphomas can be treated by chemotherapy, immunotherapy, radiation therapy and high-dose chemotherapy with stem cell transplant. Radiation therapy can be external beam radiation therapy or brachytherapy. AIDS-related lymphomas can be treated by monoclonal antibody therapy.

Kaposi's Sarcoma

In one aspect, the invention provides methods to treat Kaposi's sarcoma. Kaposi's sarcoma is a disease in which cancer cells are found in the tissues under the skin or mucous membranes that line the mouth, nose, and anus. Kaposi's sarcoma can occur in people who are taking immunosuppressants. Kaposi's sarcoma in patients who have Acquired Immunodeficiency Syndrome (AIDS) is called epidemic Kaposi's sarcoma. Kaposi's sarcoma can be treated with surgery, chemotherapy, radiation therapy and immunotherapy. External radiation therapy is a common treatment of Kaposi's sarcoma. Treatments that can be used in combination with the PARP inhibitors of the present invention include but are not limited to, local excision, electrodesiccation and curettage, and cryotherapy.

Viral-Induced Cancers

In another aspect, the invention provides methods to treat viral-induced cancers. The major virus-malignancy systems include hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer.

Virus-Induced Hepatocellular Carcinoma

HBV and HCV and hepatocellular carcinoma or liver cancer can appear to act via chronic replication in the liver by causing cell death and subsequent regeneration. Treatments that can be used in combination with the PARP inhibitors of the present invention include but are not limited to, include surgery, immunotherapy, radiation therapy, chemotherapy and percutaneous ethanol injection. The types of surgery that can be used are cryosurgery, partial hepatectomy, total hepatectomy and radiofrequency ablation. Radiation therapy can be external beam radiation therapy, brachytherapy, radiosensitizers or radiolabel antibodies. Other types of treatment include hyperthermia therapy and immunotherapy.

Viral-Induced Adult T Cell Leukemia/Lymphoma

Adult T cell leukemia is a cancer of the blood and bone marrow. The treatments for adult T cell leukemia/lymphoma that can be used in combination with the PARP inhibitors of the present invention include but are not limited to, radiation therapy, immunotherapy, and chemotherapy. Radiation therapy can be external beam radiation therapy or brachytherapy. Other methods of treating adult T cell leukemia/lymphoma include immunotherapy and high-dose chemotherapy with stem cell transplantation.

Viral-Induced Cervical Cancer

Infection of the cervix with human papillomavirus (HPV) is a cause of cervical cancer. The treatments for cervical cancers that can be used in combination with the PARP inhibitors of the present invention include but are not limited to, surgery, immunotherapy, radiation therapy and chemotherapy. The types of surgery that can be used are conization, total hysterectomy, bilateral salpingo-oophorectomy, radical hysterectomy, pelvic exenteration, cryosurgery, laser surgery and loop electrosurgical excision procedure. Radiation therapy can be external beam radiation therapy or brachytherapy.

CNS Cancers

Brain and spinal cord tumors are abnormal growths of tissue found inside the skull or the bony spinal column, which are the primary components of the central nervous system (CNS). Benign tumors are noncancerous, and malignant tumors are cancerous. Tumors that originate in the brain or spinal cord are called primary tumors. Primary tumors can result from specific genetic disease (e.g., neurofibromatosis, tuberous sclerosis) or from exposure to radiation or cancer-causing chemicals.

The primary brain tumor in adults comes from cells in the brain called astrocytes that make up the blood-brain barrier and contribute to the nutrition of the central nervous system. These tumors are called gliomas (astrocytoma, anaplastic astrocytoma, or glioblastoma multiforme). Some of the tumors are, but not limited to, Oligodendroglioma, Ependymoma, Meningioma, Lymphoma, Schwannoma, and Medulloblastoma.

Neuroepithelial Tumors of the CNS

Astrocytic tumors, such as astrocytoma; anaplastic (malignant) astrocytoma, such as hemispheric, diencephalic, optic, brain stem, cerebellar; glioblastoma multiforme; pilocytic astrocytoma, such as hemispheric, diencephalic, optic, brain stem, cerebellar; subependymal giant cell astrocytoma; and pleomorphic xanthoastrocytoma. Oligodendroglial tumors, such as oligodendroglioma; and anaplastic (malignant) oligodendroglioma. Ependymal cell tumors, such as ependymoma; anaplastic ependymoma; myxopapillary ependymoma; and subependymoma. Mixed gliomas, such as mixed oligoastrocytoma; anaplastic (malignant) oligoastrocytoma; and others (e.g. ependymo-astrocytomas). Neuroepithelial tumors of uncertain origin, such as polar spongioblastoma; astroblastoma; and gliomatosis cerebri. Tumors of the choroid plexus, such as choroid plexus papilloma; and choroid plexus carcinoma (anaplastic choroid plexus papilloma). Neuronal and mixed neuronal-glial tumors, such as gangliocytoma; dysplastic gangliocytoma of cerebellum (Lhemmitte-Duclos); ganglioglioma; anaplastic (malignant) ganglioglioma; desmoplastic infantile ganglioglioma, such as desmoplastic infantile astrocytoma; central neurocytoma; dysembryoplastic neuroepithelial tumor; olfactory neuroblastoma (esthesioneuroblastoma. Pineal Parenchyma Tumors, such as pineocytoma; pineoblastoma; and mixed pineocytoma/pineoblastoma. Tumors with neuroblastic or glioblastic elements (embryonal tumors), such as medulloepithelioma; primitive neuroectodermal tumors with multipotent differentiation, such as medulloblastoma; cerebral primitive neuroectodermal tumor; neuroblastoma; retinoblastoma; and ependymoblastoma.

Other CNS Neoplasms

Tumors of the sellar region, such as pituitary adenoma; pituitary carcinoma; and craniopharyngioma. Hematopoietic tumors, such as primary malignant lymphomas; plasmacytoma; and granulocytic sarcoma. Germ Cell Tumors, such as germinoma; embryonal carcinoma; yolk sac tumor (endodermal sinus tumor); choriocarcinoma; teratoma; and mixed germ cell tumors. Tumors of the Meninges, such as meningioma; atypical meningioma; and anaplastic (malignant) meningioma. Non-menigothelial tumors of the meninges, such as Benign Mesenchymal; Malignant Mesenchymal; Primary Melanocytic Lesions; Hemopoietic Neoplasms; and Tumors of Uncertain Histogenesis, such as hemangioblastoma (capillary hemangioblastoma). Tumors of Cranial and Spinal Nerves, such as schwannoma (neurinoma, neurilemoma); neurofibroma; malignant peripheral nerve sheath tumor (malignant schwannoma), such as epithelioid, divergent mesenchymal or epithelial differentiation, and melanotic. Local Extensions from Regional Tumors; such as paraganglioma (chemodectoma); chordoma; chodroma; chondrosarcoma; and carcinoma. Metastatic tumours, Unclassified Tumors and Cysts and Tumor-like Lesions, such as Rathke cleft cyst; Epidermoid; dermoid; colloid cyst of the third ventricle; enterogenous cyst; neuroglial cyst; granular cell tumor (choristoma, pituicytoma); hypothalamic neuronal hamartoma; nasal glial herterotopia; and plasma cell granuloma.

Chemotherapeutics available are, but not limited to, alkylating agents such as, Cyclophosphamide, Ifosphamide, Melphalan, Chlorambucil, BCNU, CCNU, Decarbazine, Procarbazine, Busulfan, and Thiotepa; antimetabolites such as, Methotraxate, 5-Fluorouracil, Cytarabine, Gemcitabine (Gemzar®), 6-mercaptopurine, 6-thioguanine, Fludarabine, and Cladribine; anthracyclins such as, daunorubicin. Doxorubicin, Idarubicin, Epirubicin and Mitoxantrone; antibiotics such as, Bleomycin; camptothecins such as, irinotecan and topotecan; taxanes such as, paclitaxel and docetaxel; and platinums such as, Cisplatin, carboplatin, and Oxaliplatin.

PNS Cancers

The peripheral nervous system consists of the nerves that branch out from the brain and spinal cord. These nerves form the communication network between the CNS and the body parts. The peripheral nervous system is further subdivided into the somatic nervous system and the autonomic nervous system. The somatic nervous system consists of nerves that go to the skin and muscles and is involved in conscious activities. The autonomic nervous system consists of nerves that connect the CNS to the visceral organs such as the heart, stomach, and intestines. It mediates unconscious activities.

Acoustic neuromas are benign fibrous growths that arise from the balance nerve, also called the eighth cranial nerve or vestibulocochlear nerve. The malignant peripheral nerve sheath tumor (MPNST) is the malignant counterpart to benign soft tissue tumors such as neurofibromas and schwannomas. It is most common in the deep soft tissue, usually in close proximity of a nerve trunk. The most common sites include the sciatic nerve, brachial plexus, and sarcal plexus.

The MPNST can be classified into three major categories with epithelioid, mesenchymal or glandular characteristics. Some of the MPNST include but not limited to, subcutaneous malignant epithelioid schwannoma with cartilaginous differentiation, glandular malignant schwannoma, malignant peripheral nerve sheath tumor with perineurial differentiation, cutaneous epithelioid malignant nerve sheath tumor with rhabdoid features, superficial epithelioid MPNST, triton Tumor (MPNST with rhabdomyoblastic differentiation), schwannoma with rhabdomyoblastic differentiation. Rare MPNST cases contain multiple sarcomatous tissue types, especially osteosarcoma, chondrosarcoma and angiosarcoma. These have sometimes been indistinguishable from the malignant mesenchymoma of soft tissue.

Other types of PNS cancers include but not limited to, malignant fibrous cytoma, malignant fibrous histiocytoma, malignant meningioma, malignant mesothelioma, and malignant mixed Müllerian tumor.

Oral Cavity and Oropharyngeal Cancer

Cancers of the oral cavity include but are not limited to, hypopharyngeal cancer, laryngeal cancer, nasopharyngeal cancer, and oropharyngeal cancer.

Stomach Cancer

There are three main types of stomach cancers: lymphomas, gastric stromal tumors, and carcinoid tumors. Lymphomas are cancers of the immune system tissue that are sometimes found in the wall of the stomach. Gastric stromal tumors develop from the tissue of the stomach wall. Carcinoid tumors are tumors of hormone-producing cells of the stomach.

Testicular Cancer

Testicular cancer is cancer that typically develops in one or both testicles in young men. Cancers of the testicle develop in certain cells known as germ cells. The two types of germ cell tumors (GCTs) that occur in men are seminomas (60%) and nonseminomas (40%). Tumors can also arise in the supportive and hormone-producing tissues, or stroma, of the testicles. Such tumors are known as gonadal stromal tumors. The two types are Leydig cell tumors and Sertoli cell tumors. Secondary testicular tumors are those that start in another organ and then spread to the testicle. Lymphoma is a secondary testicular cancer.

Thymus Cancer

The thymus is a small organ located in the upper/front portion of your chest, extending from the base of the throat to the front of the heart. The thymus contains two main types of cells, thymic epithelial cells and lymphocytes. Thymic epithelial cells can give origin to thymomas and thymic carcinomas. Lymphocytes, whether in the thymus or in the lymph nodes, can become malignant and develop into cancers called Hodgkin disease and non-Hodgkin lymphomas. The thymus cancer includes Kulchitsky cells, or neuroendocrine cells, which normally release certain hormones. These cells can give rise to cancers, called carcinoids or carcinoid tumors.

Treatments that can be used in combination with the PARP inhibitors of the present invention include but are not limited to, surgery, immunotherapy, chemotherapy, radiation therapy, combination of chemotherapy and radiation therapy or biological therapy. Anticancer drugs that have been used in the treatment of thymomas and thymic carcinomas are doxorubicin (Adriamycin), cisplatin, ifosfamide, and corticosteroids (prednisone).

Nutritional and Metabolic Disorders

The examples of nutritional and metabolic disorders include, but are not limited to, diabetes insipidus, fabry, fatty acid metabolism disorders, galactosemia, gaucher, glucose-6-phosphate dehydrogenase (G6PD), glutaric aciduria, hurler, hurler-scheie, hunter, hypophosphatemia, 1-cell, krabbe, lactic acidosis, long chain 3 hydroxyacyl CoA dehydrogenase deficiency (LCHAD), lysosomal storage diseases, mannosidosis, maple syrup urine, maroteaux-lamy, metachromatic leukodystrophy, mitochondrial, morquio, mucopolysaccharidosis, neuro-metabolic, niemann-pick, organic acidemias, purine, phenylketonuria (PKU), pompe, pseudo-hurler, pyruvate dehydrogenase deficiency, sandhoff, sanfilippo, scheie, sly, tay-sachs, trimethylaminuria (fish-malodor syndrome), urea cycle conditions, vitamin D deficiency rickets, metabolic disease of muscle, inherited metabolic disorders, acid-base imbalance, acidosis, alkalosis, alkaptonuria, alpha-mannosidosis, amyloidosis, anemia, iron-deficiency, ascorbic acid deficiency, avitaminosis, beriberi, biotinidase deficiency, deficient glycoprotein syndrome, carnitine disorders, cystinosis, cystinuria, fabry disease, fatty acid oxidation disorders, fucosidosis, galactosemias, gaucher disease, gilbert disease, glucosephosphate dehydrogenase deficiency, glutaric academia, glycogen storage disease, hartnup disease, hemochromatosis, hemosiderosis, hepatolenticular degeneration, histidinemia, homocystinuria, hyperbilirubinemia, hypercalcemia, hyperinsulinism, hyperkalemia, hyperlipidemia, hyperoxaluria, hypervitaminosis A, hypocalcemia, hypoglycemia, hypokalemia, hyponatremia, hypophosphotasia, insulin resistance, iodine deficiency, iron overload, jaundice, chronic idiopathic, leigh disease, Lesch-Nyhan syndrome, leucine metabolism disorders, lysosomal storage diseases, magnesium deficiency, maple syrup urine disease, MELAS syndrome, menkes kinky hair syndrome, metabolic syndrome X, mucolipidosis, mucopolysacchabridosis, Niemann-Pick disease, obesity, ornithine carbamoyltransferase deficiency disease, osteomalacia, pellagra, peroxisomal disorders, porphyria, erythropoietic, porphyries, progeria, pseudo-gaucher disease, refsum disease, reye syndrome, rickets, sandhoff disease, tangier disease, Tay-sachs disease, tetrahydrobiopterin deficiency, trimethylaminuria (fish odor syndrome), tyrosinemias, urea cycle disorders, water-electrolyte imbalance, wernicke encephalopathy, vitamin A deficiency, vitamin B12 deficiency, vitamin B deficiency, wolman disease, and zellweger syndrome.

In some preferred embodiments, the metabolic diseases include diabetes and obesity.

Methods of Use

The compounds suitable for use in the present invention are compounds that inhibit fatty acid synthesis. Preferably the inhibitors are PARP inhibitors. The analysis of the level of fatty acid before and/or after treatment with an effective amount of PARP inhibitors has various therapeutic and diagnostic applications. Clinical applications include, for example, detection of disease, distinguishing disease states to inform prognosis, selection of therapy such as, treatment with an effective amount of PARP inhibitors, prediction of therapeutic response, disease staging, identification of disease processes, prediction of efficacy of therapy with PARP inhibitors, monitoring of patients trajectories (e.g., prior to onset of disease), prediction of adverse response to PARP inhibitors, monitoring of therapy associated efficacy and toxicity, and detection of recurrence. An identification of the level of the fatty acid in a subject can also be used to select a therapy and a personalized dose regimen for a subject for treatment with a PARP inhibitor.

The identification of the level of fatty acid in a subject and subsequent treatment with an effective amount of PARP inhibitors can be used to enable or assist in the pharmaceutical drug development process for therapeutic agents. The identification of the level of fatty acid can be used to select subjects enrolling in a clinical trial for PARP inhibitors. Further identification of the level of fatty acid can indicate the state of the disease of subjects undergoing treatment in clinical trials, and show changes in the state during the treatment with PARP inhibitors. The identification of the level of fatty acid can demonstrate the efficacy of treatment with PARP inhibitors, and can be used to stratify subjects according to their responses to various therapies. The identification of the level of the fatty acid can also be used to select a personalized dose regimen for the subject for treatment with PARP inhibitors.

In certain embodiments, patients, health care providers, such as doctors and nurses, or health care managers, select a treatment of a subject with an effective amount of PARP inhibitors based on the level of the fatty acid in a sample from the subject. The methods can be used to evaluate the efficacy of treatments over time. For example, biological samples can be obtained from a patient over a period of time as the patient is undergoing treatment with PARP inhibitors. The level of fatty acid in the different samples can be compared to each other to determine the efficacy of the treatment. Also, the methods described herein can be used to compare the efficacies of different disease therapies including treatment with PARP inhibitors, and/or responses to one or more treatments in different populations (e.g., ethnicities, family histories, etc.).

Formulation and Pharmaceutical Compositions

The methods provided by the invention can comprise the administration of an effective amount of inhibitors as provided herein, in combination with other therapies. The choice of therapy that can be co-administered with the compositions of the invention will depend, in part, on the condition being treated. For example, for treating acute myeloid leukemia, compound of some embodiments of the invention can be used in combination with radiation therapy, monoclonal antibody therapy, chemotherapy, bone marrow transplantation, or a combination thereof.

Radiosensitizers can be administered in conjunction with a therapeutically effective amount of PARP inhibitors, where the PARP inhibitors can promote the incorporation of radiosensitizers to the target cells or the PARP inhibitors can control the flow of therapeutics, nutrients, and/or oxygen to the target cells. Similarly, chemosensitizers are also known to increase the sensitivity of cancerous cells to the toxic effects of chemotherapeutic compounds. Exemplary chemotherapeutic agents that can be used in conjunction with PARP inhibitors include, but are not limited to, adriamycin, camptothecin, dacarbazine, carboplatin, cisplatin, daunorubicin, docetaxel, doxorubicin, interferon (alpha, beta, gamma), interleukin 2, innotecan, paclitaxel, streptozotocin, temozolomide, topotecan, and therapeutically effective analogs and derivatives of the same. In addition, other therapeutic agents which can be used in conjunction with a PARP inhibitors include, but are not limited to, 5-fluorouracil, leucovorin, 5'-amino-5'-deoxythymidine, oxygen, carbogen, red cell transfusions, perfluorocarbons (e.g., Fluosol-DA), 2,3-DPG, BW12C, calcium channel blockers, pentoxyfylline, antiangiogenesis compounds, hydralazine, and L-BSO.

Radiosensitizers are known to increase the sensitivity of cancerous cells to the toxic effects of electromagnetic radiation. Many cancer treatment protocols currently employ radiosensitizers activated by the electromagnetic radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, photofrin, benzoporphyrin derivatives, NPe6, tin etioporphyrin SnET2, pheoborbide, bacteriochlorophyll, naphthalocyanines, phthalocyanines, zinc phthalocyanine, and therapeutically effective analogs and derivatives of the same.

The methods of treatment as disclosed herein can be via oral administration, transmucosal administration, buccal administration, nasal administration, inhalation, parental administration, intravenous, subcutaneous, intramuscular, sublingual, transdermal administration, and rectal administration.

Non-invasive administration includes (1) topical application to the skin in the form of an ointment or cream; (2) direct topical application to oropharyngeal tissues; (3) oral administration; (4) nasal administration as an aerosol; (5) intravaginal application of the inhibitor in the form of a suppository, cream or foam; (6) direct application to the uterine cervix; (7) rectal administration via suppository, irrigation or other suitable means; (8) bladder irrigation; and (9) administration of aerosolized formulation of the inhibitor to the lung.

Pharmaceutical compositions of PARP inhibitors for the methods of the present invention include compositions wherein the active ingredient is contained in a therapeutically or prophylactically effective amount. The actual amount effective for a particular application will depend, inter alia, on the condition being treated and the route of administration. Determination of an effective amount is well within the capabilities of those skilled in the art. The pharmaceutical compositions comprise the PARP inhibitors, one or more pharmaceutically acceptable carriers, diluents or excipients, and optionally additional therapeutic agents. The compositions can be formulated for sustained or delayed release.

In some embodiments, the PARP inhibitors can be administered locally or topically in gels, ointments, solutions, impregnated bandages, liposomes, or biodegradable microcapsules. Compositions or dosage forms for topical application can include solutions, lotions, ointments, creams, gels, suppositories, sprays, aerosols, suspensions, dusting powder, impregnated bandages and dressings, liposomes, biodegradable polymers, and artificial skin. Typical pharmaceutical carriers which make up the foregoing compositions include alginates, carboxymethylcellulose, methylcellulose, agarose, pectins, gelatins, collagen, vegetable oils, mineral oils, stearic acid, stearyl alcohol, petrolatum, polyethylene glycol, polysorbate, polylactate, polyglycolate, polyanhydrides, phospholipids, polyvinylpyrrolidone, and the like.

The compositions can be administered by injection, topically, orally, transdermally, rectally, or via inhalation. The oral form in which the therapeutic agent is administered can include powder, tablet, capsule, solution, or emulsion. The effective amount can be administered in a single dose or in a series of doses separated by appropriate time intervals, such as hours. Pharmaceutical compositions can be formulated in conventional manner using one or more physiologically acceptable carriers comprising excipients and auxiliaries which facilitate processing of the active compounds into preparations which can be used pharmaceutically. Proper formulation is dependent upon the route of administration chosen. Suitable techniques for preparing pharmaceutical compositions of the therapeutic agents of the present invention are well known in the art.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular PARP inhibitor, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

EXAMPLES

Example I

Goal: This study relates to analyzing the effect of the 3-nitro-4-iodobenzamide (compound of formula III) in vitro on cultured OVCAR-3 cells' and HeLa cells' metabolic fluxes using $[1,2\text{-}^{13}C_2]$-D-glucose as the only source of glucose. The analysis includes correlating fluxes with cell growth-modifying effect, analyzing mechanism of anti-proliferative action and analyzing potential toxicity, selectivity, and efficacy. Target metabolites include glucose (culture medium and pellet glycogen), lactate (culture medium), $^{13}CO_2$ (culture medium), C:14 (myristate); C:16 (palmitate); C:18 (stearate); C:18-1 (oleate); C:20; C:22; C:24 (cell pellet), acetyl-CoA synthesis for fatty acids (cell pellet), and RNA ribose and DNA deoxyribose (cell pellet). Target fluxes include glucose uptake from culture media; lactate production from glucose (anaerobic glycolysis); $^{13}CO_2$ release from glucose via TCA cycle; glycogen synthesis; de novo fatty acid synthesis, elongation, desaturation and acetyl-CoA synthesis; and pentose cycle-RNA and DNA ribose synthesis via oxidative and non-oxidative reactions.

Materials & Methods: The tracer for this metabolic profiling study, stable isotope $[1, 2\text{-}^{13}C_2]$-D-glucose, is purchased with >99% purity and 99% isotope enrichment for each position from Cambridge Isotope Laboratories, Inc. (Andover, Mass.).

Cells & cell culture: OVCAR3 and Hela cells are purchased from American Type Culture Collection (ATCC). The cells are cultured according to instructions obtained from ATCC. The cells are incubated at 37° C., 5% $CO_2$ and 95% humidity and passed by using trypsin 0.25% (Gibco/BRL) no more than ten times after receipt from the ATCC and prior to use in this study.

Seventy-five percent confluent cultures cells are incubated in $[1,2\text{-}^{13}C_2]$D-glucose-containing media (100 mg/dl total concentration=5 mM; 50% isotope enrichment—i.e. half unlabeled glucose, half labeled with the stable isotope $^{13}C$ tracer). Cells are plated at a density of $10^6$ per T75 culture flask and 3-nitro-4-iodobenzamide is added in a concentration range of 0.3 and 3 μM to culture media. Control cultures are treated with vehicle only. The doses of 3-nitro-4-iodobenzamide for the present study are selected based on in vitro experiments demonstrating that this drug effectively controls glycogen phosphorylase activity in the presence or absence of glucose in human cells (Andersen B, et al. 2002, *Biochem J* 367: 443-450). Glucose and lactate levels in the medium are measured using a Cobas Mira chemistry analyzer (Roche Diagnostics, Pleasanton, Calif., USA).

RNA ribose stable isotope studies: RNA ribose is isolated by acid hydrolysis of cellular RNA after Trizol purification of cell extracts. Total RNA amounts are assessed by spectrophotometric determination, in triplicate cultures. Ribose is derivatized to its aldonitrile acetate form using hydroxylamine in pyridine with acetic anhydride (Supelco, Bellefonte, Pa.) before mass spectral analyses. The ion cluster is monitored around the m/z 256 (carbons 1-5 of ribose) (chemical ionization, CI) and m/z 217 (carbons 3-5 of ribose) and m/z 242 (carbons 1-4 of ribose) (electron impact ionization, EI) to determine molar enrichment and the positional distribution of $^{13}C$ in ribose. By convention, the base mass of $^{12}C$-compounds (with their derivatization agents) is given as $m_0$ as measured by mass spectrometry (Boros L G, et al. 2002, *Drug Discov. Today* 7: 364-372).

Ribose molecules labeled with a single $^{13}C$ atom on the first carbon position (m1) recovered from RNA are used to gauge the ribose fraction produced by direct oxidation of glucose through the G6PD pathway. Ribose molecules labeled with $^{13}C$ on the first two carbon positions (m2) are used to measure the fraction produced by transketolase. Doubly labeled ribose molecules ($m_2$ and $m_4$) on the fourth and fifth carbon positions are used to measure molar fraction produced by triose phosphate isomerase and transketolase.

Lactate: Lactate from the cell culture media (0.2 ml) is extracted by ethylene chloride after acidification with HCL. Lactate is derivatized to its propylamine-heptafluorobutyrate ester form and the m/z 328 (carbons 1-3 of lactate) (chemical ionization, CI) is monitored for the detection of $m_1$ (recycled lactate through the PC) and $m_2$ (lactate produced by the Embden-Meyerhof-Pamas pathway) for the estimation of pentose cycle activity (Lee W N, et al. 1998, *Am J Physiol* 274: E843-E851). The $m_1/m_2$ ratios produced in lactate are recorded and released by OVCAR3 and Hela cells in order to determine pentose cycle activity versus anaerobic glycolysis in response to 3-nitro-4-iodobenzamide treatment.

Glutamate: Glutamate label distribution from glucose is suitable for determining glucose oxidation versus anabolic glucose use within the TCA cycle, also known as anaplerotic flux. Tissue culture medium is first treated with 6% perchloric acid and the supernatant is passed through a 3 cm³ Dowex-50 (H+) column. Amino acids are eluted with 15 ml 2N ammonium hydroxide. To further separate glutamate from glutamine, the amino acid mixture is passed through a 3 cm³ Dowex-1 (acetate) column, and then collected with 15 ml 0.5 N acetic acid. The glutamate fraction from the culture medium is converted to its trifluoroacetyl butyl ester (TAB). Under EI conditions, ionization of TAB-glutamate produces two fragments, m/z 198 and m/z 152, corresponding to $C_2$-$C_5$ and $C_2$-$C_4$ of glutamate (Lee W N, et al. 1996, *Developmental Neuroscience* 18: 469-477). Glutamate labeled on the 4-5 carbon positions indicates pyruvate dehydrogenase activity while glutamate labeled on the 2-3 carbon positions indicates pyruvate carboxylase activity for the entry of glucose carbons to the TCA cycle. TCA cycle anabolic glucose utilization is calculated based on the $m_1/m_2$ ratios of glutamate (Leimer K R, et al. 1977, *J. Chromatography* 141: 121-144).

Fatty acids: Palmitate, stearate, cholesterol and oleate are extracted after saponification of cell pellets in 30% KOH and 100% ethanol using petroleum ether. Fatty acids are converted to their methylated derivative using 0.5N methanolic-HCL. Palmitate, stearate and oleate are monitored at m/z 270, m/z 298 and m/z 264, respectively, with the enrichment of $^{13}C$ labeled acetyl units which reflect synthesis, elongation and desaturation of the new lipid fraction as determined by mass isotopomer distribution analysis (MIDA) of different isotopomers (Lee W N, et al. 1998, *J. Biol. Chem.* 273: 20929-20934; Lee W N, et al. 1995, *Anal Biochem* 226: 100-112).

Gas Chromatography/Mass Spectrometry (GC/MS): Mass spectral data are obtained on the HP5973 mass selective detector connected to an HP6890 gas chromatograph. The settings are as follows: GC inlet 250° C., transfer line 280° C., MS source 230° C., MS Quad 150° C. An HP-5 capillary column (30 m length, 250 μm diameter, 0.25 μm film thickness) is used for glucose, ribose and lactate analyses. Transketolase has the highest metabolic control coefficient in the non-oxidative branch of the pentose cycle (Sabate L, et al. 1995, *Mol. Cell. Biochem.* 142: 9-17; Comin-Anduix B, et al. 2001, *Eur. J. Biochem.* 268: 4177-4182). It should be noted, though, that transketolase and transaldolase, besides other enzymes, all can participate in non-oxidative pentose cycle metabolism in human cells.

Data analysis and statistical methods: Each experiment is carried out using triplicate cell cultures for each condition within each experiment and experiments are repeated once. Mass spectroscopic analyses is carried out by three independent automatic injections of 1 µl samples by the automatic sampler and accepted only if the standard sample deviation is less than 1% of the normalized peak intensity. Statistical analysis is performed using the Student's t-test for unpaired samples. Two-tailed significance at the 99% confidence interval (µ+/−2.58 σ), p<0.01 indicates significant differences in glucose carbon metabolism in control and 3-nitro-4-iodobenzamide.

Results: Tracer treatment is successful in HeLa cells and all cultures' tracer labeled glucose fraction is between 45% and 55% of total glucose at 0.0 minutes. Twenty four, forty eight and seventy two hours of tracer incubation is sufficient to generate HeLa cell specific metabolite labeling profiles. There are differences in HeLa cell glucose metabolism in response to 3-nitro-4-iodobenzamide. The effects are dose-responsive and are most consistent with decreased medium and long chain fatty acid de novo synthesis from glucose. De novo synthesis of arachidic acid (C:20) is spared from the inhibitory action of 3-nitro-4-iodobenzamide. Acetyl-CoA enrichment from glucose for arachidic acid synthesis is high in the 3-nitro-4-iodobenzamide treated HeLa cultures.

Oxidation of glucose into $CO_2$ and ATP production in the TCA cycle are not affected by 3-nitro-4-iodobenzamide. There is a dose-dependent increase in acetyl-CoA contribution from glucose to long chain saturated fatty acids (C:20-C:24). 3-nitro-4-iodobenzamide is a metabolically active compound in HeLa cells. De novo medium and long chain fatty acid (C:14-C:18) syntheses are decreased with low contribution to acetyl-CoA synthesis from glucose. 3-nitro-4-iodobenzamide decreases cell membrane formation via limited de novo fatty acid synthesis as the underlying mechanism of its anti-proliferative action in HeLa cells. 3-nitro-4-iodobenzamide increases acetyl-CoA formation from glucose for arachidic acid formation and therefore it can stimulate prostaglandin synthesis. 3-nitro-4-iodobenzamide has no toxic effects on cell energy production, nucleic acid turnover and glycogen synthesis. 3-nitro-4-iodobenzamide has no inhibitory effect on substrate (glucose) uptake and activation (phosphorylation).

Tracer treatment is successful in OVCAR-3 cells and all cultures' tracer labeled glucose fraction is between 45% and 55% of total glucose at 0.0 minutes. Seventy two hours of tracer incubation is sufficient to generate HeLa cell specific metabolite labeling profiles. There are significant differences in OVCAR-3 cell glucose metabolism in response to 3-nitro-4-iodobenzamide. The effects are dose-responsive and are most consistent with decreased medium and long chain fatty acid de novo synthesis from glucose as well as decreased acetyl-CoA synthesis from glucose.

Medium and long chain fatty acid de novo synthesis (C:14-C:18) are speared from the inhibitory action of 3-nitro-4-iodobenzamide in OVCAR-3 cells. De novo fatty acid synthesis is relatively low (<30%) in OVCAR-3 cells. Aldolase and triose phosphate isomerase are active during DNA synthesis and transketolase as well as G6PDH are target enzymes of 3-nitro-4-iodobenzamide treatment. Glycogen synthesis and breakdown via the direct pathway is inhibited by 3-nitro-4-iodobenzamide.

Figure 3A:
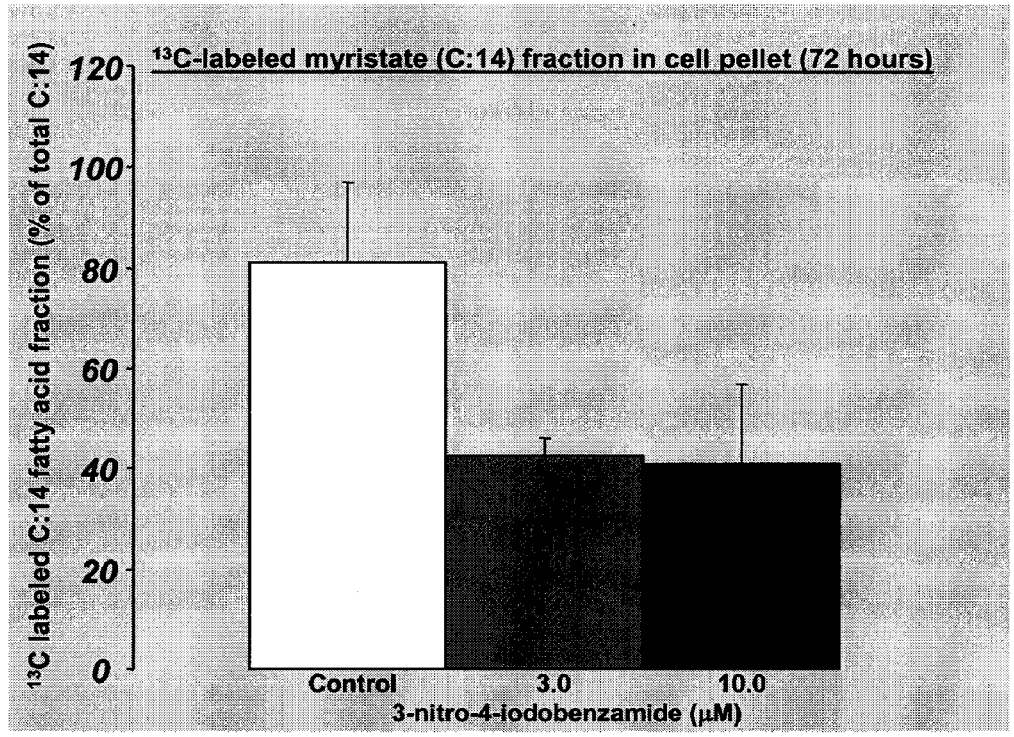
FIGS. 3A and B illustrate that 3 and 10 μM of 3-nitro-4-iodobenzamide inhibit myristate synthesis in Hela cells.
Figure 3B:
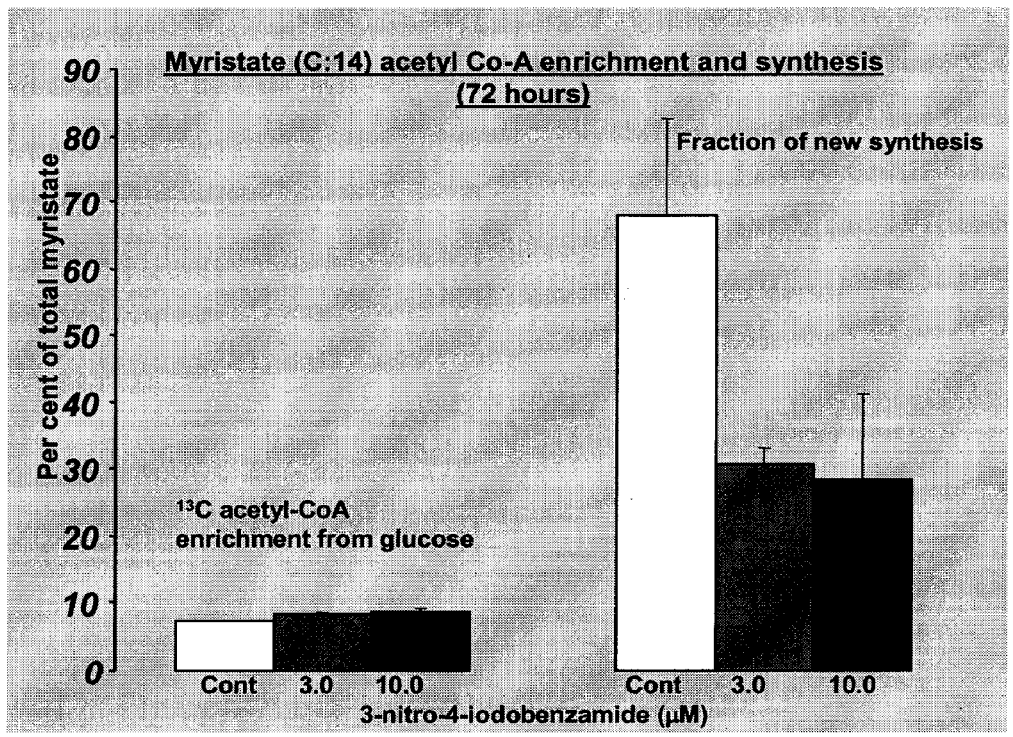
Figure 4A:
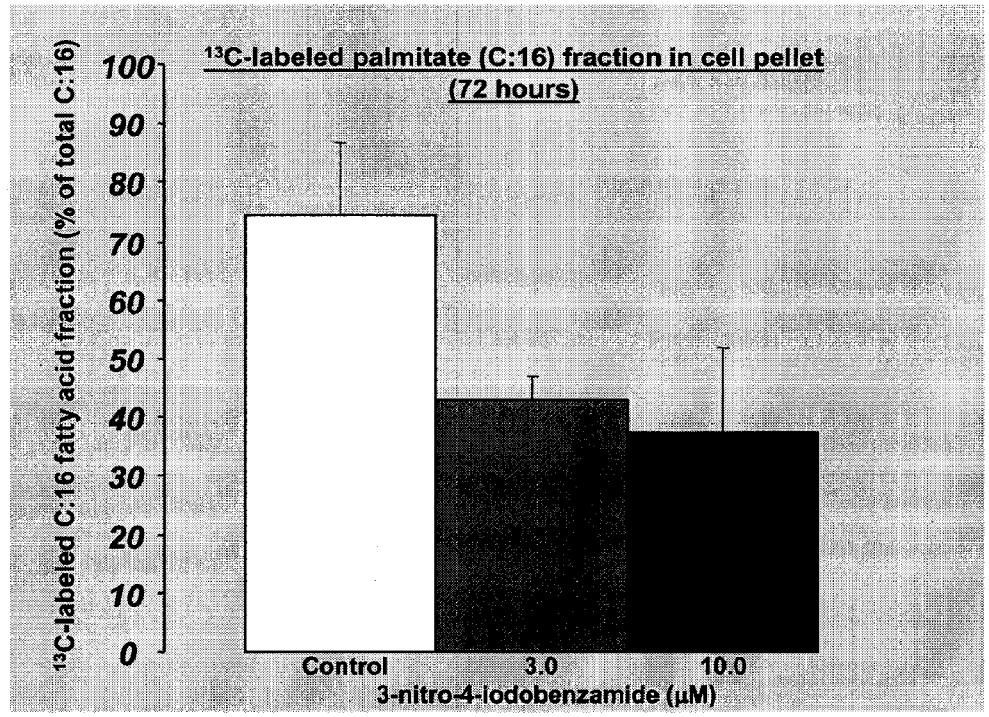
FIGS. 4A and B illustrate that 3 and 10 μM of 3-nitro-4-iodobenzamide inhibit palmitate synthesis in Hela cells.
Figure 4B:
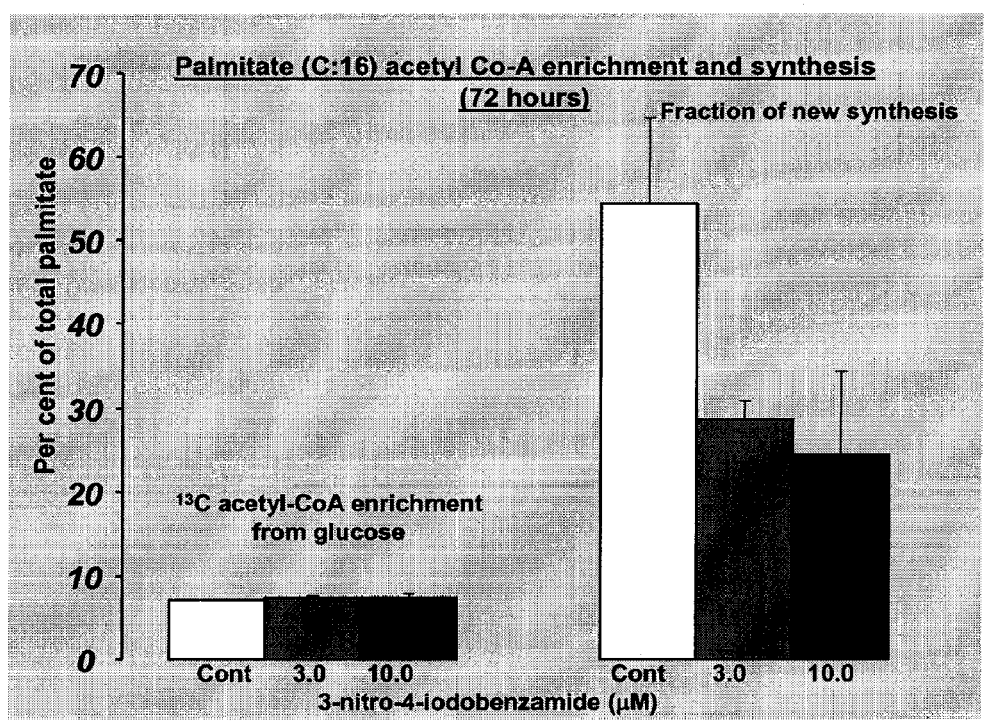
Figure 5A:
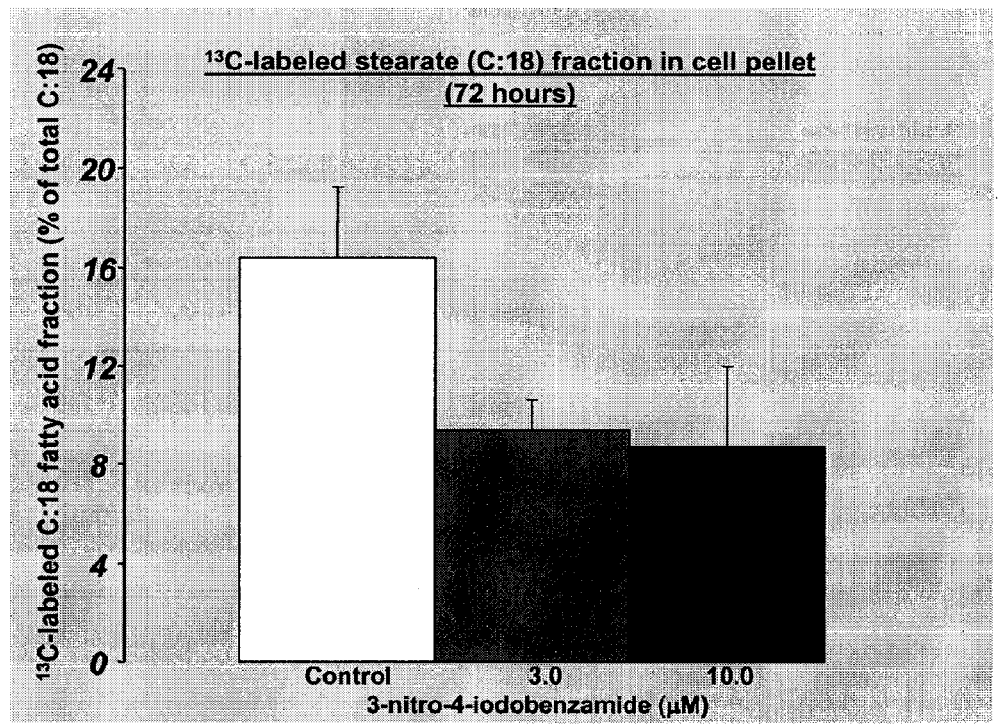
FIGS. 5A and B illustrate that 3 and 10 μM of 3-nitro-4-iodobenzamide inhibit stearate synthesis in Hela cells.
Figure 5B:
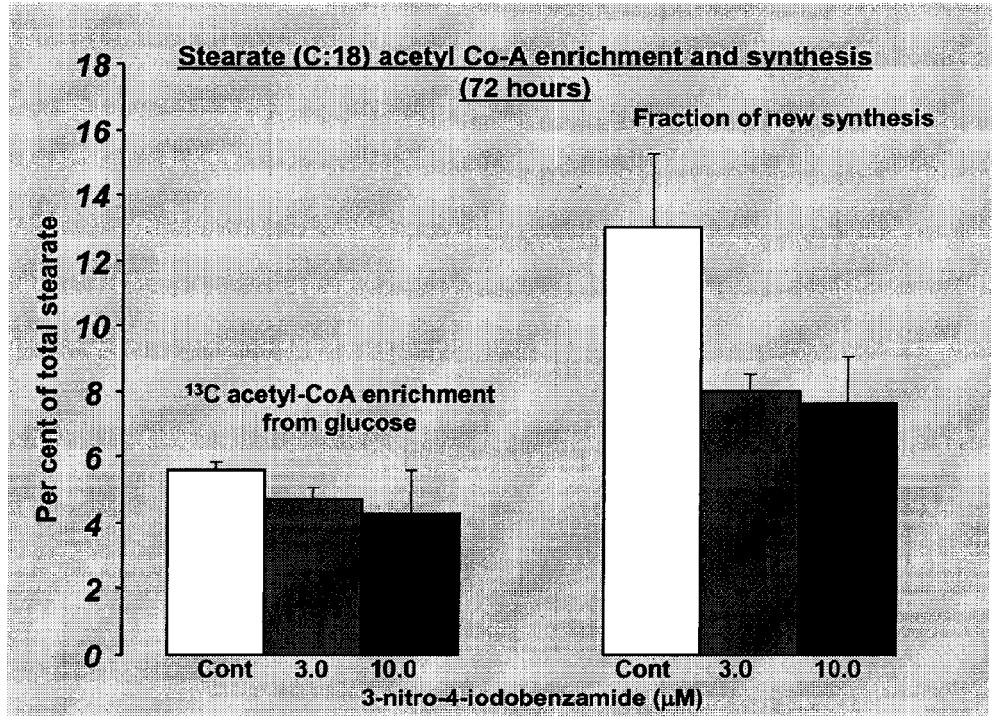
Figure 6A:
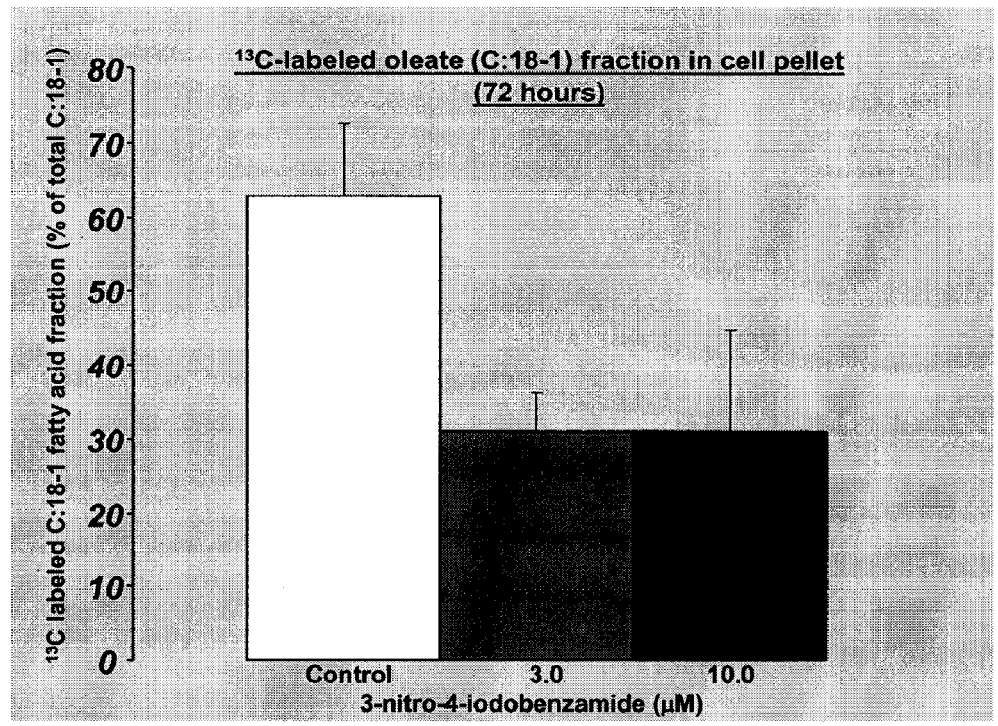
FIGS. 6A and B illustrate that 3 and 10 μM of 3-nitro-4-iodobenzamide inhibit oleate synthesis in Hela cells.
Figure 6B:
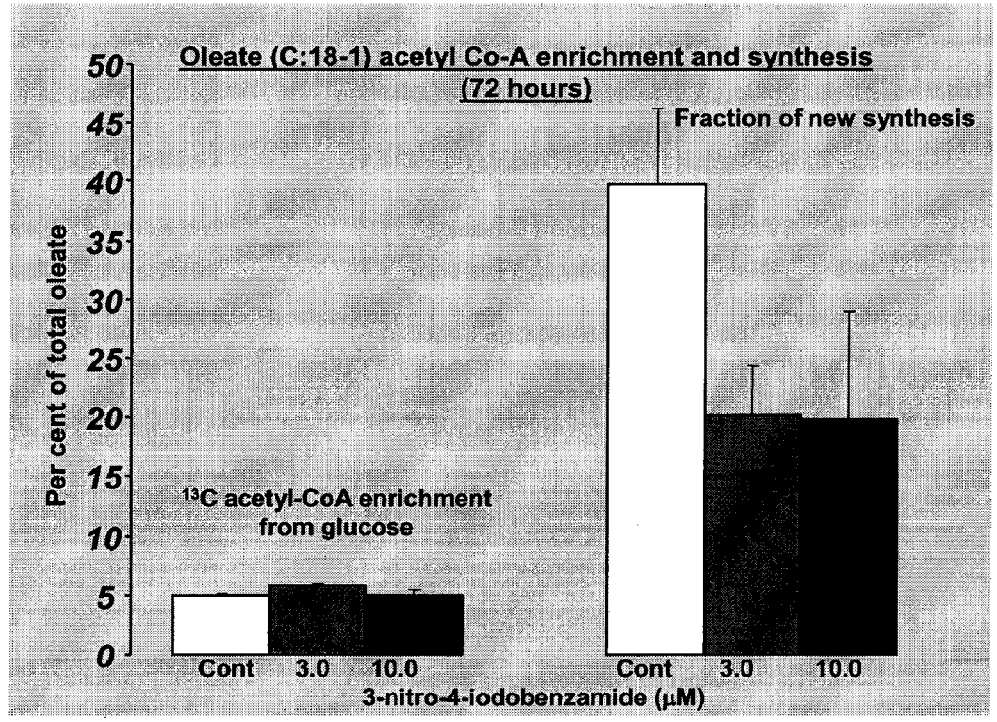
Figure 7A:
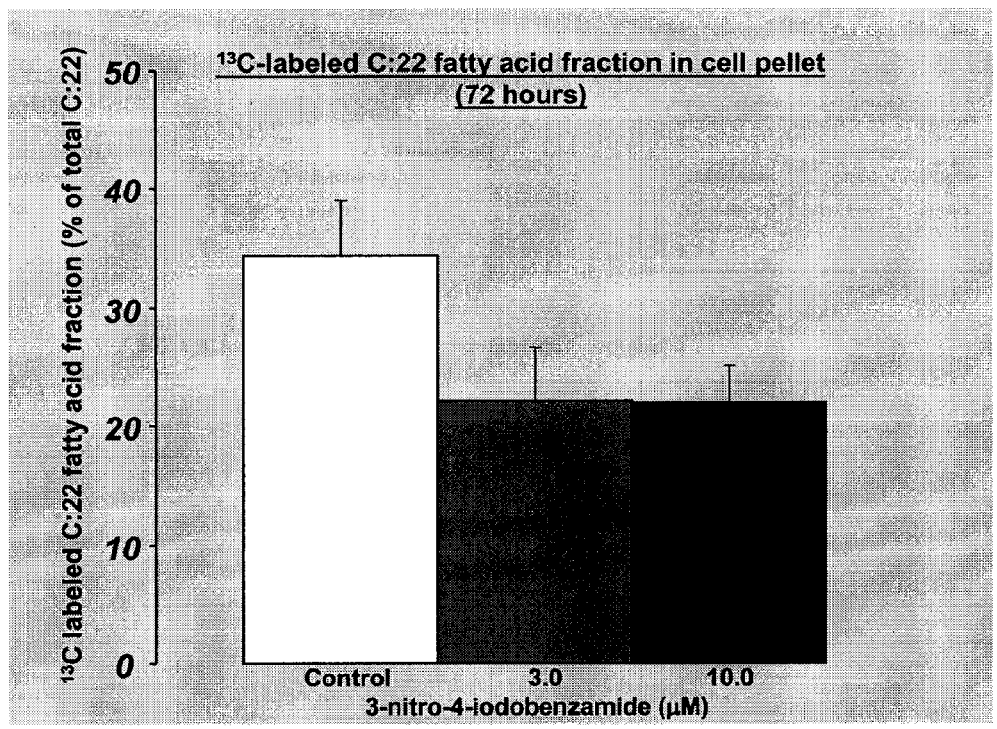
FIGS. 7A and B illustrate that 3 and 10 μM of 3-nitro-4-iodobenzamide inhibit C:22 fatty acid synthesis in Hela cells.
Figure 7B:
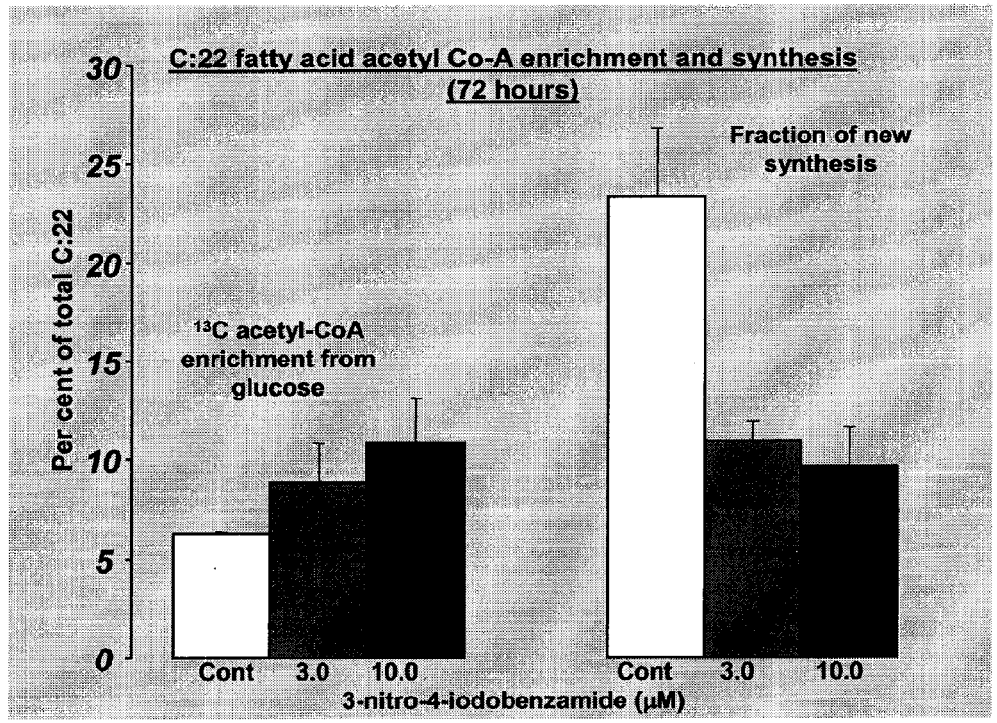
Figure 8A:
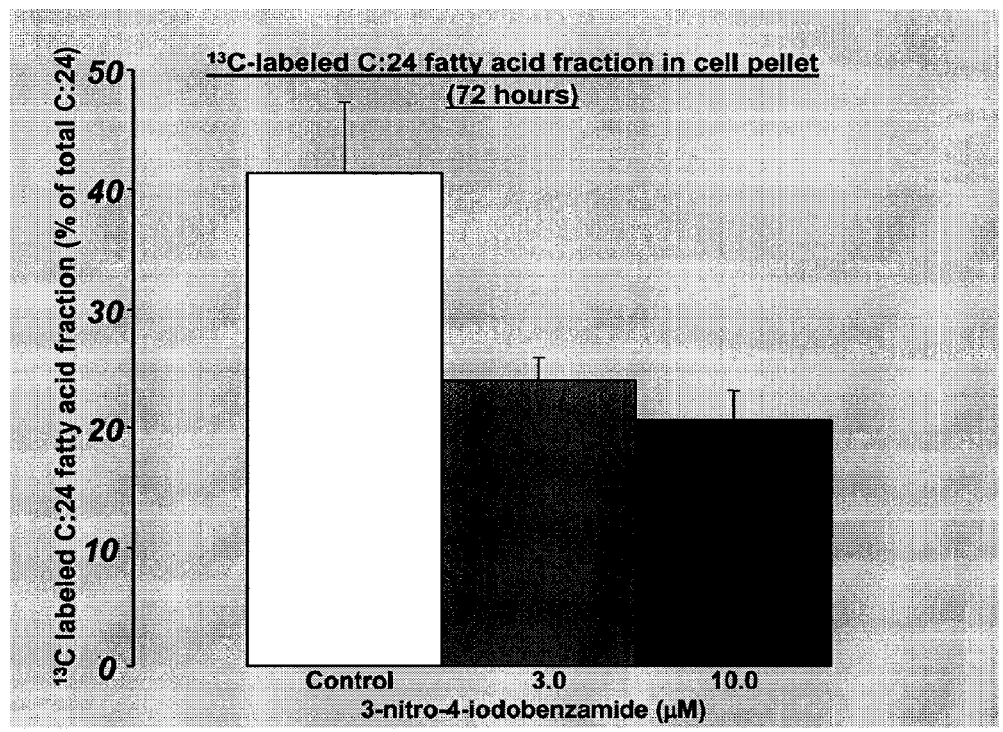
FIGS. 8A and B illustrate that 3 and 10 μM of 3-nitro-4-iodobenzamide inhibit C:24 fatty acid synthesis in Hela cells.
Figure 8B:
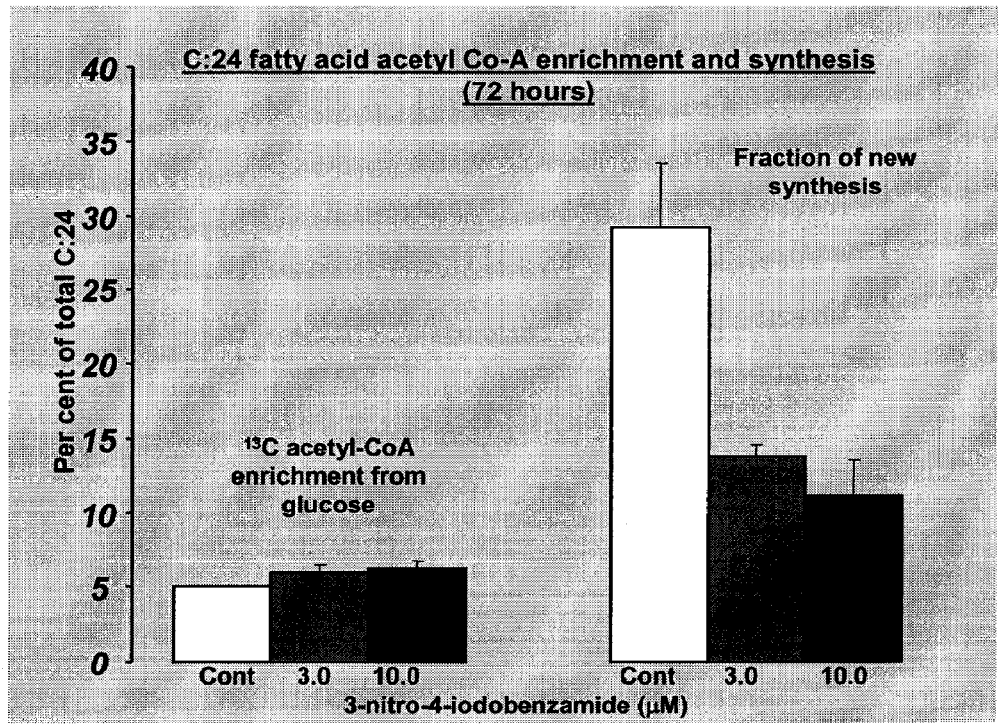
Figure 9A:
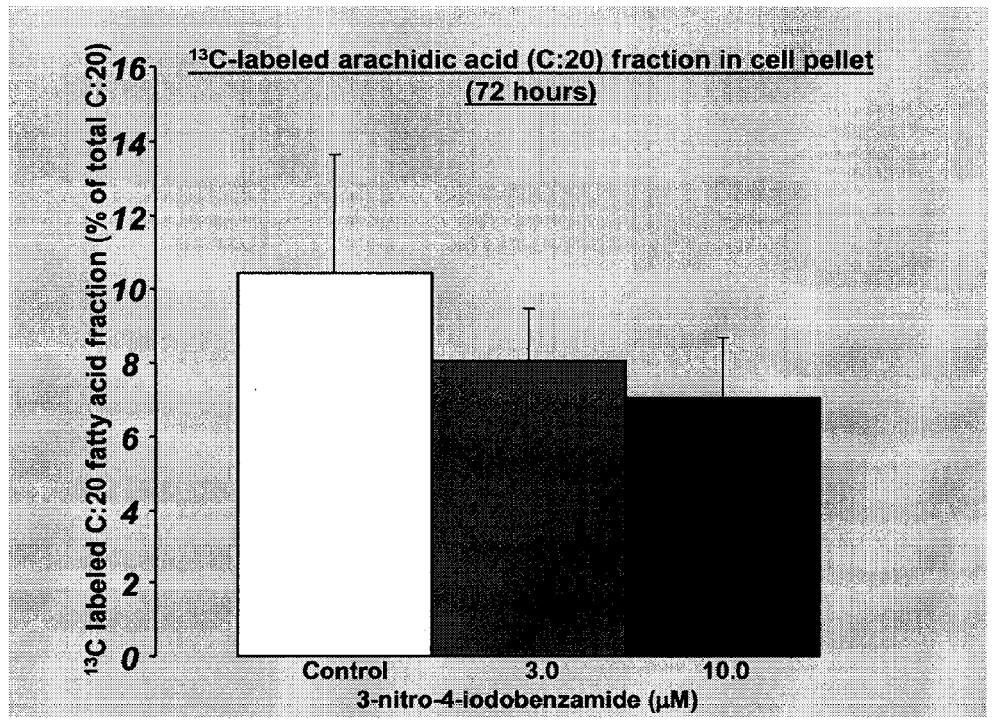
FIGS. 9A and B illustrate that 3 and 10 μM of 3-nitro-4-iodobenzamide inhibit arachidic acid synthesis in OVCAR-3 cells.
Figure 9B:
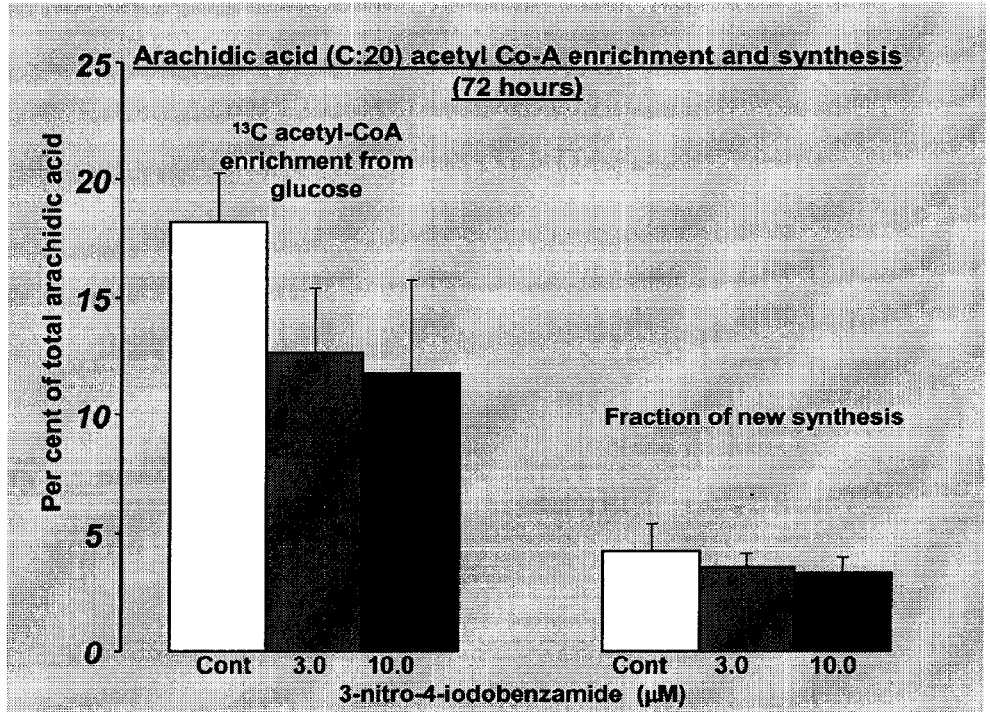
Figure 10A:
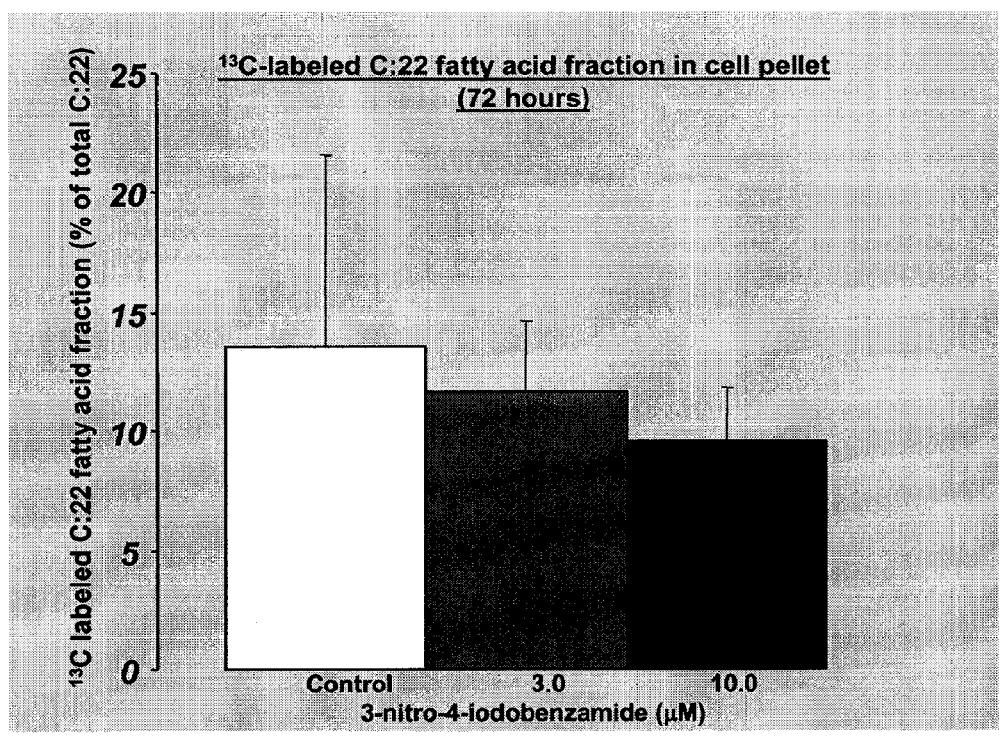
FIGS. 10A and B illustrate that 3 and 10 μM of 3-nitro-4-iodobenzamide inhibit C:22 fatty acid synthesis in OVCAR-3 cells.
Figure 10B:
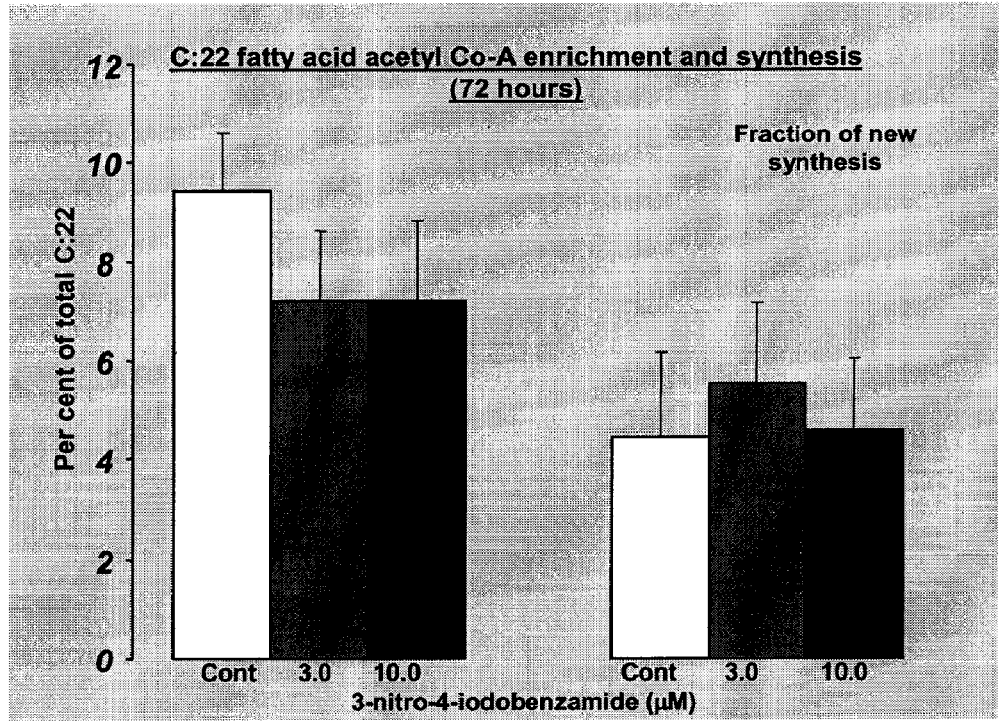
Figure 11A:
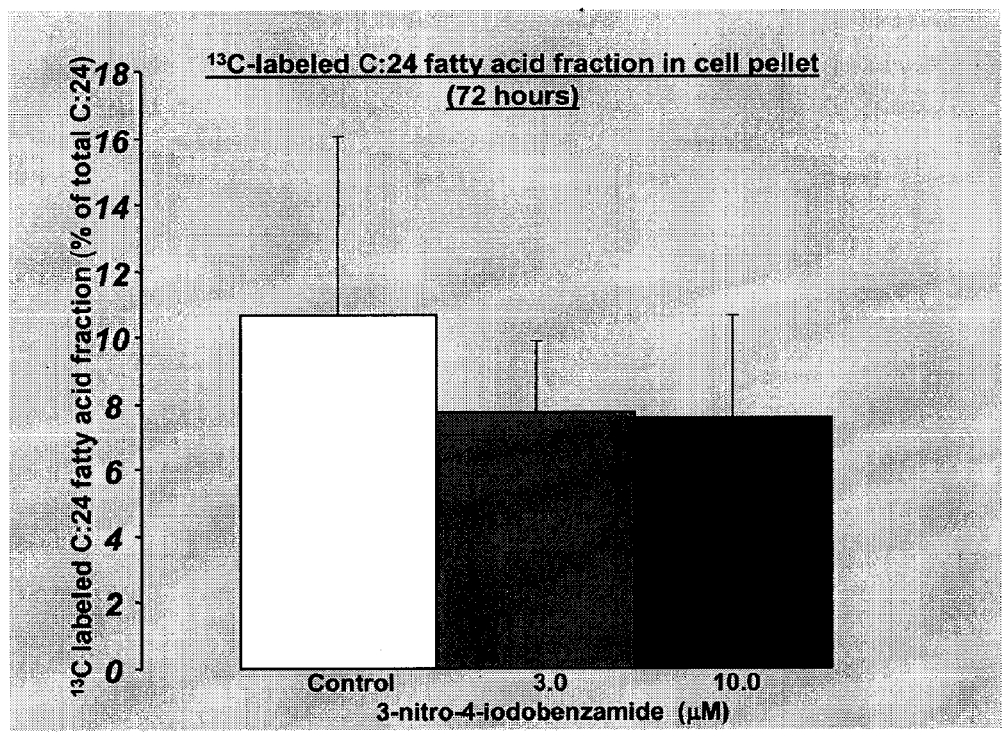
FIGS. 11A and B illustrate that 3 and 10 μM of 3-nitro-4-iodobenzamide inhibit C:24 fatty acid synthesis in OVCAR-3 cells.
Figure 11B:
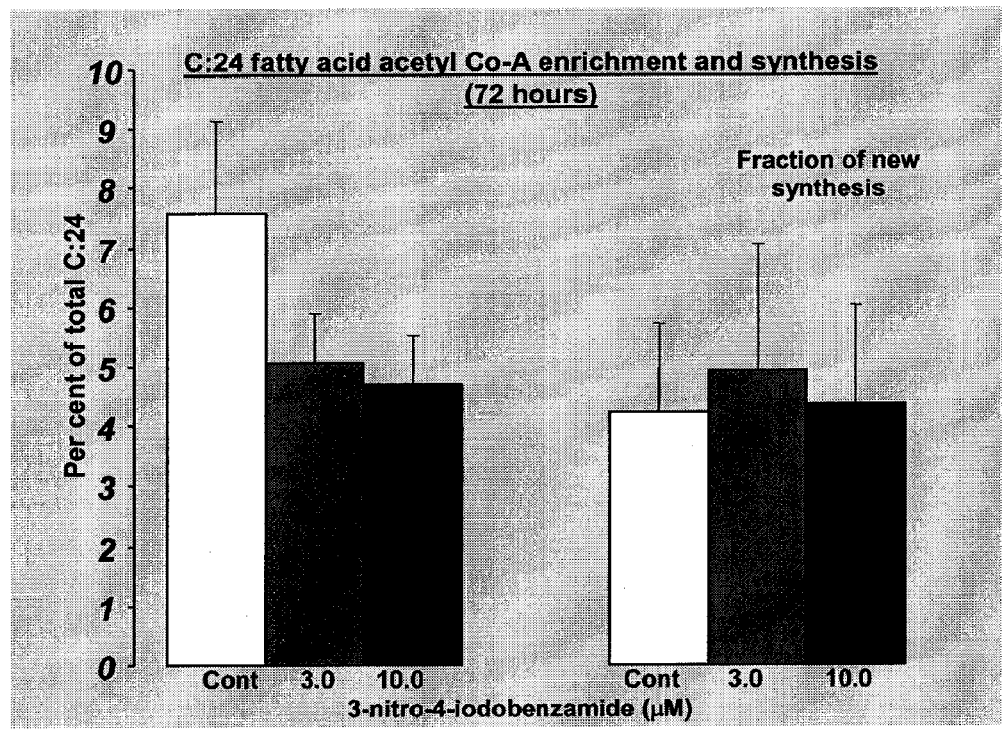

There is a dose-dependent increase in acetyl-CoA contribution from glucose to long chain saturated fatty acids (C:20-C:24). 3-nitro-4-iodobenzamide is a metabolically active compound in OVCAR-3 cells. De novo medium and long chain fatty acid (C:14-C:18) syntheses are slightly increased with no significant change in acetyl-CoA synthesis from glucose. 3-nitro-4-iodobenzamide decreases cell membrane formation via limited de novo long chain (C:20-C:24) fatty acid synthesis as the underlying mechanism of its anti-proliferative action in OVCAR-3 cells. The 3-nitro-4-iodobenzamide also inhibits G6PDH and transketolase fluxes for DNA deoxyribose synthesis and direct glycogen synthesis. The 3-nitro-4-iodobenzamide has no toxic effects on cell energy production, and nucleic acid RNA turnover. The results of these studies are depicted in FIGS. 3A, 3B ($^{13}$C-labeled myristate (C:14) at 72 hours), 4A, 4B (($^{13}$C-labeled palmitate (C:16) at 72 hours), 5A, 5B ($^{13}$C-labeled stearate (C:18) at 72 hours), 6A, 6B ($^{13}$C-labeled oleate (C:18-1) at 72 hours), 7A, 7B ($^{13}$C-labeled C:22 fatty acid at 72 hours), 8A, 8B ($^{13}$C-labeled C:24 fatty acid at 72 hours), 9A, 9B ($^{13}$C-labeled arachidic acid (C:20) at 72 hours), 10A, 10B ($^{13}$C-labeled C:22 fatty acid at 72 hours), and 11A, 11B ($^{13}$C-labeled C:24 fatty acid at 72 hours). In each case, the "A" figure shows the amount of fatty acid incorporation in the cell pellet, while the "B" figure shows the $^{13}$Acetyl Co-A enrichment from glucose (left) and the fraction of new fatty acid synthesis (right). These results demonstrate that the PARP-1 inhibitor 3-nitro-4-iodobenzamide inhibits fatty acid synthesis in cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method of monitoring a therapeutic effectiveness of a compound of formula Ia or metabolite thereof or pharmaceutically acceptable salt thereof in a treatment of a fatty acid synthesis related disease selected from the group consisting of obesity, diabetes, or cardiovascular disease comprising: (i) administering an effective amount of a compound of formula Ia or metabolite thereof or pharmaceutically acceptable salt thereof to a patient to inhibit fatty acid synthesis; (ii) comparing a first and a second level of fatty acid in a first and second sample from said patient wherein said first level and said first sample are obtained prior to administration of said compound of formula Ia or metabolite thereof or pharmaceutically acceptable salt thereof and said second level and said second sample are obtained after administration of said compound of formula Ia or metabolite thereof or pharmaceutically acceptable salt thereof; and (iii) determining a therapeutic effectiveness of said compound of formula Ia or metabolite thereof or pharmaceutically acceptable salt thereof in a treatment of a disease in said patient based on said comparison, wherein the compound formula Ia is a compound of the formula:

Formula Ia

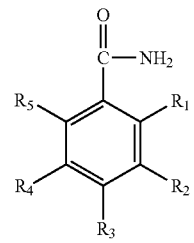

wherein $R_1$, $R_2$, $R_3$, $R_4$, and $R_5$ are, independently selected from the group consisting of hydrogen, hydroxy, amino, nitro, iodo, bromo, fluoro, chloro, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents is always nitro, and at least one substituent positioned adjacent to a nitro is always iodo, or a metabolite thereof or a pharmaceutically acceptable salt thereof.

2. The method of claim 1, wherein said inhibition of said fatty acid synthesis comprises inhibiting at least one enzyme of a glucose pathway or a fatty acid biosynthetic pathway.

3. The method of claim 1, wherein when said second level of fatty acid in said second sample is lower than said first level of fatty acid in said first sample then said compound of formula Ia or metabolite thereof or a pharmaceutically acceptable salt thereof is therapeutically effective.

4. The method of claim 1, wherein when said second level of fatty acid in said second sample is higher than said first level of fatty acid in said first sample then said compound of formula Ia or metabolite thereof or pharmaceutically acceptable salt thereof is therapeutically ineffective.

5. The method of claim 1, wherein said first level and said second level of fatty acid is determined by assay techniques.

6. The method of claim 1, wherein said first level and said second level of fatty acid is determined by mass spectrometry.

7. The method of claim 6, wherein said mass spectrometry is mass isotopomer distribution analysis.

8. The method of claim 1, wherein said compound of formula Ia is a compound of formula III, or a pharmaceutically acceptable salt thereof:

Formula III

9. The method of claim 1, wherein said disease is obesity.

10. The method of claim 1, wherein said administration is selected from the group consisting of oral administration, transmucosal administration, buccal administration, nasal administration, inhalation, parental administration, intravenous, subcutaneous, intramuscular, sublingual, transdermal administration, and rectal administration.

11. The method of claim 1, wherein said first level of fatty acid in said first sample is determined from said patient's medical history.

12. The method of claim 1, wherein the metabolite of the compound of formula (Ia) is selected from the group consisting of

MS472

-continued

MS601

MS328

MS183

MS182

MS414
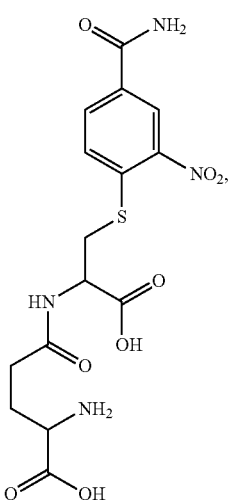
or a salt thereof, and
a compound of formula MS213
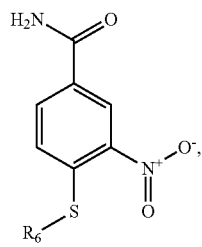
MS213
wherein $R_6$ is selected from a group consisting of hydrogen, alkyl ($C_1$-$C_8$), alkoxy ($C_1$-$C_8$), isoquinolinones, indoles, thiazole, oxazole, oxadiazole, thiphene, or phenyl.
\* \* \* \* \*

Disclaimer

7,994,222 B2 — Valeria S. Ossovskaya, San Francisco, CA (US); Barry M. Sherman Hillsborough, CA (US), MONITORING OF THE INHIBITION OF FATTY ACID SYNTHESIS BY IODONITROBENZAMIDE COMPOUNDS. Patented date August 9, 2011. Disclaimer filed December 19, 2013 by the Assignee, BiPar Sciences, Inc.

Hereby enter this disclaimer to the entire term of said patent.

*(Official Gazette, April 1, 2014)*